(12) United States Patent
Ruan et al.

(10) Patent No.: US 8,071,296 B2
(45) Date of Patent: Dec. 6, 2011

(54) NUCLEIC ACID INTERACTION ANALYSIS

(75) Inventors: Yijun Ruan, Singapore (SG); Melissa Jane Fullwood, Singapore (SG); Chia Lin Wei, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 98 days.

(21) Appl. No.: 11/373,519

(22) Filed: Mar. 13, 2006

(65) Prior Publication Data
US 2007/0238101 A1 Oct. 11, 2007

(51) Int. Cl.
*C12Q 1/68* (2006.01)
(52) U.S. Cl. ........................................................ 435/6.1
(58) Field of Classification Search .................. 536/23.1
See application file for complete search history.

(56) References Cited

U.S. PATENT DOCUMENTS

| | | | |
|---|---|---|---|
| 6,054,276 A | | 4/2000 | Macevicz |
| 6,136,537 A | * | 10/2000 | Macevicz ........................... 435/6 |
| 6,383,743 B1 | | 5/2002 | Kinzler et al. |
| 6,410,243 B1 | | 6/2002 | Wyrick et al. |
| 6,498,013 B1 | | 12/2002 | Velculescu et al. |
| 2004/0146866 A1 | | 7/2004 | Fu |
| 2005/0059022 A1 | | 3/2005 | Ruan et al. |
| 2005/0255501 A1 | | 11/2005 | Ng et al. |
| 2006/0024681 A1 | * | 2/2006 | Smith et al. ........................ 435/6 |
| 2006/0084111 A1 | | 4/2006 | Ruan et al. |
| 2006/0281097 A1 | | 12/2006 | Chiu et al. |

FOREIGN PATENT DOCUMENTS

| | | |
|---|---|---|
| WO | 0116378 A2 | 3/2001 |
| WO | 0148247 A2 | 7/2001 |
| WO | 0210438 A2 | 2/2002 |
| WO | 0214550 A2 | 2/2002 |
| WO | 2004050918 A1 | 6/2004 |
| WO | 2005007814 A2 | 1/2005 |
| WO | 2005026391 A1 | 3/2005 |
| WO | 2005/042781 A2 | 5/2005 |
| WO | 2006003721 A1 | 1/2006 |
| WO | 2006031204 A1 | 3/2006 |
| WO | 2006135342 A1 | 12/2006 |
| WO | 2007004057 A2 | 1/2007 |
| WO | 2007057785 A2 | 5/2007 |
| WO | 2007106047 A1 | 9/2007 |

OTHER PUBLICATIONS

Kim et al. Nature Methods, vol. 2, No. 1, pp. 47-53, published online Dec. 2004, print date Jan. 2005.*
Marinescu et al. Bioinformatics Applications Note, vol. 22, No. 8, pp. 990-1001, Feb. 24, 2006.*
Antequera F. and Bird A. "Number of CpG islands and genes in human and mouse". Proc. Natl. Acad. Sci. USA, vol. 90(24):11995-11999, 1993.
Bonetta L. "Gene expression: one size does not fit all", Nature Methods, vol. 3(5):401-409, 2006.
Brenner S. et al. "Gene expression analysis by massively parallel signature sequencing (MPSS) on microbead arrays", Nat. Biotechnol., vol. 18(6):630-634, 2000.
Buck M.J. and Lieb J.D. "ChIP-Chip: considerations for the design, analysis, and application of genome-wide chromatin immunoprecipitation experiments", Genomics 83(3):349-360, 2004.
Dekker J. et al. "Capturing Chromosome Conformation", Science, vol. 295(5558):1306-1311, 2002, 2 page supplement.
Dunn J.J. et al. "Genomic Signature Tags (GSTs): A System for Profiling Genomic DNA", Genome Research, 12(11):1756-1765, 2002.
Euskirchen G. et al. "CREB Binds to Multiple Loci on Human Chromosome 22", Mol. Cell. Biol., 24(9):3804-3814, 2004.
Li L. and Chandrasegaran S. "Alteration of the cleavage distance of Fok I restriction endonuclease by insertion mutagenesis", Proc. Natl. Acad. Sci. USA, vol. 90, 2764-2768, 1993.
Lieb J.D. et al. "Promoter-specific binding of Rap1 revealed by genome-wide maps of protein-DNA association", Nat. Genet. , vol. 28(4):327-334, 2001.
Margulies M. et al. "Genome sequencing in microfabricated high-density picolitre reactors", Nature, 437:376-380, 2005.
New England Biolabs Catalog 2005 and New England Biolabs (Ipswich, MA), 15 pages.
Szybalski W. "Universal restriction endonucleases: designing novel cleavage specificities by combining adapter oligodeoxynucleotide and enzyme moieties", Gene, 40:169-173, 1985.
Taverner N.V. et al. "Identifying transcriptional targets", Genome Biology, 5(3):210, 2004.
Weinmann A.S. et al. "Isolating human transcription factor targets by coupling chromatin immunoprecipitation and CpG island microarray analysis", Genes & Dev., 16(2):235-244, 2002.
Zhao, Zhihu, et al., "Circular chromosome conformation capture (4C) uncovers extensive networks of epigenetically regulated intra- and interchromosomal interactions," Nature Genetics, 38(11): 1341-1347 (Nov. 2006).
European Search Report for EP07251006, dated Aug. 2, 2007.
Wei, C-L., et al. "5' Long serial analysis of gene expression (Long SAGE) and 3' Long SAGE for transcriptome characterization and genome annotation" Proceedings of the National Academy of Sciences, vol. 101(32): 11701-11706, Jul. 22, 2004.
Ng, P., et al. "Gene identification signature (GIS) analysis for transcriptome characterization and genome annotation", Nature Methods, vol. 2(2):105-111, Feb. 2005.
Wei, C-L., et al. "A Global map of p53 transcription-factor binding sites in the human genome", Cell, vol. 124:207-219, Jan. 13, 2006.
Loh, Y-H., et al. "The Oct4 and Nanog transcription network regulates pluripotency in mouse embryonic stem cells", Nature Genetics, vol. 38(4):431-440, Apr. 2006.
Adams M.D. et al., "Complementary DNA Sequencing: Expressed sequence tags and human genome project," Science, 1991, 252(5013):1651-1656.

(Continued)

*Primary Examiner* — Gary Benzion
*Assistant Examiner* — Cynthia Wilder
(74) *Attorney, Agent, or Firm* — Rothwell, Figg, Ernst & Manbeck P.C.

(57) ABSTRACT

The present invention provides an isolated oligonucleotide and a method using the isolated oligonucleotide to detect and/or identify at least two polynucleotides from a nucleic acid-protein complex. The oligonucleotide comprises at least one first tag and at least one second tag, wherein the first and second tags are obtained from a nucleic acid-protein complex.

25 Claims, 14 Drawing Sheets

OTHER PUBLICATIONS

Brenner S. et al. "In vitro cloning of complex mixtures of DNA on microbeads: Physical separation of differentially expressed cDNAs," PNAS, 2000, 97(4):1665-1670.

Carroll J.S. et al. "Chromosome-wide mapping of estrogen receptor binding reveals long-range regulation requiring the forkhead protein FoxA1," Cell, 2005, 122:33-43.

Cawley S. et al. "Unbiased mapping of transcription factor binding sites along human chromosomes 21 and 22 points to widespread regulation of noncoding RNAs," Cell, 2004, 116:499-509.

Chiu K.P. et al. "PET-Tool: a software suite for comprehensive processing and managing of paired-end diTag (PET) sequence data," BMC Bioinformatics, 2006, 7(390):1-11.

Chum W.Y. and Kwan H.S., "Modification of Long SAGE for obtaining and cloning long concatemers," BioTechniques, 2005, 39(5):637-640.

Iyer V. R. et al. "Genomic binding sites of the yeast cell-cycle transcription factors SBF and MBF," Nature, 2001, 409:533-538.

Klug S.J. and Famulok M., "All you wanted to know about SELEX," Molecular Biology Reports, 1994, 20:97-107.

Mathupala S.P. and Sloan A.E., ""In-gel" purified ditags direct synthesis of highly efficient SAGE Libraries," BMC Genomics, 2002, 3:20-24.

Ng W.P. et al. "Gene identification signature (GIS) analysis: detailed protocol," 2004, 1-14, GIS Analysis protocol, Release NM091204.

Oren M. "Decision making by p53: life, death and cancer," Cell Death and Differentiation, 2003, 10:431-442.

Orlando V. et al. "Analysis of Chromatin Structure by in vivo formaldehyde cross-linking," Methods: A companion to methods in Enzymology, 1997, 11:205-214.

Peters B.A. and Velculescu V.E., "Transcriptome PETs: A genome's best friends," Nature Methods, 2005, 2 (2):93-94.

Ren B. et al. "Genome-wide location and function of DNA binding proteins," Science, 2000, 290:2306-2309.

Roulet E. et. al. "High-throughput SELEX-SAGE method for quantitative modeling of transcription-factor binding sites," Nature Biotechnology, 2002, 20:831-835.

Ruan Y. et. al. "Interrogating the transcriptome," Trends in Biotechnology, 2004, 22(1):23-30.

Shendure J. et. al. "Accurate multiplex polony sequencing of an evolved bacterial genome," Science, 2005, 309:1728-1732.

Velculescu V.E. et. al. "Serial analysis of gene expression," Science, 1995, 270(5235):484-487.

Yamamoto M. et. al. "Use of serial analysis of gene expression (SAGE) technology", Journal of Immunological Methods, 2001, 250:45-66.

Zhang Z. and Dietrich F.S., "Mapping of transcription start sites in Saccharomyces cerevisiae using 5' SAGE," Nucleic Acids Research, 2005, 33(9):2838-2851.

Visel, A. et al., "Genomic Views of Distant-Acting Enhancers" Nature, vol. 461:10, pp. 199-205, Sep. 2009.

* cited by examiner

FIGURE 11

```
        EcoRI           NotI                    EcoP15I

1   GGGCGAATTC GATATCGCGG CCGCGCCTGG ATAAAGTCAG CAGCTTCCAC GCCAGCTTCA CACAAAAAGT GACTGACGGT AGCCGCGCGG CGGTGCAGGA
      CCCGCTTAAG CTATAGCGCC GGCGCGGACC TATTTCAGTC GTCGAAGGTG CGGTCGAAGT GTGTTTTTCA CTGACTGCCA TCGGCGCGCC GCCACGTCCT
                                                                                BsmI

101  AGGTCAGGGC GATCTGTGGG TGAAACGTCC AAACTTATTC AACTGGCATA TGACACAACC TGATGAAAGC ATTCTGTTT CTGACGGTAA AACACTGTGG
      TCCAGTCCCG CTAGACACCC ACTTTGCAGG TTTGAATAAG TTGACCGTAT ACTGTGTTGG ACTACTTTCG TAAGACAAA GACTGCCATT TTGTGACACC

201  TTCTATAACC CGTTCGTTGA GCAAGCTACG GCAACCTGGC TGAAAGATGC CACCGGTAAT ACGCCGTTTA TGCTGATTGC CCGCAACCAG TCCAGCGACT
      AAGATATTGG GCAAGCAACT CGTTCGATGC CGTTGGACCG ACTTTCTACG GTGGCCATTA TGCGGCAAAT ACGACTAACG GGCGTTGGTC AGGTCGCTGA

EcoP15I

301  GGCAGCAGTA CAATATCAAA CAGAGATGGCG ATGACTTTGT CCTGACGCCG AAAGCCAGCA ATGGCAATCT GAAGCAGTTC ACCATTAACG TGGGACGTGA
      CCGTCGTCAT GTTATAGTTT GTCTTACCGC TACTGAAACA GGACTGCGGC TTTCGGTCGT TACCGTTAGA CTTCGTCAAG TGGTAATTGC ACCCTGCACT

401  TGGCACAATC CATCAGTTTA GCGCGGTGGA GCAGGACGAT CAGGCAGCA GTTATCAACT GAAATCCCAG CAAAATGGGG CTGTGGATGC AGCGAAATTT
      ACCGTGTTAG GTAGTCAAAT CGCGCCACCT CGGTCCTGCTA GTCGTCGT CAATAGTTGA CTTTAGGGTC GTTTTACCCC GACACCTACG TCGCTTTAAA

501  ACCTTCACCC CGCCGCAAGG CGTCACGGTA GATGATCAAC GTAAGTAGAG GCACCTGAGT GAGCAATCTG TCGCTCGATT TTTCGGATAA TACTTTTCAA
      TGGAAGTGGG GCGGCGTTCC GCAGTGCCAT CTACTAGTTG CATTCATCTC CGTGGACTCA CTCGTTAGAC AGCGAGCTAA AAAGCCTATT ATGAAAAGTT

601  CCTCTGGCCG CGCGTATGCG GCCAGAAAAT TTAGCACAGT ATATCGGCCA GCAACATTTG CTGGCTGCGG GGAAGCCGTT GCCGCGCGCT ATCGAGCCGG
      GGAGACCGGC GCGCATACGC CGGTCTTTTA AATCGTGTCA TATAGCCGGT CGTTGTAAAC GACCGACGCC CCTTCGGCAA CGGCGCGCGA TAGCTTCGGC
```

FIGURE 11 continued

```
701  GGCATTTACA TTCTATGATC CTCTGGGGGC CGCCGGGTAC CGGCAAAACA ACTCTCGCTG AAGTGATTGC CCGGCTATGCG AACGCTGATG TGGAACGTAT
     CCGTAAATGT AAGATACTAG GAGACCCCCG GCGGCCCATG GCCGTTTTGT TGAGAGCGAC TTCACTAACG GGCGATACGC TTGCGACTAC ACCTTGCATA
                                MmeI                                                BseRI
                    BamHI       XhoI       EcoRI        GsuI      BamHI

801  TTCTGCCGTA AGTCGAATTG GATCCGACTC GAGGATGAAT TCTCCAGGAT CCCTCCTCTG AGTATTCTAT AGTGTCACCT AAATAGCTTG GGCTAATCAT
     AAGACGGCAT TCAGCTTAAC CTAGGCTGAG CTCCTACTTA AGAGGTCCTA GGGAGGAGAC TCATAAGATA TCACAGTGGA TTTATCGAAC CGCATTAGTA

901  GGTCATAGCT GTTTCCTGTG TGAAATTGTT ATCCGCTCAC AATTCCACAC AACATACGAG CCGGAAGCAT AAAGTGTAAA CCGGACCCAG CCTAATGAGT
     CCAGTATCGA CAAAGGACAC ACTTTAACAA TAGGCGAGTG TTAAGGTGTG TTGTATGCTC GGCCTTCGTA TTTCACATTT GGCACCCCAC GGATTACTCA

1001 GAGCTAACTC ACATTAATTG CGTTGCGCTC ACTGCCCGCT TTCCAGTCGG GAAACCTGTC GTGCCAGCTG CATTAATGAA TCGGCCAACG CGCGGGAGA
     CTCGATTGAG TGTAATTAAC GCAACGCGAG TGACGGGCGA AAGGTCAGCC CACGGTCGAC GTACGGTTGC GCGCCCCTCT
1101 GGCGGTTTGC GTATTGGGCG CTCTTCCGCT TCCTCGCTCA CTGACTCGCT GCGCTCGGTC GTTCGGCTGC GGCGAGCGGT ATCAGCTCAC TCAAAGGCGG
1201 CCGCCAAACG CATAACCCGC GAGAAGGCGA AGGAGGCGAGT GACTGAGCGA CAACATGTGA GCAAAAGGCC AGGAACCGT CAGGAACCGT CGTTGCTGGC
1301 TAATACGGTT ATCCACAGAA TCAGGGGATA ACGCAGGAAA GAACATGTGA GCAAAAGGCC AGCAAAAGGC CAGGAACCGT AAAAAGGCCG CGTTGCTGGC
     ATTATGCCAA TAGGTGTCTT AGTCCCCTAT TGCGTCCTTT CTTGTACACT CAAGTCAGAG GTTCAGTCTC CGGATACCTG AGGCAAGCCC TTCGCACCGC GCAACGACCG
1401 GTTTTTCGAT AGGCTCCGCC CCCCTGACGA GCATCACAAA AATCGACGCT CAAGTCAGAG GTGGCGAAAC CCGACAGGAC TATAAAGATA CCAGGCGTTT
     CAAAAAGCTA TCCGAGGCGG GGGGACTGCT CGTAGTGTTT TTAGCTGCGA GTTCAGTCTC CACCGCTTTG GGCTGTCCTG ATATTTCTAT GGTCCGCAAA
     CCCCCTGGAA GCTCCCTCGT GCGCTCTCCT GTACCGACCC TGCCGCTTAC TCCGCCTTTC TCCCTTCGGG AAGCGTGGCG CTTTCTCATA
1501 GGGGGACCTT CGAGGGAGCA CGCGAGAGGA CATGGCTGGG ACGGCGAATG GCCTATGGAC AGGGAAGCCC TTCGCACCGC GAAAGAGTAT

1501 GCTCACGCTG TAGGTATCTC AGTTCGGTGT CTCCAAGCTG GGCTGTGTGC ACGAACCCCC CGTTCAGCCC GACCGCTGCG CCTTATCCGG
     CGAGTGCGAC ATCCATAGAG TCAAGCCACA GAGGTTCGAC CCGACACACG TGCTTGGGGG GCAAGTCGGG CTGGCGACGC GGAATAGGCC
     EcoP15I

1601 TAACTATCGT CTTGAGACCA ACCCGGTAAG ACACGACTTA TCGCCACTGG CAGCAGCCAC TGGTAACAGG ATTAGCAGAG CGAGGTATGT AGGCGGTGCT
     ATTGATAGCA GAACTCTGGT TGGGCCATTC TGTGCTGAAT AGCGGTGACC GTCGTCGGTG ACCATTGTCC TAATCGTCTC GCTCCATACA TCCGCCACGA
                                                                                              EcoP15I

1701 ACAGAGTTCT TGAAGTGGTG GCCTAACTAC GGCTACACTA GAAGGACAGT ATTTGGTATC TGCGCTCTGC TGAAGCCAGT TACCTTCGGA AAAAGAGTTG
     TGTCTCAAGA ACTTCACCAC CGGATTGATG CCGATGTGAT CTTCCTGTCA TAAACCATAG ACGCGAGACG ACTTCGGTCA ATGGAAGCCT TTTTCTCAAC
                                                                                         EcoP15I

1801 GTAGCTCTTG ATCCGGCAAA CAAACCACCG CTGGTAGCGG TGGTTTTTTT GTTTGCAAGC AGCAGATTAC GCGCAGAAAA AAAGGATCTC AAGAAGATCC
1901 CATCGAGAAC TAGGCCGTTT GTTTGGTGGC GACCATCGCC ACCAAAAAAA CAAACGTTCG TCGTCTAATG CGCGTCTTTT TTTCCTAGAG TTCTTCTAGG
2001 TTTGATCTTT TCTACGGGGT CTGACCGTCA GTGGAACGAA AACTCACGTT AAGGGATTTT GGTCATGAGA TTATCAAAAA GGATCTTCAC CTAGATCCTT
     AAACTAGAAA AGATGCCCCA GACTGGCAGT CACCTTGCTT TTGAGTGCAA TTCCCTAAAA CCAGTACTCT AATAGTTTTT CCTAGAAGTG GATCTAGGAA
     TTAAATTAAA AATGAAGTTT TAAATCAATC TAAAGTATAT ATGAGTAAAC TTGGTCTGAC AGTTACCAAT GCTTAATCAG TGAGGCACCT ATCTCAGCGA
```

FIGURE 11 continued

```
2101  TCTGTGTCTATT TCGTTCATCC ATAGTTGCCT GACTCCCGT CGTGTGAGATA ACTACGATAC GGGAGGGCTT ACCATCTGGC CCCAGTGCTG CAATGATACC
      AGACAGATAA AGCAAGTAGG TATCAACGGA CTGAGGGGCA GCACATCTAT TGATGCTATG CCCTCCCGAA TGGTAGACCG GGTCACGAC GTTACTATGG

2201  GCGAGACCCA CGCTCACCGG CTTCCGGATTT ATCAGCAATA AACCAGCCAG CCGGAAGGGC CGAGCGCAGA AGTGGTCCTG CAACTTTATC CGCCTCCATC
      CGCTCTGGGT GCGAGTGGCC GAGGCCTAAA TAGTCGTTAT TTGGTCGGTC GGCCTTCCCG GCTCGCGTCT TCACCAGGAC GTTGAAATAG GCGGAGGTAG

2301  CAGTCTATTA ATTGTTGCCG GGAAGCTAGA GTAAGTAGTT CGCCAGTTAA TAGTTGCGC AACGTTGTTG GCATTGCTAC AGCCATCGTG GTGTCACGCT
      GTCAGATAAT TAACAACGGC CCTTCGATCT CATTCATCAA GCGGTCAATT ATCAACGCG TTGCAACAAC CGTAACGATG TCCGTAGCAC CACAGTGCGA

2401  CGTCGTTTGG TATGGCTTCA TTCAGCTCCG GTTCCCAACG ATCAAGGCGA GTTACATGAT CCCCATGTT GTGCAAAAAA GCGGTTAGCT CCTTCGGTCC
      GCAGCAAACC ATACCGAAGT AAGTCGAGGC CAAGGGTTGC TAGTTCCGCT CAATGTACTA GGGGTACAA CACGTTTTTT CGCCAATGA GGAAGCCAGG

2501  TCCGATCGTT GTCAGAAGTA AGTTGGCCGC AGTGTTATCA CTCATGTTA TGGCAGCACT GCATAATTCT CTTACTGTCA TGCCATCCGT AAGATGCTTT
      AGGCTAGCAA CAGTCTTCAT TCAACCGGCG TCACAATAGT GAGTACATAG ACCGTCGTGA CGTATTAAGA GAATGACAGT ACGGTAGGCA TTCTACGAAA

2601  TCTGTGACTG GTGAGTACTC AACCAAGTCA TTCTGAGAAT AGTGTATGCG GCGACCGAGT TGCTCTTGCC CGGCGTCAAT ACGGGATAAT ACCGCGCCAC
      AGACACTGAC CACTCATGAG TTGGTTCAGT AAGACTCTTA TCACATACGC CGCTGGCTCA ACGAGAACGG GCCGCAGTTA TGCCCTATTA TGGCGCGGTG

2701  ATAGCAGAAC TTTAAAAGTG CTCATCATTG GAAAACGTTC TTCGGGGCGA AAACTCTCAA GATCTTACC GCTGTTGAGA TCCAGTTCGA TGTAACCCAC
      TATCGTCTTG AAATTTTCAC GAGTAGTAAC CTTTTGCAAG AAGCCCCGCT TTTGAGAGTT CCTAGAGTG CGACAACTCT AGGTCAAGCT ACATTGGGTG

2801  TCGTGCACCC AACTGATCTT CAGCATCTTT TACTTTCACC AGCGTTTCTG GGTGAGCAAA AACAGGAAGG CAAAATGCCG CAAAAAAGGG AATAAGGCG
      AGCACGTGGG TTGACTAGAA GTCGTAGAAA ATGAAAGTGG TCGCAAAGAC CCACTCGTTT TTGTCCTTCC GTTTTACGGC GTTTTTTCCC TTATTCCCGC

2901  ACACGGAAAT GTTGAATACT CATACTCTTC CTTTTTTCAT ATTATTGAAG CATTTATCAG GGTTATTGTC TCATGAGCGG ATACATATTT GAATGTATTT
      TGTGCCTTTA CAACTTATGA GTATGAGAAG GAAAAAGTTA TAATAACTTC GTAAATAGTC CCAATAACAG AGTACTCGCC TATGTATAAA CTTACATAAA
                                                                ZraI

3001  AGAAAAATAA ACAAATAGGG GTTCCGCGCA CATTTCCCCG AAAAAGTGCCA CCTGACGTCT AAGAAACCAT TATTATCATG ACATTAACCT ATAAAAATAG
      TCTTTTTATT TGTTTATCCC CAAGGCGCGT GTAAAGGGGC TTTTCACGGT GGACTGCAGA TTCTTTGGTA ATAATAGTAC TGTAATTGGA TATTTTTATC

3101  GGGTATCACG AGGCCCTTTC GTCTCGCGCG TTTCGGTGAT GACGGTGAAA ACCTTCTGACA CATGCAGCTC CCGGAGACGG TCACAGCTTG TCTGTAAGCG
      CCGATATGC TCCGGGAAAG CAGAGCGCGC AAAGCCACTA CTGCCACTTT TGGAGACTGT GTACGTCGAG GGCCTCTGCC AGTGTCGAAC AGACATTCGC

3201  GATGCCGGGA GCAGACAAGC CCGTCAGGGC GCGTCAGCGG GTGTTGGCGG GTGTCGGGGC TGGCTTAACT ATGCGGCATC AGAGCAGATT GTACTGAGAG
      CTACGGCCCT CGTCTGTTCG GGCAGTCCCG CGCAGTCGCC CACAACCGCC CACAGCCCCG ACCGAATTGA TACGCCGTAG TCTCGTCTAA CATGACTCTC
```

FIGURE 11 continued

```
3301   TGCACCATAT GCGGTGTGAA ATACCGCACA GATGCGTAAG GAGAAAATAC CGCATCAGGC GCCATTCGCC ATTCAGGCTG CGCAACTGTT GGGAAGGGCG
       ACGTGGTATA CGCCACACTT TATGGCGTGT CTACGCATTC CTCTTTTATG GCGTAGTCCG CGGTAAGCGG TAAGTCCGAC GCGTTGACAA CCCTTCCCGC

3401   ATCGGTGCGG GCCTCTTCGC TATTACGCCA GCTGGCGAAA GGGGGATGTG CTGCAAGGCG ATTAAGTTGG GTAACGCCAG GGTTTTCCCA GTCACGACGT
       TAGCCACGCC CGGAGAAGCG ATAATGCGGT CGACCGCTTT CCCCCTACAC GACGTTCCGC TAATTCAACC CATTGCGGTC CCAAAAGGGT CAGTGCTGCA

3501   TGTAAAACGA CGGCCAGTGA ATTGTAATAC GACTCACTAT A
       ACATTTTGCT GCCGGTCACT TAACATTATG CTGAGTGATA T
```

NUCLEIC ACID INTERACTION ANALYSIS

FIELD OF THE INVENTION

The present invention generally relates to the field of gene expression. More specifically, the present invention relates to nucleic acid interactions. In particular, the invention relates to analysis, detection and identification of nucleic acid-protein interaction events and components

BACKGROUND OF THE INVENTION

Chromatin interaction is important in gene regulation. The recently completed human genome sequences provide frameworks of genetic information. However, the human genome structure and information is often presented as a one-dimensional linearity, which is short to explain the complexity and coordination of a cellular system. An entirely different perspective is required for understanding how a genome actually functions as an orchestrated system in a three-dimensional nucleus in living cells. Genomic DNA (estimated to be two meters long stretched out) is condensed in chromosomes only a few microns across in a nucleus. It is known that chromosomes are unevenly organized into euchromatins and heterochromatins, which are packaged by chromatin proteins and communicated by transcription factors for transcription and replication.

These activities appear to be ordered. It has been observed that large chromosomal loops contain active genes. Furthermore, it has been suggested that distal regulatory elements such as locus control regions (LCR), enhancers, and insulators act by repositioning specific genetic loci to regions with active or silent transcription. Recent work has demonstrated in β-globin, and most recently, in cytokine gene (IFN-γ) that LCRs may directly interact with promoters in long distances on the same chromosome and even interact with promoters on different chromosomes. It is possible that intra- and inter-chromosomal interactions are general phenomena occurring at multiple genetic loci in coordinating gene regulation of important pathways. Inter-chromosomal interactions have also been implicated in diseases. For example, dysregulation of myc transcript is achieved by chromosomal translocations that juxtapose the c-myc/pvt-1 locus on chromosome 15 with one of the immunoglobulin loci on chromosome 12. Further analysis of interchromosomal interactions at whole genome level is necessary to identify all interactions, and will shed light on high-order gene regulations in cells.

Technologies used for studies of chromatin interactions—A number of approaches have been used to study the three-dimensional structure and chromatin interactions, all with considerable limitations. Technologies applicable to this question may be roughly classified as visualization tools, such as microscopy, Fluorescence In Situ hybridization (FISH), and RNA-TRAP (RNA Tagging and Recovery of Associated Proteins); and molecular methodologies, such as chromosome conformation capture (3C), and 3C followed by chromatin immunoprecipitation (3C-ChIP).

Microscopy was used in many early studies to investigate chromatin spatial organization in nuclei. However, such cytogenetic approach may only provide rough segment information of chromatins in chromosomes. FISH is a significant improvement in this direction, which localizes specific genetic loci to particular physical locations on chromosomes through fluorescence labelled DNA or RNA probes hybridizing to genomic DNA. However, the resolution was very still limited. Modified from FISH, RNA-TRAP is a method that may show distal enhancers in close physical proximity with gene promoters.

Chromosome Conformation Capture (3C) was originally designed to investigate chromosomal conformation in yeast (Dekker et al, 2002), and has been used to study interactions of genetic elements that are separated in long distance and/or in different chromosomes. In 3C, DNA-protein (chromatin) structures are formaldehyde cross-linked in vivo, and chromatins are fragmented by restriction enzyme digestion. DNA fragments tethered by DNA binding proteins are then joined together by ligation, and the junctions of two suspected known elements are detected by PCR. The detection of chromatin interactions mediated by specific DNA binding protein or transcription factors may be further enhanced by chromatin immunoprecipitation (3C-ChIP), in which the chimerical DNA fragments cross-linked with protein resulted in the 3C procedure are enriched by antibody pull-down.

Though each individual technique and some combinations have been demonstrated to be useful in identifying some specific intra- and inter-chromosomal interactions, these approaches relied on existing knowledge or conjecture as to what possible distal chromatin interactions may be present and primers designed to detect such junctions by PCR one region at a time. Therefore, the current technologies for study of chromatin interactions are extremely limited for identification of novel chromatin interactions and large scale at whole genome level.

Despite considerable interest in the way that chromosomes are spatially organized within the nucleus and how that may regulate transcription of distal genes in concert, only scattered and indirect information is currently available. The lack of information in this aspect is largely due to the lack of robust technologies that may effectively address three-dimensional questions of chromosomal interactions.

There is a need in the art for more efficient methods and robust technologies that may effectively address three-dimensional questions of chromosomal interactions that may overcome the disadvantages and limitations of the existing art.

SUMMARY OF THE INVENTION

The present invention solves the problems mentioned above by providing a new method of detecting, identifying and/or preparing at least one nucleic acid sequence or fragment from a nucleic acid complex, in particular from a nucleic acid-protein complex. In particular, the method according to the invention provides a method of detecting, identifying and/or preparing at least two nucleic acid sequences or fragments from a nucleic acid-protein complex. The present invention also relates to oligonucleotides prepared with a method according to any embodiment of the invention. There is also provided a method to identify chromatin interaction events mediated by specific DNA binding proteins across long distances and between different chromosomes.

In another aspect, the present invention solves the problem mentioned above by providing an isolated oligonucleotide comprising at least one first tag and at least one second tag, wherein the first and second tags are tags of a nucleic acid-protein complex. In particular, there is provided an isolated oligonucleotide comprising at least one first tag and at least one second tag, wherein the first tag is obtained from a first polynucleotide and the second tag obtained from a second polynucleotide, the first and second polynucleotides obtained from a nucleic acid-protein complex. The first and second polynucleotides may be part of the same nucleic acid region or from different nucleic acid regions of the nucleic acid-protein complex.

The isolated oligonucleotide may further comprise at least one restriction enzyme recognition site at least one linker. In particular, the at least one restriction enzyme recognition site may be included in a linker. The linker may be inserted between the tags or the linker may flank at least one tag (that is, positioned upstream and/or downstream to at least one tag). The at least one restriction enzyme recognition site may be asymmetric. The at least one restriction enzyme recognition site may be, for example, for a type IIs restriction enzyme or for a homing restriction enzyme.

The at least one first tag may comprise a 5' terminus and a 3' terminus from the first polynucleotide and the at least one second tag comprises a 5' terminus and a 3' terminus from the second polynucleotide. The isolated oligonucleotide may further comprise at least one linker. The linker may be inserted between the tags or the linker may positioned upstream and/or downstream to at least one tag. The linker comprises at least one restriction enzyme recognition site. The at least one restriction enzyme recognition site may be asymmetric. The at least one restriction enzyme recognition site may be, for example, for a type IIs restriction enzyme or for a homing restriction enzyme.

The linker may comprise a first restriction recognition site recognized by a restriction enzyme capable of cleaving the first polynucleotide to obtain the first tag, and a second restriction recognition site recognized by a restriction enzyme capable of cleaving the second polynucleotide to obtain the second tag. In particular, the linker may comprise a first restriction recognition site recognized by a restriction enzyme capable of cleaving the first polynucleotide to obtain a 3' terminus of the first polynucleotide, and a second restriction recognition site recognized by a second restriction enzyme capable of cleaving the second polynucleotide to obtain a 5' terminus of the second polynucleotide. The first and second restriction recognition sites may be recognized by the same or different restriction enzyme.

According to another aspect, the first polynucleotide may be further cleaved by a third restriction enzyme recognizing a third recognition site to obtain a 5' terminus of the first polynucleotide, and the second polynucleotide is cleaved by a fourth restriction enzyme recognizing a fourth recognition site to obtain a 3' terminus of the second polynucleotide. According to this embodiment, at least one first tag is obtained from ligating the 5' and 3' termini of the first polynucleotide and at least one second tag is obtained from ligating the 5' and 3' termini of the second polynucleotide. The third and fourth recognition sites may be recognized by the same or different restriction enzymes. The further recognition sites may be included in adaptors ligated to the 5' end of the first polynucleotide and to the 3' end of the second polynucleotide, respectively. Alternatively, the third and fourth restriction sites may be present in a vector into which the structure first polynucleotide-linker-second polynucleotide is inserted. In this case, the third restriction site flanks the 5' end of the first polynucleotide and the fourth restriction site flanks the 3' end of the second polynucleotide.

The nucleic acid-protein complex of the isolated oligonucleotide may be part of a chromatin structure. The nucleic acid fragment to which a protein of interest binds may be any nucleic acid fragment comprising a region to which a protein of interest binds, for example, histone binding site. The polynucleotides may be DNA or RNA.

In another aspect, the present invention provides a concatemer of oligonucleotides comprising at least two isolated oligonucleotides, each isolated oligonucleotide comprising at least one first tag and at least one second tag, wherein the first and second tags are tags of a nucleic acid-protein complex. IN particular, there is provided a concatemer of oligonucleotides comprising at least two isolated oligonucleotides, each isolated oligonucleotide comprising at least one first tag and at least one second tag, wherein the first tag is a tag of a first polynucleotide and the second tag is a tag of a second polynucleotide, the first and second polynucleotides are from a nucleic acid-protein complex. The concatemer may further comprise at least one linker. The linker may comprise at least one restriction enzyme recognition site. Further, each isolated oligonucleotide of the concatemer may comprise at least one restriction enzyme recognition site. The at least one restriction enzyme recognition site may be comprised in at least one linker and/or in at least one adapter.

The linker may be inserted between the tags or the linker may positioned upstream and/or downstream to at least one tag. The linker may comprise at least one restriction enzyme recognition site. The at least one restriction enzyme recognition site may be for a type IIs restriction enzyme or for a homing restriction enzyme. The first tag of each oligonucleotide of the concatemer may comprise a 5' terminus and a 3' terminus from the first polynucleotide, and the second tag may comprise a 5' terminus and a 3' terminus from the second polynucleotide.

The oligonucleotide or the concatemer according to the invention may be inserted into a vector and/or a cell. The cell may be a bacterial cell.

The polynucleotide nucleic acid-protein complex may be part of a chromatin structure The polynucleotides may be located on the same chromosome or may be located on different chromosomes.

In another aspect, the present invention provides a library of oligonucleotides or concatemer of oligonucleotides comprising at least one oligonucleotide, the oligonucleotide comprising at least one first tag and at least one second tag, wherein the first tag is obtained from a first polynucleotide and the second tag obtained from a second polynucleotide, the first and second polynucleotides obtained from a nucleic acid-protein complex.

The at least one oligonucleotide of the library may comprise at least one linker. The linker may be inserted between the tags or the linker may positioned upstream and/or downstream to at least one tag. The first tag may comprise a 5' terminus and a 3' terminus from the first polynucleotide and the second tag further comprises a 5' terminus and a 3' terminus from the second polynucleotide.

In another aspect, the present invention provides a method of preparing at least one isolated oligonucleotide comprising:
   (a) providing a nucleic acid-protein complex;
   (b) preparing an oligonucleotide comprising at least one first tag and at least one second tag, wherein the first and second tags are obtained from a nucleic acid-protein complex; and
   (c) isolating the oligonucleotide.

In particular, the present invention provides a method of preparing at least one isolated oligonucleotide comprising:
(a) providing a nucleic acid-protein complex;
(b) preparing an oligonucleotide comprising at least one first tag and at least one second tag, wherein the first tag is obtained from a first polynucleotide and the second tag obtained from a second polynucleotide, the first and second polynucleotides obtained from a nucleic acid-protein complex; and
(c) isolating the oligonucleotide.

In one embodiment, step (b) of this aspect of the invention comprises:
(i) inserting at least one linker comprising at least one restriction enzyme recognition site, and
(ii) cleaving the first and second polynucleotides with a least one restriction enzyme recognizing the at least one recognition site in the linker to form an oligonucleotide comprising a first tag obtained from the first polynucleotide, a second tag obtained from the second polynucleotide and the linker between the tags.

In another embodiment, step (b) of this aspect of the invention comprises:
(i) inserting at least one linker comprising at least one restriction enzyme recognition site between the first polynucleotide and the second polynucleotide of the complex;
(ii) adding at least one restriction enzyme recognition site to the 5' terminus of the first polynucleotide and to the 3' terminus of the second polynucleotide;
(iii) cleaving the first and second polynucleotides with at least one restriction enzyme recognizing at least one recognition site to obtain cleaved fragments; and
(iv) ligating cleaved fragments to form the oligonucleotide comprising a first tag obtained from the first polynucleotide, a second tag obtained from the second polynucleotide, the tags comprising 5' and 3' termini of each polynucleotide, and the linker inserted between the tags and the at least one restriction enzyme recognition site in step (ii) is part of an adaptor or part of a vector.

The polynucleotides may be obtained from the nucleic acid-protein complex by incorporating a photoactivatable moiety into the nucleic acid (for example, DNA) and/or the protein of interest and isolation of nucleic acid/protein complex by antibody-mediated precipitation or by affinity-mediated technique. Examples of such affinity-based techniques include streptavidin/biotin, Glutathione-S-transferase/glutatathione matrix, maltose-binding protein/amylose matrix interactions.

In another aspect, the present invention provides a method of detecting and/or identifying at least two polynucleotides from a nucleic acid-protein complex, the method comprising:
(a) providing a nucleic acid-protein complex;
(b) preparing an oligonucleotide comprising at least one first tag and at least one second tag, wherein the first tag is obtained from a first polynucleotide and the second tag obtained from a second polynucleotide, the first and second polynucleotides obtained from a nucleic acid-protein complex;
(c) sequencing the oligonucleotide; and
(d) mapping the at least two polynucleotides based on the nucleotide sequences of the first and second tags, thereby detecting and/or identifying the at least two polynucleotides.

The oligonucleotide obtained in step (b) may be amplified before being sequenced in step (c). The amplification may be by polymerase chain reaction. The amplified oligonucleotides may be subjected to at least one purification step after amplification but before being sequenced in step (c). The at least one purification step is may be gel electrophoresis.

The oligonucleotide according to the invention may be concatenated with at least one further oligonucleotide obtained by steps (a) to (b) before being sequenced.

The sequencing may be carried out by the Sanger method or by multiplex sequencing such as pyrosequencing.

The detecting and/or identifying may be for transfusion or translocation of the polynucleotides. Accordingly, the method may be used to detect and/or identifying polynucleotides and/or genes in proximity with each other in nucleic acid-protein complexes such as those in chromatin. In addition, the nucleic acid fragment to which a protein of interest binds may be any nucleic acid fragment comprising a region to which a protein of interest binds, for example, histone binding site. The polynucleotides may be DNA or RNA.

The oligonucleotide may be transfected into at least one cell. The transfection may be by electroporation. The cell may be a bacterial cell. The polynucleotides may be DNA or RNA.

In another aspect, the present invention provides a vector comprising the oligonucleotide, the concatemer of oligonucleotides or the library of oligonucleotides or concatemers.

BRIEF DESCRIPTION OF THE DRAWINGS

FIG. 11 shows the nucleic acid sequence of the vector pGIS8 used in the examples with the various restriction enzyme recognistion sites indicated. The sequences appear as SEQ ID NO:18 and SEQ ID NO:19 in the sequence listing.

DETAILED DESCRIPTION OF THE INVENTION

Figure 1:
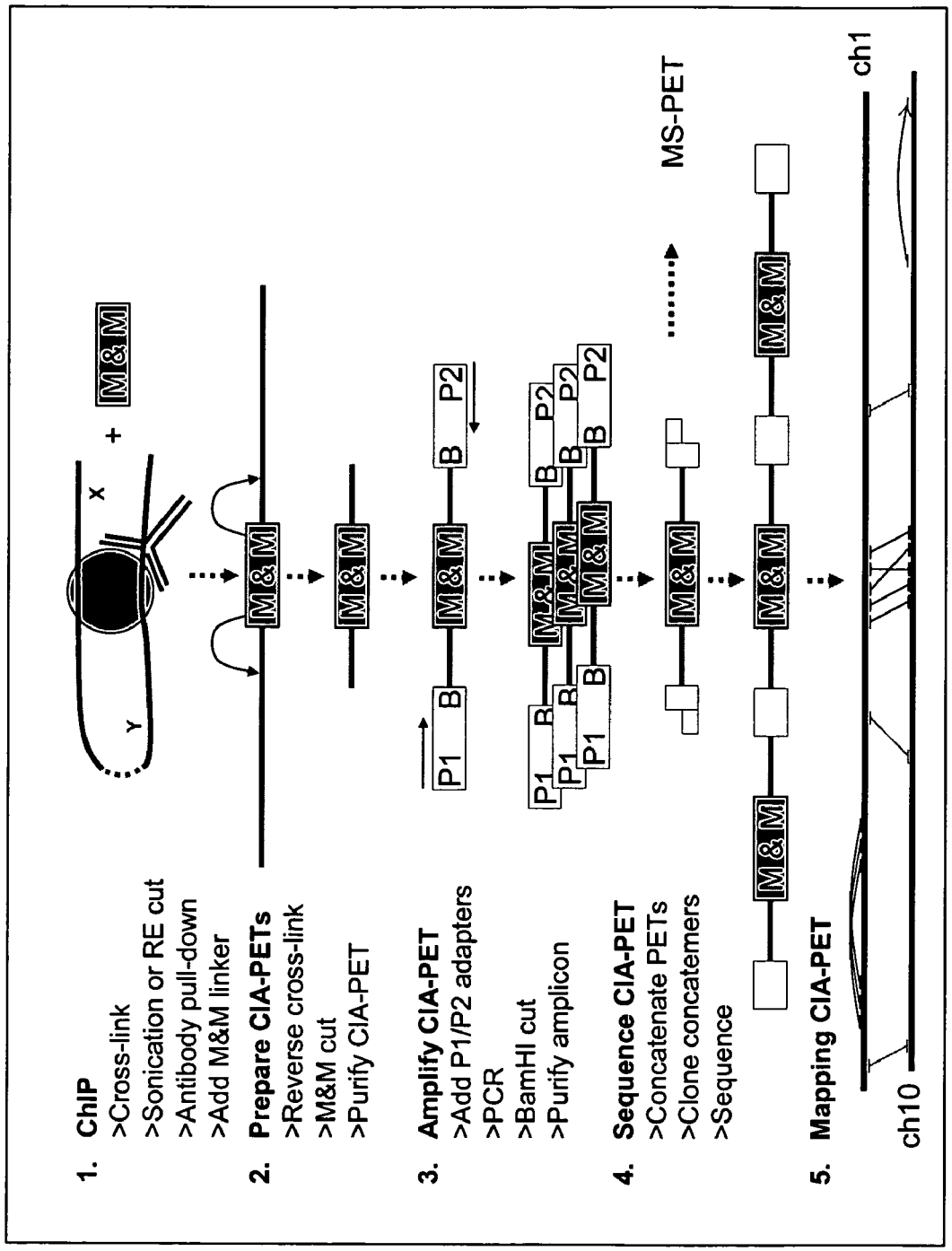
FIG. 1 illustrates the overview of one method of the present invention for Chromatin Interaction Analysis by paired end (di)tag(s) (CIA-PET) sequencing.

Definitions.

Restriction enzyme—A restriction enzyme (or restriction endonuclease) is an enzyme that cuts double-stranded DNA. The enzyme makes two incisions, one through each of the phosphate backbones of the double helix without damaging the bases. The chemical bonds that the enzymes cleave may be reformed by other enzymes known as ligases so that restriction fragments obtained from different chromosomes or genes may be spliced together, provided their ends are complementary. Type II enzymes recognized specific nucleic sequences and cut DNA at defined positions close to or within their recognition sequences sites. They produce discrete restriction fragments and distinct gel banding patterns. Type IIs enzymes cleave outside of their recognition sequence to one side. MmeI as well as most of the type IIs restriction enzymes produce variable end lengths (Dunn et al, 2002 showed that MmeI can cut 18/20 or 19/21 bases away in a rough proportion of 1:1. Therefore, the sequences given in all figures each represent one common variant of the use of MmeI.

The PET intermediates also have variable lengths (that is, M and G adapter DNA sequences after cloning into pGIS8 plasmids and M PET intermediate), because the polynucleotide can be of differing lengths. Type III enzymes are also large combination restriction-and-modification enzymes. They cleave outside of their recognition sequences and require two such sequences in opposite orientations within the same DNA molecule to accomplish cleavage. Homing endonucleases are rare double-stranded DNases that have large, asymmetric recognition sites (1240 base pairs) and coding sequences that are usually embedded in either introns (DNA) or inteins (proteins). Restriction enzymes may make cuts that leave either blunt end or sticky ends with overhangs. A sticky-end fragment can be ligated not only to the fragment from which it was originally cleaved, but also to any other fragment with a compatible cohesive or sticky end. As such, ends produced by different enzymes may also be compatible. A sticky end can thus be also referred as an end capable of being ligated. Many type II restriction enzymes cut palindromic DNA sequences. If a restriction enzyme has a non-degenerate palindromic cleavage site, all ends that it produces are compatible. A "palindromic" sequence is one where the sequence on one strand reads the same in the opposite direction on the complementary strand. As such, it is possible for nucleic acid strands treated to obtain palindromic cohesive ends to have its ends mate and the nucleic acid strands to self-circularize. The meaning of "palindromic" in this context is different from its linguistic usage. For example, the sequence GTAATG is not a palindromic DNA sequence, while the sequence GTATAC is. Examples of restriction enzymes leaving cohesive or sticky ends include BamH1, EcoR1 and HindIII. Examples of restriction enzymes leaving blunt, non-cohesive or non-sticky ends include BseR1 and AluI.

Nucleotide—a phosphoric ester of nucleoside; the basic structural unit of nucleic acids (DNA or RNA). Nucleotides form base pairs—one of the pairs of chemical bases joined by hydrogen bonds that connect the complementary strands of a DNA molecule or of an RNA molecule that has two strands; the base pairs are adenine with thymine and guanine with cytosine in DNA and adenine with uracil and guanine with cytosine in RNA. Short strands of nucleotides are referred to as oligonucleotides; longer strands are referred to as polynucleotides. Nucleotides may be joined with or concatenated with other nucleotides. The term nucleotide may be used interchangeably with the term nucleic acid. A stretch of nucleic acids possess a 5' end and a 3' end. The end regions of a stretch of nucleic acid may be referred to as the 5' terminus and the 3' terminus respectively. With 5' or 3' terminus of a polynucleotide, it is understood any region, fragment or whole piece of a polynucleotide that comprises the actual 5' or 3' terminus of the polynucleotide are included.

Concatemer—It is composed by at least two nucleotide monomers sequences linked end to end, optionally separated by a linker or spacer. For the purpose of the present invention, a concatemer comprises at least two oligonucleotides prepared according to the method of the invention.

Clone, cloning—To transfer nucleotides, such as a gene from one organism to another and/or to replicated the nucleotide by genetic engineering techniques.

Library—a collection of cloned nucleic acid sequences, oligonucleotides or polynucleotides, usually comprised in one or more plasmids.

Vector—A bacteriophage, plasmid, or other agent that transfers genetic material from one cell to another.

Obtain, derive—to use molecular biology and genetic engineering and manipulation techniques on biological material such as nucleic acids and proteins to confer upon the material certain desired characteristics. The terms obtain and derive may be used interchangeably under the present invention.

Amplification—increasing the copy number of nucleic acids. One method commonly used is that of polymerase chain reaction (PCR). Other amplification methods known to a skilled person may also be used.

Transfection or transformation—any method for introducing foreign molecules into a cell. Lipofection, calcium phosphate precipitation, retroviral deliver, electoporation and biolistic transformation are just a few of the teachings that may be used.

Chromatin—A complex of nucleic acids and proteins, primarily histones, in the cell nucleus that stains readily with basic dyes and condenses to form chromosomes during cell division. Chromatin is an example of a nucleic acid-protein complex. Regions of chromosomes may interact with other regions either on the same or different chromosome. The interaction event may thus be an inter- or intra-chromosomal event and may involve rearrangement of the genetic material at the regions involved.

Transfusion—rearrangement of genetic information at the RNA processing level to form a new chimerical transcript.

Translocation—rearrangement of genetic information at the genomic DNA level.

Nucleic acid-protein complex—an interaction of genetic material and a protein such as that found in chromatin or when a transcription factor binds to stretch of nucleic acid. A DNA-protein-DNA (DPD) complex is a more specific structure wherein a protein binds between two stretches of nucleic acid (DNA) of interest. A stretch of nucleic acid such as DNA may be manipulated to become a tag or an identifiable sequence of DNA.

Tag, tag-linker structure—A tag or signature is an identifiable sequence of nucleic acids refers to either the 5'- or 3'-most terminal nucleic acid sequence (terminus; usually 18-20 bp) derived from any contiguous DNA region, or a tag may comprise both the 5' and 3' most terminal nucleic acid sequences or termini of any contiguous DNA region. A linker is an artificial sequence of nucleic acids. The tag-linker-tag structure is thus an arrangement of nucleic acids wherein a linker is inserted between two tags. Another possible arrangement is a linker-tag-tag-linker structure where a linker flanks a tag (that is, it is positioned upstream and/or downstream to at least one of the tag). The terms tag and signature may be used interchangeably under the present invention.

Ditag—A short (usually 12-60 bp) nucleic acid fragment derived terminal tags or signatures of polynucleotides. A ditag may be prepared according to US 20050255501 and/or US 20050059022, the contents of which are herein incorporated by reference.

Sequencing—The methods used to determine the order of constituents in a biopolymer, in this case, a nucleic acid. Sequencing techniques used include Sanger method and modified variations thereof, as well as pyrosequencing or the "454 method" of sequencing.

In the following description, details and specific quantities and parameters are provided to describe the embodiments of the present invention. It shall be apparent to one skilled in the art, however that the invention may be practiced without such details. Some of the details may not be described at length so as not to obscure the invention.

For the performance of the methods of the present invention for a particular embodiment, any description disclosed for the purpose of carrying out other embodiments of this invention may also be used and are herein incorporated by reference. In particular, technique(s), reagents, experimental conditions, restrictions sites, enzymes, vectors, primers, and the like. In particular, it will be evident to any skilled person how to adapt techniques and material disclosed for the other embodiments to the present embodiment of the invention.

A person skilled in the art will appreciate that techniques not specifically taught herein may be found in standard molecular biology reference books such as Molecular Cloning: A Laboratory Manual by Sambrook and Russell, Third Edition, 2001, published by Cold Spring Harbor Laboratory Press.

Description

The present invention relates to a new method of detecting, identifying and/or preparing at least one nucleic acid sequence or fragment from a nucleic acid complex, in particular from a nucleic acid-protein complex. In particular, the method according to the invention provides a method of detecting, identifying and/or preparing at least two nucleic acid sequences or fragments from a nucleic acid-protein complex. The invention also provides for oligonucleotides and/or concatamers of oligonucleotides.

According to one aspect, the present invention provides a method for chromatin interaction analysis (CIA). The CIA is designed to capture novel information about distal control regions and inter-chromosomal interactions de novo. This method is designed to identify chromatin interaction events mediated by specific DNA binding proteins, such as histones, across long distances and between different chromosomes.

Figure 2:
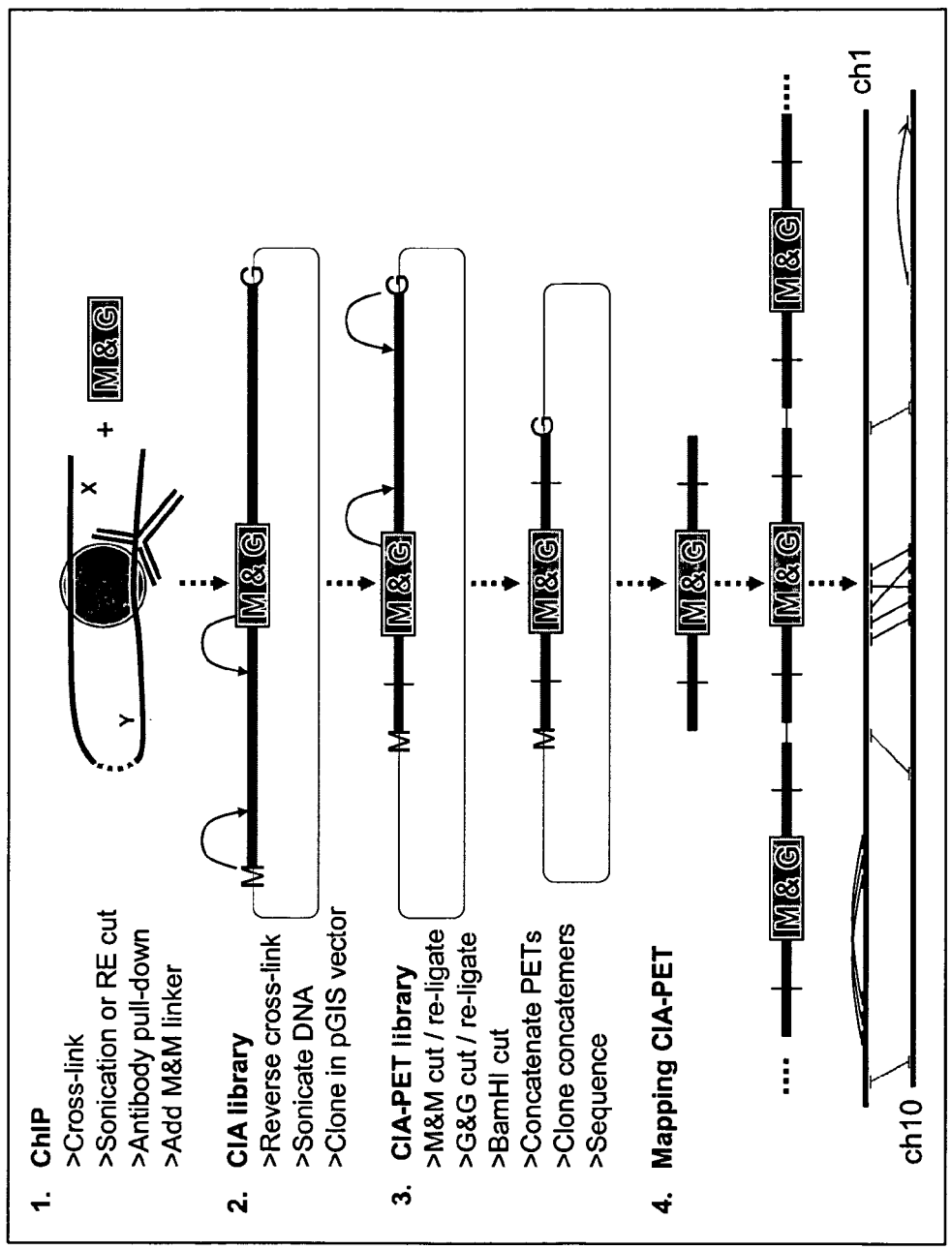
FIG. 2 illustrates the overview of another method of the present invention for CIA-diPET method.

Two embodiments of the CIA method are provided under the present invention to detect such DNA junctions, namely the CIA-PET method that extracts a single tag signature (about 20 bp) from each of the two ligated DNA fragments to form a "tag1-linker-tag2" (also referred to as "first tag-linker-second tag) paired end ditag (PET) structure (FIG. 1), and the CIA-diPET method that obtains two paired end ditags (PET) to represent the two related DNA fragments in a structure of "PET1-linker-PET2", so called diPET (FIG. 2). The tags of CIA-PET and CIA-diPET may be directly sequenced a multiplex sequencing technique such as the "454" pyrosequencing method, or concatenated for cloning and sequencing using conventional sequencing method.

Accordingly, the present invention provides a method of preparing at least one isolated oligonucleotide comprising:
(a) providing a nucleic acid-protein complex;
(b) preparing an oligonucleotide comprising at least one first tag and at least one second tag, wherein the first and second tags are obtained from a nucleic acid-protein complex; and
(c) isolating the oligonucleotide.

The first tag may be obtained from a first polynucleotide and the second tag is obtained from a second polynucleotide, the first and second polynucleotides obtained from a nucleic acid-protein complex.

The step (b) may comprise:
(i) inserting at least one linker comprising at least one restriction enzyme recognition site, and
(ii) cleaving the first and second polynucleotides with a least one restriction enzyme recognizing the at least one recognition site in the linker to form an oligonucleotide comprising a first tag obtained from the first polynucleotide, a second tag obtained from the second polynucleotide and the linker.

In particular, step (b) may comprise:
(i) inserting at least one linker comprising at least one restriction enzyme recognition site between the first polynucleotide and the second polynucleotide of the complex;
(ii) adding at least one restriction enzyme recognition site each to the 5' terminus of the first polynucleotide and the 3' terminus of the second polynucleotide;
(iii) cleaving the first and second polynucleotides with at least one restriction enzyme recognizing at least one recognition site to obtain cleaved fragments; and
(iv) ligating cleaved fragments to form the oligonucleotide comprising a first tag obtained from the first polynucleotide, a second tag obtained from the second polynucleotide, the tags comprising 5' and 3' termini of each polynucleotide, and the linker inserted between the tags.

The present invention also provides a method of detecting and/or identifying at least two polynucleotides from a nucleic acid-protein complex, the method comprising:
(a) providing a nucleic acid-protein complex;
(b) preparing an oligonucleotide comprising at least one first tag and at least one second tag, wherein the first tag is obtained from a first polynucleotide and the second tag obtained from a second polynucleotide, the first and second polynucleotides obtained from a nucleic acid-protein complex;
(c) sequencing the oligonucleotide; and
(d) mapping the at least two polynucleotides based on the sequence, thereby detecting and/or identifying the at least two polynucleotides.

As the linker sequence carries two Type II restriction enzyme recognition sites at each end (FIGS. 2 and 4), therefore, after a Type II restriction digestion, one tag sequence signature each (about 20 bp) may be excised from the two linked DNA fragments, to form a tag-linker-tag structure, in which one tag represents one DNA region of a chromosome while the other tag represents a locus from a far away region on the same or in different chromosome. This paired end ditag structure is referred to as "CIA-PET", which may be efficiently sequenced through concatenation into longer stretch of DNA or directly analyzed by sequencing.

Alternatively, linker sequences may flank the two tags to yield a linker-tag-tag-linker structure.

In this method, the nucleic acid-protein complexes, such as native DNA-protein-DNA (DPD) complexes, are cross-linked by a suitable fixative such as formaldehyde, glutaldehyde or methonaol. The cross-linked DPD complex may then be fragmented by sonication, hydroshearing (Hydroshear, Gene Machines), repeated drawing through a hypodermic syringe needle or by restriction enzyme digestion. The DNA fragments originated from different chromosomes or at long distance are tethered by DNA binding proteins in the DPD complexes. Unlike the 3C technique that requires existing knowledge or conjecture as to what these DNA fragments are so as to generate PCR primers, the ends of DNA fragments with distal relationship bounded in a DPD complex are joined by specific linker through ligation.

The linker (about 20 bp) contains two Type II restriction enzyme recognition sites to join the ends of different DNA fragments tethered by proteins in each DPD complex. The DNA junction of the two related DNA fragments may then be tagged by the paired end ditagging (PET) strategy (US 20050255501). Type IIs restriction enzyme recognitions sites are preferred. Besides Type II restriction enzymes, any other suitable restriction enzyme, including Type III or homing restriction enzymes may be used.

Figure 3:
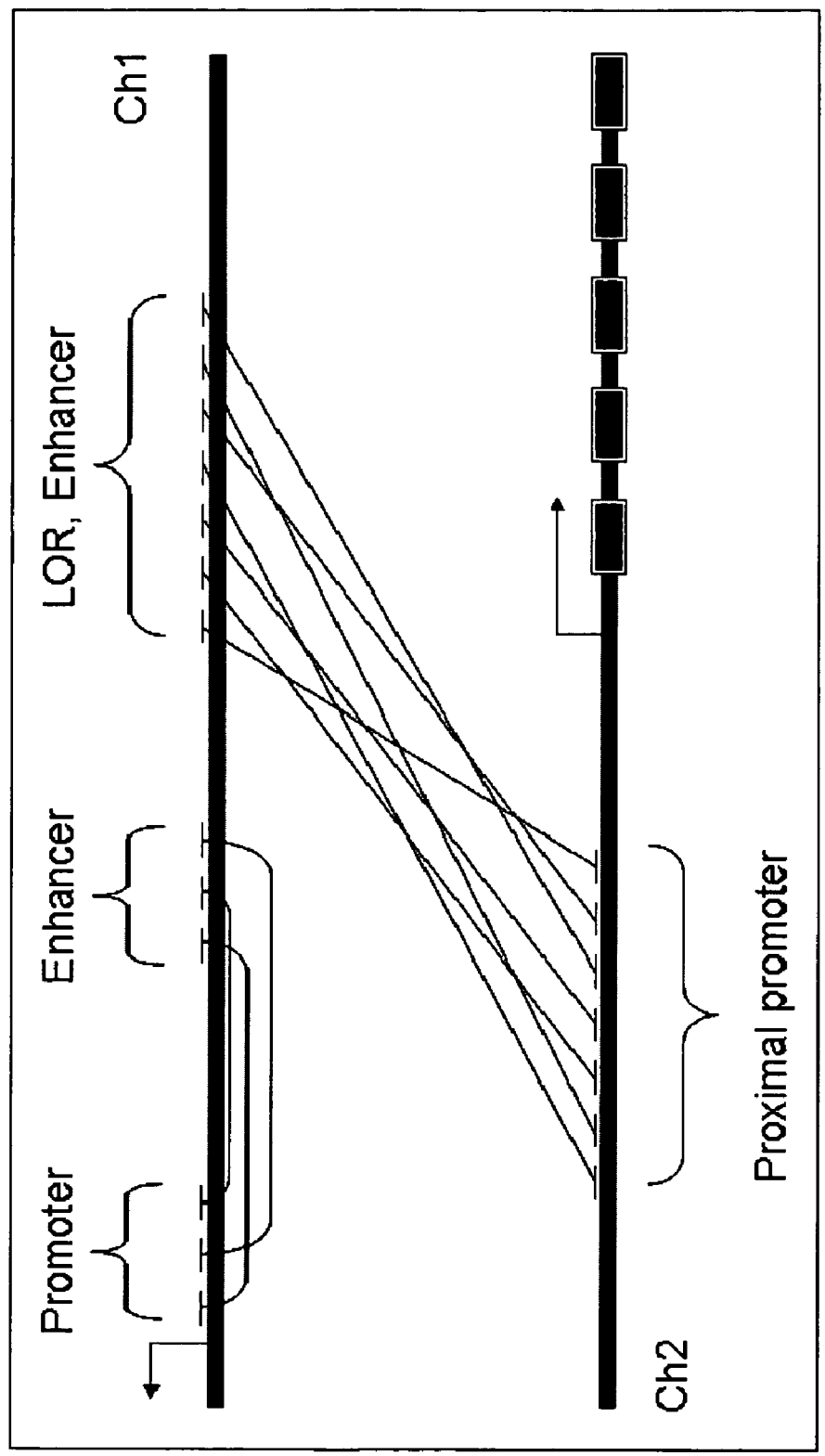
FIG. 3 illustrates mapping of CIA-PET. CIA-PETs representing real interacting regions are expected to span two different genomic regions, and multiple CIA-PETs are expected to be clustered.
Figure 5:
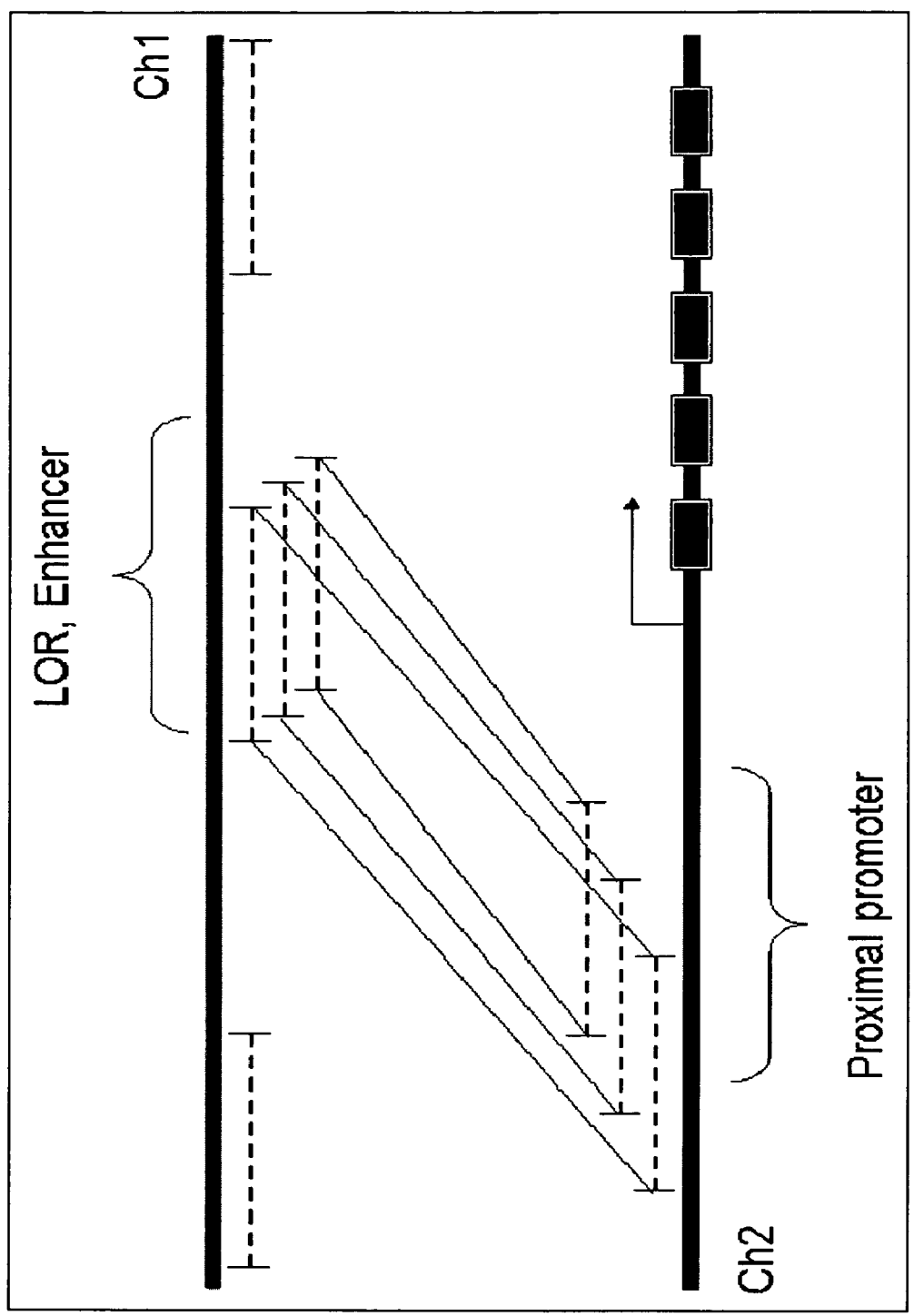
FIG. 5 illustrates mapping CIA-diPET. CIA-diPETs representing the interacting regions are expected to span two different genomic regions, and multiple CIA-diPETs are expected to be clustered. The additional information provided by the two PETs of the CIA-diPET will be useful in mapping the CIA-diPETs to the genome.

Thus the present invention provides in one aspect, a method to identify chromatin interaction events mediated by specific DNA binding proteins, such as histones, across long distances and between different chromosomes. In another aspect, the present invention provides an isolated oligonucleotide comprising at least one first tag and at least one second tag, wherein the first tag is obtained from a first polynucleotide and the second tag obtained from a second polynucleotide, the first and second polynucleotides obtained from a nucleic acid-protein complex. The tags correspond to regions of chromatin in nucleic acid-protein complexes. These tags may then be sequenced to analyse, identify, and/or detect chromatin interaction events (FIGS. 3 and 5).

The isolated oligonucleotide may further comprises at least one linker. The linker may be inserted between the tags or a linker may be positioned upstream and/or downstream the at least one tag. The linker may comprises at least one restriction enzyme recognition site; the at least one restriction enzyme recognition site may be asymmetric, the at least one restriction enzyme recognition site may be for a type IIs restriction enzyme or for a homing restriction enzyme.

Alternatively, the at least one first tag may comprise a 5' terminus and a 3' terminus from the first polynucleotide and the at least one second tag comprises a 5' terminus and a 3' terminus from the second polynucleotide. The isolated oligonucleotide may further comprise at least one linker. The linker may be inserted between the tags or a linker may be positioned upstream and/or downstream the at least one tag. The linker comprises at least one restriction enzyme recognition site; the at least one restriction enzyme recognition site may be asymmetric, the at least one restriction enzyme recognition site may be for a type IIs restriction enzyme or for a homing restriction enzyme.

Figure 4:
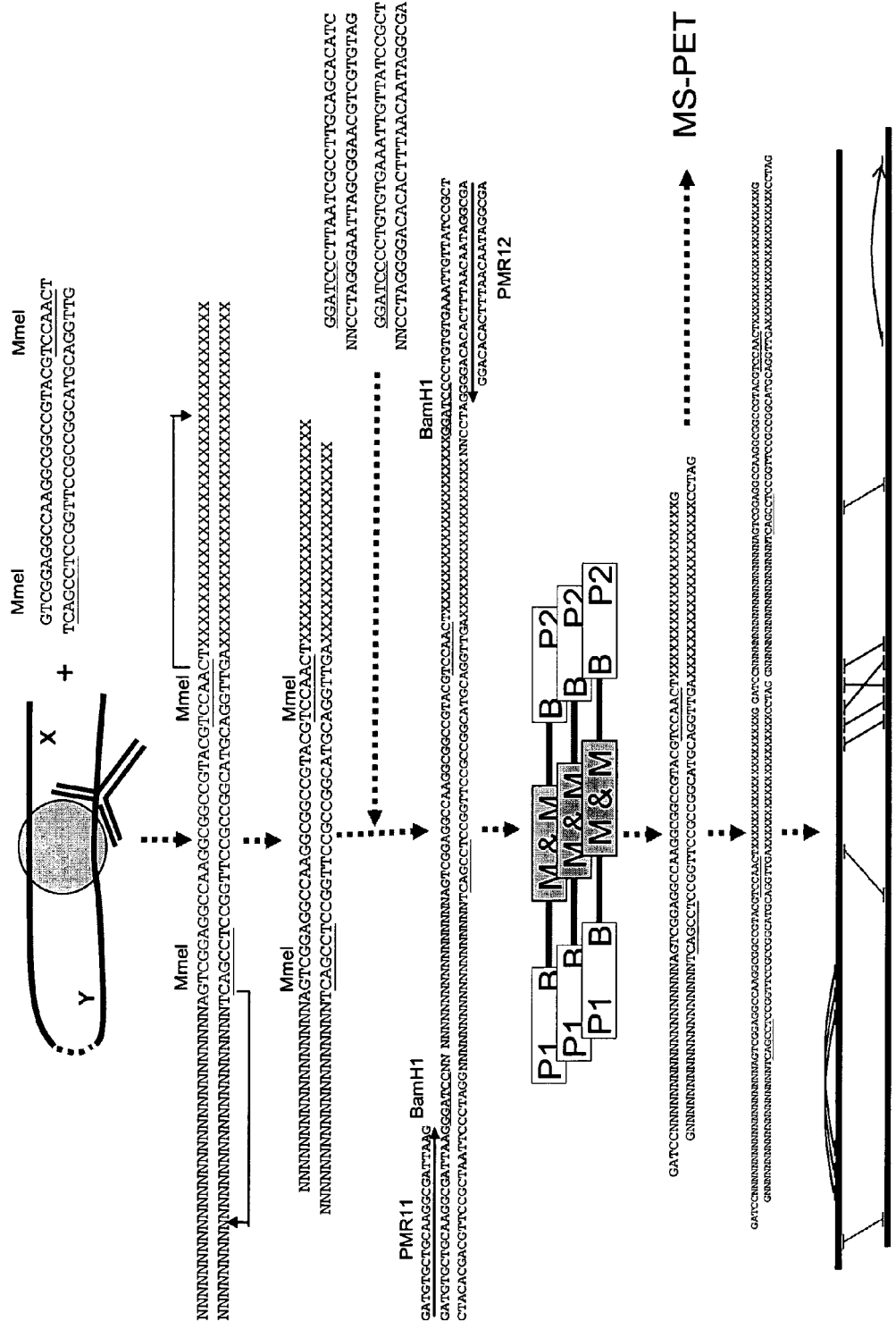
FIG. 4 illustrates the relevant restriction enzyme recognition sequences for CIA-PET. Each base indicated with N or X may be any nucleotide (either A, C, G or T). The regions comprising N and X represent portions obtained from different polynucleotides. The sequences which appear in the figure from top to bottom are as follows: SEQ ID NO:1, SEQ ID NO:2, SEQ ID NO:36, SEQ ID NO:37, SEQ ID NO:20, SEQ ID NO:21, SEQ ID NO:5, SEQ ID NO:6, SEQ ID NO:7, SEQ ID NO:8, SEQ ID NO:13, SEQ ID NO:22, SEQ ID NO:23, SEQ ID NO:14, SEQ ID NO:24, SEQ ID NO:25 (SEQ ID Nos:24 and 25 repeated thrice).

The linker may comprise a first restriction recognition site recognized by a restriction enzyme capable of cleaving the first polynucleotide to obtain the first tag, and a second restriction recognition site recognized by a restriction enzyme capable of cleaving the second polynucleotide to obtain the second tag (FIGS. 1 and 4).

The linker may comprise a first restriction recognition site recognized by a restriction enzyme capable of cleaving the first polynucleotide to obtain a 3' terminus of the first polynucleotide, and a second restriction recognition site recognized by a second restriction enzyme capable of cleaving the second polynucleotide to obtain a 5' terminus of the second polynucleotide. Alternatively, the linker may comprise a first restriction recognition site recognized by a restriction enzyme capable of cleaving the first polynucleotide to obtain a 5' terminus of the first polynucleotide, and a second restriction recognition site recognized by a second restriction enzyme capable of cleaving the second polynucleotide to obtain a 3' terminus of the second polynucleotide.

Figure 6:
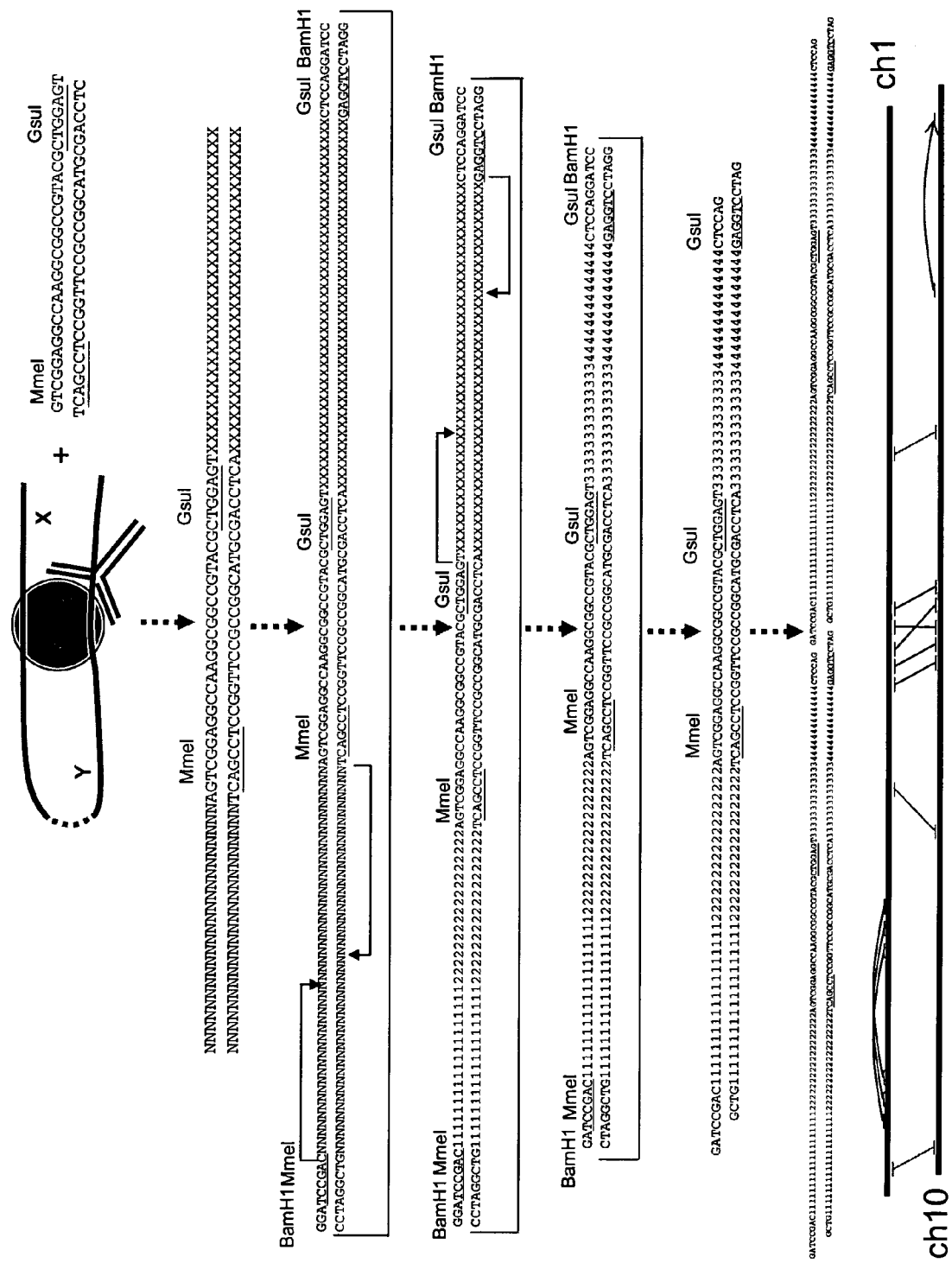
FIG. 6 illustrates the relevant restriction enzyme recognition sequences for CIA-diPET. The bases N and X represent any nucleotide (either A, C, G or T) and they are obtained from different polynucleotides. The numerals 1 and 2 represent nucleotides from two regions or termini obtained from one polynucleotide while the numerals 3 and 4 represent nucleotides from two regions or termini obtained from another polynucleotide. The numerals (1, 2, 3, and/or 4) may represent any nucleotide (either A, C, G or T). The sequences which appear in the figure from top to bottom are as follows: SEQ ID NO:3, SEQ ID NO:4, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35 (SEQ ID Nos:24 and 25 repeated thrice).

The first polynucleotide may be further cleaved by a third restriction enzyme recognizing a third recognition site to obtain a 3' terminus of first polynucleotide and the second polynucleotide may be further cleaved by a fourth restriction enzyme recognizing a fourth recognition site to obtain a 5' terminus of the second polynucleotide; the at least one first tag obtained from ligating the 5' and 3' termini of the first polynucleotide and the at least one second tag obtained from ligating the 5' and 3' termini of the second polynucleotide (FIGS. 2 and 6). The first and third recognition sites may possess the same sequence and the second and fourth recognition sites may possess the same sequence.

The nucleic acid-protein complex of the isolated oligonucleotide may be part of a chromatin structure. The nucleic acid fragment to which a protein of interest binds may be any nucleic acid fragment comprising a region to which a protein of interest binds, for example, histone binding site. The polynucleotides may be DNA or RNA.

The resulting CIA-PET sequences may be mapped to reference genome sequences to localize the chromatin interaction junction points, which may be either long range intra-chromosome (on the same chromosome) or inter-chromosome (on different chromosomes). This information may be used for study of chromosomal 3-dimensional organization structures in nuclei, coordinated gene regulation in long distance and across different chromosomes mediated by transcription factors, and other epigenetic related questions (FIGS. 3 and 5).

With complete genome sequences available, it is possible to develop whole genome approaches to identify all potential chromatin interactions. Whole genome tiling array is an attractive approach for genome interrogation, in which 20-60mer oligonucleotides are tiled to cover the entire genome in microarrays, and DNA probes with biological contents are hybridized to the array, and the profiles of hybridization signal intensity of all the array elements is the readout for interrogation of genetic elements. Tiling arrays have been demonstrated useful for identifying exons, and for localizing transcription factor binding sites when coupled with ChIP (ChIP-chip). Though the array-based approach is efficient due to its highly multiplex and parallel nature, it is inconceivable that the hybridization-based detection will be capable of detecting non-linear relationship of two DNA fragments in chromatin interactions.

Preparation of the Oligonucleotide According to One Embodiment

The nucleic acid-protein complex may be obtained through Chromatin immunoprecipitation (ChIP).

Chromatin Immunoprecipitation (ChIP)

ChIP has been used to enrich and thereby allow the identification of genomic regions associated with specific proteins such as histones and other proteins binding to nucleic acids in nucleic-acid protein complexes (reviewed in Taverner et al., Genome Biol, 2004. 5(3): p. 210). The aim is to cross-link proteins with DNA at their sites of interaction. This is accomplished quickly and efficiently by adding a suitable fixative such as formaldehyde, glutaldehyde or methanol directly to living cells in culture.

Crude extracts of these fixed cells are then prepared, and the chromatin sheared by sonication, hydroshearing, repeated drawing through a hypodermic syringe needle or by restriction enzyme digestion to an average size of usually about 1 kb, then used in immunoprecipitation reactions with antibodies raised against the DNA-associated protein of interest (e.g. transcription factors or histones). DNA fragments enriched in each immunoprecipitation are then de-linked and purified to allow their identification by a variety of methods. The advantage of using ChIP is that this approach is able to "freeze" the in vivo gene regulatory network by rapid cross-linking of chromatin and other non-histone proteins, thereby in theory representing a "true" picture of the regulatory system at any point in time, free of potential artifacts imposed by heterologous expression, for instance.

Recently, ChIP has been combined with whole-genome (Lieb et al., Nat Genet, 2001. 28(4): p. 327-34), whole-chromosomal (Euskirchen et al., Mol Cell Biol, 2004. 24(9): p. 3804-14) and CpG island (Weinmann et al., Genes Dev, 2002. 16(2): p. 235-44) or microarrays in a "ChIP-chip" or "ChIP-on-chip" approach that promises to enable the genome-level localization of protein-binding sites such as transcription factor binding sites (TFBS) (reviewed in Buck and Lieb, 2004). While the usefulness of this approach has been demonstrated for small genomes such as yeast (Lieb et al., Nat Genet, 2001. 28(4): p. 327-34), the cost and complexity of producing whole-genome microarrays for more complex organisms still remains a limiting factor.

CpG island microarrays contain human genomic fragments of high CpG content, and because CpG islands often correspond to promoter regions (Antequera and Bird, Proc Natl Acad Sci USA, 1993. 90(24): p. 11995-9), such microarrays represent a possible compromise. However, the location of putative protein-binding sites still has to be indirectly inferred by examining genomic DNA upstream and downstream (usually 1-2 kb, as this is the approximate size of sonicated ChIP fragments) of the CpG-rich probe spotted on the array.

As an alternative, cloning and sequencing of the ChIP-enriched DNA fragments has previously been attempted but with limited success. The problem is that the targets of ChIP enrichment are obtained against a high background of the entire genome. Even a 100-fold enrichment of specific targets would still represent only a small fraction of clones in a ChIP library, making standard DNA sequencing a very costly solution. Therefore, sequencing ChIP clones under these circumstances is not a good approach for identifying the enriched targets. Serial Analysis of Gene Expression (SAGE) and Massively Parallel Signature Sequencing (MPSS) (Brenner et al., Nat Biotechnol, 2000. 18(6): p. 630-4) have also been suggested as useful quantitative tools for detecting ChIP enrichment, the underlying principle being that the tags generated from ChIP-enriched DNA fragments would be present in larger numbers compared to the non-specific background.

These tags could then be mapped to the genome sequence for identification of the general region of interest (i.e. assumed to be 1-2 kb, representing the sonicated fragments). Although the 20 bp SAGE and MPSS tags should be specific enough in most instances to define the specific genome location, one still has to examine all sequences approximately 1-2 kb upstream and downstream of the tag when mapping to the genome. This is the same problem faced by the CpG island microarray approach. Furthermore, complete coverage using these methods depends on the availability of prerequisite restriction enzyme recognition sites (mapping-enzyme sites); if a recognition site is absent from a certain genomic location, that particular tag will be missing from the corresponding ChIP fragment, and hence that location will be a "blind spot" within the genome.

From the issues described above, it is clear that what is required to facilitate genome level transcriptional regulatory analysis is a method to accurately and rapidly pinpoint the nucleic acid sequences flanking protein binding regions, as an alternative to whole genome arrays. In this regard, the novel approach provided by the present invention, possesses several advantages: (i) the tag sequences generated by one method of the present invention provide higher specificity for mapping, because each tag would already be known to have been derived from a contiguous DNA segment encompassed by the 5' and 3' signatures. This information facilitates precise localization of the genomic region of interest, and obviates the need to repeatedly examine every sequence an arbitrary 1-2 kb upstream and downstream of a standard SAGE or MPSS tag; (ii) the method of the present invention is thus independent of any requirement for the presence of mapping-enzyme sites; (iii) the concatenation of tags prior to sequencing means that several tags may be identified within one sequencing read; (iv) the region that is common to (i.e. overlapped by) all mapped tags in that cluster therefore defines the DNA regions involved in the nucleic acid-protein complex in question.

Tags and Ditags

For the purpose of the present application, a tag is a nucleotide sequence or signature obtained from a nucleic acid molecule and represents the polynucleotide from which the tag was obtained or derived from. The polynucleotide which is intended to shrink or represent may be RNA, mRNA, genomic DNA, full-length cDNA, or cDNA.

Under the present invention, two tags that are present in an oligonucleotide of the present invention may also each be called a ditag. Like tags, a ditag is shorter than the original nucleic acid molecule from which it originates or which it represents. Preferably, the ditag must be much shorter than the original nucleic acid molecule. As consequence of the "shrinking", the ditag may essentially comprises either or both the 5' end region (also indicated as 5' tag) and 3' end region (also indicated as 3' tag) of the original nucleic acid molecule. Hence, the portion of the original nucleic acid molecule that is originally between or inside the 5' tag and 3' tag is not included in the ditag. The ditag according to the invention retains the most informative features of the original nucleic acid molecule, namely the start and the end signatures of the nucleic acid.

The 5' tag and 3' tag forming the ditag may have the same or different size. Preferably, they have the same number of nucleotides. The ditag may be of any size, but needs to be meaningful and advantageous over the size of the parental sequence from which it is derived. The preferred size of a tag or ditag is determined by genome complexity. For a bacterial genome a tag from about 8 bp to about 16 bp may be sufficient whereas for a complex genome like the human genome, a 16-20 bp tag (or in other words, a 32-40 bp ditag) may be considered. In general, the size of the ditag is from about 12-60 bp.

For the purpose of the present application, the terms 5'-terminus, 5'-end and 5'-tag are equivalent to each other and may be used interchangeably. In the same way, the terms 3'-terminus, 3'-end and 3'-tag are equivalent to each other and may be used interchangeably. In an original nucleic acid molecule or portion inside a nucleic acid molecule that one intends to reduce or represent, each of the 5'-end and 3'-end represents a region or portion closest to the extremity and most far from the middle region of the molecule.

According to one aspect of the present invention, the 5'-tag and 3'-tag comprised in the ditag are the regions of the molecule cleaved by a restriction enzyme closest to the 5'-end and 3'-end, respectively, of the nucleic acid molecule or portion thereof which is intended to be reduced or represented. Accordingly, the size of the ditag may be determined by the restriction enzyme or enzymes used.

Accordingly, the invention provides an isolated oligonucleotide comprising an isolated oligonucleotide comprising at least one first tag and at least one second tag, wherein the first tag is obtained from a first polynucleotide and the second tag obtained from a second polynucleotide, the first and second polynucleotides obtained from a nucleic acid-protein complex. The oligonucleotide may further comprise at least one linker inserted between the tags. The oligonucleotide may also further comprise at least one linker inserted to flank a tag (that is, the at least one linker may be positioned upstream and/or downstream the at least one tag).

Linker

In particular, each linker may comprise at least: one first restriction site and at least a second adjacent restriction site. Therefore, the number of restriction sites present in each linker may be one or more, preferably two. The restriction site may be an asymmetric restriction site. Examples of asymmetric restriction sites are homing endonuclease asymmetric recognition sites, and some type II (or class II) recognition sites. Type IIs restriction enzymes that cut to one side of their recognition sites are preferable.

However, any recognition site known in the art may be used. Restriction enzyme recognizing at least one recognition site within the nucleic acid molecule and which may be used will be evident to those skilled in the art (see for example, Current Protocols in Molecular Biology, Vol. 2, 1995, Ed. Ausubel, et al., Greene Publish. Assoc. & Wiley Interscience, Unit 3.1.15; New England Biolabs Catalog, 2005). A list of possible restriction sites and corresponding restriction enzymes recognizing is reported below.

As an example, a restriction enzyme recognizing a restriction site may be used for the purpose of the preparation of the ditag according to the invention. In particular a type IIs enzyme, for example MmeI. When MmeI is used, this enzyme recognizes a sequence inside each of the two adaptors that flank the nucleic acid molecule that one intends to reduce, but cuts inside the nucleic acid molecule forming a tag comprising 17-21 nucleotides (see MmeI cuts indicated in FIGS. 1 and 4). Two such tags may be additionally processed by blunting and ligation to form a ditag comprising 34-38 nucleotides. The ditag is hence obtained by splicing together or ligating the 5' terminus and the 3' terminus of the same nucleic acid molecule.

As an example, asymmetric sites may be introduced. Asymmetric site sequences useful for the purpose of the present invention are: i) two homing endonuclease asymmetric recognition site sequences or ii) restriction endonuclease asymmetric cleavage sites sequences recognizable by type II restriction enzymes.

Homing endonucleases are sold and described by New England Biolabs, Inc.; a description of the asymmetric site sequences is also available in the New England Biolabs Catalog. These homing endonuclease asymmetric recognition site sequences are from 18 to 39 bp. However, in the present invention the recognition site sequences are not limited to those sequences nor to these sizes. Preferably, the restriction homing endonucleases capable of cutting the asymmetric site sequences are selected from the group consisting of: I-CeuI, PI-SceI, PI-PspI and I-SceI. The list mentioned above however is not exhaustive. Other homing endonucleases known in the art and those which may be later discovered are included in the scope of the present invention.

Examples of type II restriction enzymes include: AarI, AceIII, AloI, BaeI, Bbr7I, BbvI, BbvII, BccI, Bce83I, BceAI, BcefI, BcgI, BciVI, BfiI, BinI, BplI, BsaXI, BscAI, BseMII, BseRI, BsgI, BsmI, BsmAI, BsmFI, Bsp24I, BspCNI, BspMI, BsrI, BsrDI, BstF5I, BtgZI, BtsI, CjeI, CjePI, EciI, Eco31I, Eco57I, Eco57MI, Esp3I, FalI, FauI, FokI, GsuI, HaeIV, HgaI, Hin4I, HphI, HpyAV, Ksp632I, MboII, MlyI, MmeI, MnlI, PleI, PpiI, PsrI, RleAI, SapI, SfaNI, SspD5I, Sth132I, StsI, TaqII, TspDTI, TspGWI, TspRI and Tth111II (the list in the web site of Rebase Enzymes®: http://rebase.neb.com/cgi-bin/outsidelist; see also Szybalski, W., 1985, Gene, 40:169). The list mentioned above however is not exhaustive. Other type II enzymes known in the art and those which may be later discovered are included in the scope of the present invention.

Examples of recognition sites and cleavage sites of several class II restriction enzymes are (into parenthesis are the recognition site and the cleavage site): BbvI (GCAGC 8/12), HgaI (GACGC 5/10), BsmFI (GGGAC 10/14) SfaNI (GCATC 5/9), and Bsp I (ACCTGC 4/8).

Artificial restriction endonucleases may also be used. These endonucleases may be prepared by protein engineering. For example, the endonuclease FokI has been engineered by insertions so that it cleaves one nucleotide further away from its recognition site on both strands of the DNA substrates. See Li and Chandrasegaran, Proc. Nat. Acad. Sciences USA 90:2764-8, 1993. Such techniques may be applied to prepare restriction endonucleases with desirable recognition sequences and desirable distances from recognition site to cleavage site.

Under the present invention, the isolated oligonucleotide of the present invention may be joined or concatenated with other isolated oligonucleotide to form a concatemer of oligonucleotides. Any number of oligonucleotides may be joined together for the purposes of sequencing or for cloning into a suitable plasmid or vector.

Accordingly, in another aspect, the present invention is a concatemer of oligonucleotides comprising at least two isolated oligonucleotides, each isolated oligonucleotide comprising at least one first tag and at least one second tag, wherein the first tag is obtained from a first polynucleotide and the second tag obtained from a second polynucleotide, the first and second polynucleotides obtained from a nucleic acid-protein complex.

The isolated oligonucleotides of the concatemer of oligonucleotides may further comprise at least one linker. The linker may be inserted between the tags. Alternatively, a linker may flank a tag. The linker may comprise at least one restriction enzyme recognition site; the at least one restriction enzyme recognition site may be for a type IIs restriction enzyme.

In one embodiment, the first tag of the concatemer of oligonucleotides may comprise a 3' terminus from the first polynucleotide and the second tag further comprises a 5' terminus from the second polynucleotide. The isolated oligonucleotides of the concatenated polynucleotide may each further comprise at least one linker inserted between the tags. In another embodiment, the first tag of the concatemer of oligonucleotides may comprise a 5' terminus from the first polynucleotide and the second tag further comprises a 3' terminus from the second polynucleotide.

In another embodiment, the first tag of the concatemer of oligonucleotides may comprise a 5' terminus and a 3' terminus from the first polynucleotide and the second tag further comprises a 5' terminus and a 3' terminus from the second polynucleotide. The isolated oligonucleotides of the concatemer of oligonucleotides may each further comprise at least one linker inserted between the tags.

The linkers of either of these embodiments may comprise at least one restriction enzyme recognition site; the at least one restriction enzyme recognition site may be for a type IIs restriction enzyme.

The concatemer of oligonucleotides may be inserted into a vector or a cell; the cell may be a bacterial cell.

The concatemer of oligonucleotides may be from a chromatin structure. The polynucleotides are located on the same chromosome or the polynucleotides are located on different chromosomes.

While these are preferred concatemer(s), it will be apparent that the number of oligonucleotides of the present invention that may be concatenated depends on the length of the oligonucleotides and may be readily determined by those of skilled in the art without undue experimentation. After formation of concatemers, multiple tags may be cloned into a vector for sequence analysis, or ditags or concatemers may be directly sequenced without cloning by methods known to those of skill in the art. Hence, the concatenation of ditags allows an efficient analysis of the nucleic acid molecules, like full-length cDNAs, in a serial manner by sequencing multiple ditags within a single vector or clone.

While term vector or recombinant vector it is intended, a plasmid, virus or other vehicle known in the art that has been manipulated by insertion or incorporation of the ditag genetic sequences may also be used. Such vectors contain a promoter sequence that facilitates the efficient transcription. The vector typically contains an origin of replication, a promoter, as well as specific genes that allow phenotypic selection of the transformed cells. Vectors suitable for use in the present invention include for example, pBlueScript (Stratagene, La Jolla, Calif.); pBC, pZErO-1 (Invitrogen, Carlsbad, Calif.) and pGEM3z (Promega, Madison, Wis.) or modified vectors thereof as well as other similar vectors known to those of skill in the art. As a particular realization, the pGEM3z vector has been modified, and will be referred to as pGIS8 (FIGS. 7 and 11). pGEM vectors have also been disclosed in U.S. Pat. No. 4,766,072, herein incorporated by reference.

For the production of the parental polynucleotide or nucleic acid molecule from which the tags or ditags were derived, as full-length libraries, suitable vectors may be used. Accordingly, suitable vectors, which are within the scope of the present invention, are those wherein the backbone of the vector does not comprise the same restriction site comprised in the adaptors flanking the polynucleotide or the ditag, after insertion of the polynucleotide. Preferably, the invention provides a vector wherein the vector backbone (other than within the stuffer region containing multiple cloning sites that is removed during insertion of the polynucleotide) does not comprise the first restriction site and the second or further restriction sites that are comprised into the adaptors. In particular, the vector does not comprise the at least II restriction site (for example type IIs restriction site) and the at least second or further restriction site comprised in the adaptors. More preferably, the vector backbone (other than within the stuffer region that is removed during insertion of the polynucleotide) does not comprise MmeI and BamHI.

Figure 7:
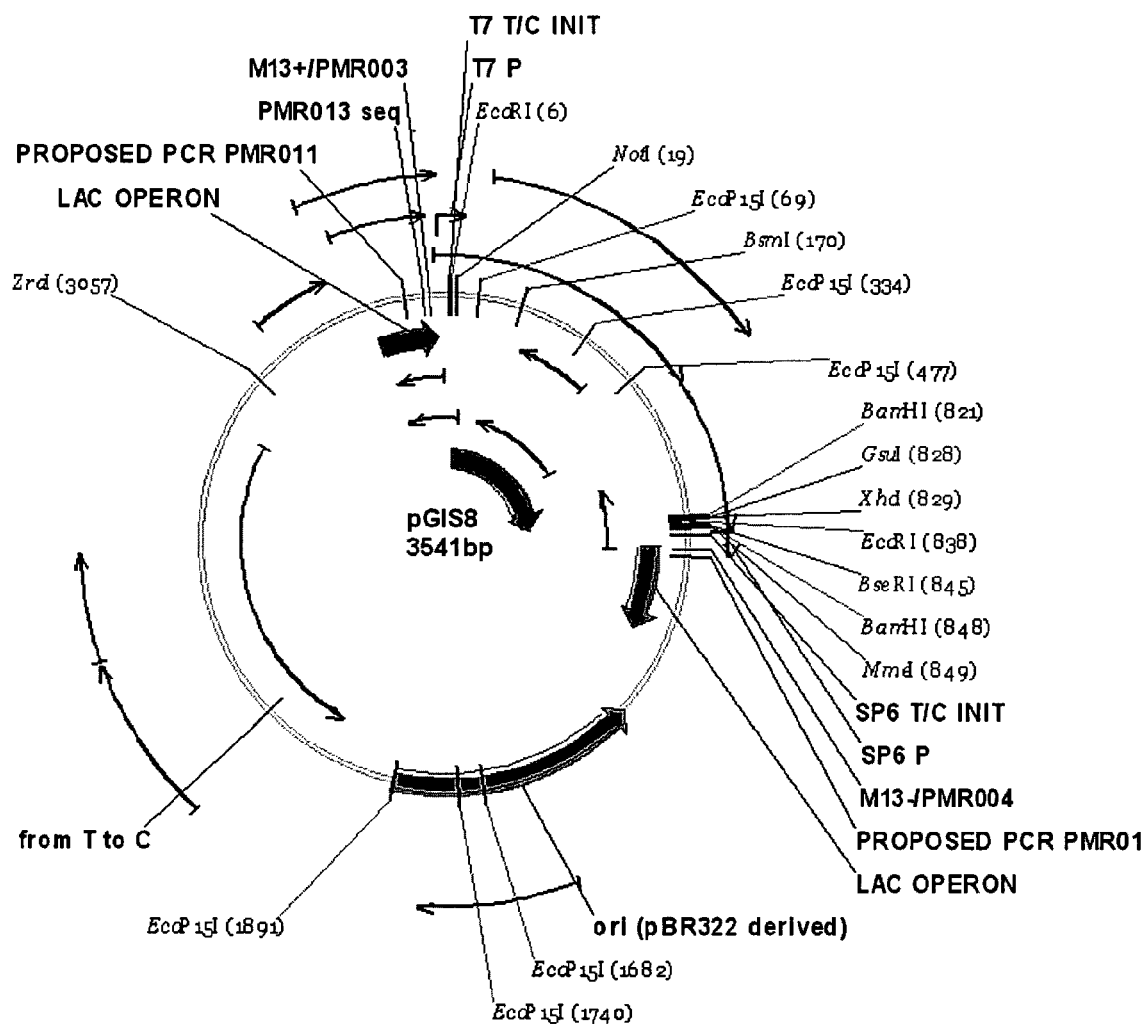
FIG. 7 illustrates the vector pGIS8 containing multiple unique cloning sites, which is an example of a vector that may be used under the present invention.

An example of such a vector not comprising MmeI in any region outside of the stuffer is the vector pGIS8 shown in FIGS. 7 and 11. In pGIS8 the MmeI recognition sites were deleted by mutagenesis.

Accordingly, the present invention provides a library of oligonucleotides comprising at least one oligonucleotide, the oligonucleotide comprising at least one first tag and at least one second tag, wherein the first tag is obtained from a first polynucleotide and the second tag obtained from a second polynucleotide, the first and second polynucleotides obtained from a nucleic acid-protein complex. There is also provided a library of concatemer(s) of oligonucleotides according to the invention.

The at least one oligonucleotide of the library of oligonucleotides may comprise at least one linker is inserted between the tags. Alternatively, a linker may instead flank a tag. The first tag may comprise a 5' terminus and a 3' terminus from the first polynucleotide and the second tag further comprises a 5' terminus and a 3' terminus from the second polynucleotide.

The polynucleotide nucleic acid-protein complex may be part of a chromatin structure. The polynucleotides may be located on the same chromosome or the polynucleotides may be located on different chromosomes.

According to one aspect, the oligonucleotide is amplified. For example, by using PCR or any other known amplification methods. The PCR primers and the probes sequences may be prepared based on the information of the sequence of the ditags. Accordingly, suitable PCR primers corresponding to specific regions inside the vector are used. Such regions flank the oligonucleotide comprising the ditag and adaptors. PCR may be performed directly on the ligation (self-circularization) reaction to obtain short (for example 200 bp) PCR products.

These PCR products that contain the required ditags may then be cut with an enzyme recognizing the at least second restriction site (inside the adaptors) to generate the required short cohesive ditags. As restriction enzyme recognizing the second or further restriction site, BamHI may for example be used, and cohesive ditags of 50 bp are generated. The advantage of this amplification step is that of generating ditags circumvents the need to produce a ditag library amplification, which may be avoided by not transforming the self-circularized tagged plasmids. The amplified oligonucleotide may then subsequently be excised from the vector (in this example, by digestion with BamHI) and concatenated in long stretches of DNA or RNA for subsequent cloning and sequencing analysis (FIGS. 1 and 2).

As a particular aspect, the invention discloses a cDNA library wherein the oligonucleotide(s) comprises at least one ditag, and wherein the ditag comprises about 34-38 nucleotides and is obtained by splicing nucleotides from the 5' terminus and nucleotides from the 3' terminus of a full-length cDNA or fragment thereof.

The ditag library according to the invention is representative of the library comprising the original nucleic acid molecules. For example, when the library comprising the nucleic acid molecules is a full-length polynucleotide library, the ditag library is representative of the full-length ditag library Each ditag clone comprises sufficient information characterizing the specific full-length clone. More important, the ditag of the invention comprises the 5'-end and 3'-end of an original full-length polynucleotide derived from the nucleic acid-protein complex. Hence, the ditag is representative of the structure of the polynucleotide.

Accordingly, it is sufficient to sequence and analyze the ditag clones of the ditag library. In case a ditag of interest is found, the corresponding full-length polynucleotide may be selected and prepared from the full-length polynucleotide library, for example by PCR or directly from target RNA samples by reverse transcription-polymerase chain reaction (RT-PCR).

Sequencing the oligonucleotides of the invention may be performed by the "454" sequencing (pyrosequencing) method (Margulies et al, 2005), or concatemerized into longer DNA stretches for cloning to make CIA-PET library and followed by sequencing using the Sanger capillary method.

Accordingly, the present invention provides methods to prepare the oligonucleotide of the invention, to detecting and/or identifying at least two polynucleotides from a nucleic acid-protein complex, and to prepare vectors comprising the oligonucleotides and concatenated oligonucleotides of the present invention.

Thus, in another aspect, the present invention provides a method of preparing at least one isolated oligonucleotide comprising:
(a) providing a nucleic acid-protein complex;
(b) preparing an oligonucleotide comprising at least one first tag and at least one second tag, wherein the first and second tags are obtained from a nucleic acid-protein complex; and
(c) isolating the oligonucleotide.

In particular, there is provided a method of preparing at least one isolated oligonucleotide comprising:
(a) providing a nucleic acid-protein complex;
(b) preparing an oligonucleotide comprising at least one first tag and at least one second tag, wherein the first tag is obtained from a first polynucleotide and the second tag obtained from a second polynucleotide, the first and second polynucleotides obtained from a nucleic acid-protein complex; and
(c) isolating the oligonucleotide.

In one embodiment, step (b) of this aspect of the invention comprises:
(i) inserting at least one linker comprising at least one restriction enzyme recognition site, and
(ii) cleaving the first and second polynucleotides with a least one restriction enzyme recognizing the at least one recognition site in the linker to form the oligonucleotide comprising a first tag obtained from the first polynucleotide, a second tag obtained from the second polynucleotide and the linker between the tags.

In another embodiment, step (b) of this aspect of the invention comprises:
(i) inserting at least one linker comprising at least one restriction enzyme recognition site between the first polynucleotide and the second polynucleotide of the complex;
(ii) adding at least one restriction enzyme recognition site each to the 5' terminus of the first polynucleotide and the 3' terminus of the second polynucleotide;
(iii) cleaving the first and second polynucleotides with at least one restriction enzyme recognizing at least one recognition site to obtain cleaved fragments; and
(iv) ligating cleaved fragments to form the oligonucleotide comprising a first tag obtained from the first polynucleotide, a second tag obtained from the second polynucleotide, the tags comprising 5' and 3' termini of each polynucleotide, and the linker inserted between the tags and the at least one restriction enzyme recognition site in step (ii) is part of a vector.

The nucleic acid-protein complex may be obtained by chromatin immunoprecipitation.

In another aspect, the present invention provides a method of detecting and/or identifying at least two polynucleotides from a nucleic acid-protein complex, the method comprising:
(a) providing a nucleic acid-protein complex;
(b) preparing an oligonucleotide comprising at least one first tag and at least one second tag, wherein the first tag is obtained from a first polynucleotide and the second tag obtained from a second polynucleotide, the first and second polynucleotides obtained from a nucleic acid-protein complex;
(c) sequencing the oligonucleotide; and
(d) mapping the at least two polynucleotides based on the nucleotide sequences of the first and second tags, thereby detecting and/or identifying the at least two polynucleotides.

In one embodiment, step (b) of this aspect of the invention comprises:
(i) inserting at least one linker comprising at least one restriction recognition site, and
(ii) cleaving the first and second polynucleotides with a least one restriction enzyme recognizing the at least one recognition site in the linker to form the oligonucleotide comprising a first tag obtained from the first polynucleotide, a second tag obtained from the second polynucleotide and the linker between the tags.

In another embodiment, step (b) of this aspect of the invention comprises:
(i) inserting at least one linker comprising at least one restriction enzyme recognition site between the first polynucleotide and the second polynucleotide of the complex;
(ii) adding at least one restriction enzyme recognition site each to the 5' terminus of the first polynucleotide and the 3' terminus of the second polynucleotide;
(iii) cleaving the first and second polynucleotides with at least one restriction enzyme recognizing at least one recognition site to obtain cleaved fragments; and
(iv) ligating cleaved fragments to form the oligonucleotide comprising a first tag obtained from the first polynucleotide, a second tag obtained from the second polynucleotide, the tags comprising 5' and 3' termini of each polynucleotide, and the linker inserted between the tags; the at least one restriction enzyme recognition site in step (ii) may be part of an adaptor or a vector.

The nucleic acid-protein complex under the present invention may be obtained by chromatin immunoprecipitation. The nucleic acid-protein complex may be obtained by incorporating a photoactivatable moiety into the DNA and/or the protein of interest and isolation of DNA/protein complex by antibody-mediated precipitation or by affinity-mediated technique. Examples of such affinity-based techniques include streptavidin/biotin, glutathione-S-transferase/glutatathione matrix, and maltose-binding protein/amylose matrix interactions.

The oligonucleotide obtained in step (b) may be amplified before being sequenced in step (c); the amplification may be by polymerase chain reaction. The amplified oligonucleotides may be subjected to at least one purification step after amplification but before being sequenced in step (c). The at least one purification step may be gel electrophoresis.

The oligonucleotide according to the invention may be concatenated with at least one other oligonucleotide obtained by steps (a) to (b) before being sequenced to make a concatemer of oligonucleotides.

The sequencing may be by the Sanger method or by multiplex sequencing. The multiplex sequencing may be pyrosequencing. Any suitable method of sequencing such as those described by Bonetta (2006) may be employed. The nucleic acid fragment to which a protein of interest binds may be any nucleic acid fragment comprising a region to which a protein of interest binds, for example, a histone binding site. The polynucleotides may be DNA or RNA.

The polynucleotides may located on the same chromosome or the polynucleotides may be located on different chromosomes.

The detecting and/or identifying may be for transfusion or translocation of the polynucleotides.

The oligonucleotide may be transfected into a cell. The transfection may be by electroporation. The cell may be a bacterial cell.

The embodiments of this aspect of the invention are described in more detail below as the CIA-PET and CIA-diPET techniques below.

In another aspect, the present invention is a vector comprising the oligonucleotide, the concatemer of oligonucleotides or the library of oligonucleotides of the present invention.

CIA-PET

In the CIA-PET method (FIGS. 1 and 4), DNA fragments tethered by protein in DPD complexes will be joined by linker sequences through ligation. The linker sequence contains two MmeI sites. After reversal of the cross-linking, the ligated DNA will be digested by MmeI to release the paired end ditag (CIA-PET). Each of the CIA-PETs contains a linker with two flanked tags (about 20 bp each) (Step 2 labeled in FIG. 1). The two tags contained in a CIA-PET thus represent two distal genetic regions that are far away from each other in linear genome sequence, but interacting together and mediated by a specific protein such as a histone protein.

After the CIA-PETs are gel-purified, sequence specific adaptors are added to each side of the CIA-PETs, which are then amplified by PCR (Step 3 in FIG. 1). The amplified CIA-PETs may be directly sequenced by a multiplex sequencing method such as the "454" pyrosequencing method or any other suitable sequencing methods, or concatemerized into longer DNA stretches for cloning to make CIA-PET library and followed by sequencing using the Sanger capillary method. The CIA-PET sequences will be mapped to the reference genome sequences. True chromatin interaction sites may be identified based on frequent occurrence of CIA-PET clusters in specific loci, which will be distinguished from background noise randomly scattered as singletons (FIG. 3).

CIA-diPET

In the CIA-diPET method (FIGS. 2 and 6), paired end ditag sequences representing each of the two related DNA fragments are extracted and sequenced compared to only one tag per sequence. As such, the resulting CIA-diPET will contain longer tag sequences than the tags of the CIA-PET method. It will be appreciated by a person skilled in the art that the CIA detection method of the present invention is thus more specific in mapping chromatin interactions than other methods of the prior art. The DNA fragments in DPD complexes are joined by a linker sequence that contains a MmeI site and a GsuI site. After reverse cross-linking, the ligated DNA will be randomly broken by sonication.

The DNA will then be size fractionated and cloned into a pGIS8 vector (Step 2 of FIG. 2) that contains an immediate MmeI site and a Gsu site at its cloning site (FIG. 7). After transformation and propagation in bacteria cells, the library clones are subjected by sequential manipulations of digestion, self-ligation, and transformation to create the single diPET library. The plasmid DNA of the single diPET library will be digested by BamHI to release the diPET structure (Step 4 of FIG. 2), which may be directly sequenced using the MS-PET sequencing method, or further concatenated for cloning and sequencing. The CIA-diPET sequences will be mapped to the reference genome sequences. True chromatin interaction sites may be identified based on frequent occurrence of CIA-diPET clusters in specific loci, which will be distinguished from background noise randomly scattered as singletons (FIG. 5).

Having now generally described the invention, the same will be more readily understood through reference to the following examples that are provided by way of illustration and are not intended to be limiting of the present invention.

For quality control and to ensure correct insertion of linkers or adaptors, gel electrophoresis is performed to remove unwanted fragments (FIGS. 8 to 10) during the process.

EXAMPLES

Methodology of CIA

The Nanog transcription factor in mouse ES cell (E14) and ChIP-PET data for Nanog and other key ES cell transcription factors such as Oct4 and Sox2 were used as the biological system to practice the present invention. The ChIP-PET data provides a linear map of where these transcription factors bind to, and will be used as reference to validate the chromatin interaction data. The interactions between chromatins were detected by two methods, CIA-PET and CIA-diPET.

The sequences used in the examples are as below, and in the sequence listing. Where two strands are shown, the top strand is the sense strand and the bottom strand is the antisense strand. All sequences are shown in the 5' to 3' direction. Where a nucleotide is denoted by N or n (or X or a numeral in the Figures), it means that any nucleotide (A, C, G or T) may be represented in that position.

```
M & M linker
                                              (SEQ ID NO: 1)
5' GTCGGAGGCCAAGGCGGCCGTACGTCCAACT 3' (31 nt)
                                              (SEQ ID NO: 2)
5' GTTGGACGTACGGCCGCCTTGGCCTCCGAC 3' (31 nt)
5' ends are phosphorylated M & G linker
                                              (SEQ ID NO: 3)
5' GTCGGAGGCCAAGGCGGCCGTACGCTGGAGT 3' (31 nt)
                                              (SEQ ID NO: 4)
5' CTCCAGCGTACGGCCGCCTTGGCCTCCGACT 3' (31 nt)
5' ends are phosphorylated P1 concatenating adapter (PMR 011)
                                              (SEQ ID NO: 5)
5' GGATCCCTTAATCGCCTTGCAGCACATC 3' (28 nt)
                                              (SEQ ID NO: 6)
5' GATGTGCTGCAAGGCGATTAAGGGATCCNN 3' (30 nt)
5' end of top adapter is phosphorylated
5' end of bottom adapter is not phosphorylated P2 concatenating adapter (PMR 012)
                                              (SEQ ID NO: 7)
5' GGATCCCCTGTGTGAAATTGTTATCCGCT 3' (29 nt)
                                              (SEQ ID NO: 8)
5' AGCGGATAACAATTTCACACAGGGGATCCNN 3' (31 nt)
5' end of top adapter is phosphorylated
5' end of bottom adapter is not phosphorylated
```

D1 diPETing adapter (PMR 011)
(SEQ ID NO: 9)
5' <u>GGATCCC</u>TTAATCGCCTTGCAGCACATC 3' (28 nt)
(SEQ ID NO: 10)
5' GATGTGCTGCAAGGCGATTAAGGGATCCNN 3' (30 nt)
5' end of top adapter is phosphorylated
5' end of bottom adapter is not phosphorylated D2 diPETing adapter (PMR 012)
(SEQ ID NO: 11)
5' <u>GGATCC</u>AATGCTCCTCCCTGTGTGAAATTGTTATCCGCT 3'
(39 nt)
(SEQ ID NO: 12)
5' AGCGGATAACAATTTCACACAGGGAGGAGCATTGGATCCNN 3'
(41 nt)
5' end of top adapter is phosphorylated
5' end of bottom adapter is not phosphorylated PMR011 primer
(SEQ ID NO: 13)
5' GATGTGCTGCAAGGCGATTAAG 3' (22 nt)
5' ends are phosphorylated PMR012 primer
(SEQ ID NO: 14)
5' AGCGGATAACAATTTCACACAGG 3' (23 nt)
5' ends are phosphorylated RecA selection oligo
(SEQ ID NO: 15)
5' <u>AGTCGGAGGCCAAGGCGGCCGTACGCTGGAGT</u> 3'
(Biotinylated)

pGIS8 vector
This vector was derived from a pGEM vector
(Promega) and contains the multiple unique cloning
sites for the following restriction enzymes in
this order:
BamH1→Mme1; Cleavable region; Gsu1→BamH1→BseR1

The following oligonucleotides are used:

(SEQ ID NO: 16)
5' AATT<u>GGATCCGACTCGAGGATGAATTCTCCAGGATCCCTCCTC</u> 3'
(43 nt)

(SEQ ID NO: 17)
5' TCGAGAGGAGGGATCCTGGAGAATTCATCCTCGAGTCGGATCC 3'
(43 nt)
5' ends are phosphorylated.

The rest of the vector do not contain any BseR1, BamH1, Mme1 or Gsu1 sites.

The pGIS8 plasmid is one example of a vector that may be used (FIG. 7). The sequence of the sense strand is given in SEQ ID NO:18 and the sequence of the antisense strand is SEQ ID NO:19. A multiple cloning site containing restriction enzyme recognition sites (represented by SEQ ID NOS: 16 and 17) is inserted into the vector. The sequence listing for pGIS8 showing the various restriction enzyme recognition sites are shown in FIG. 11. Any other vector fulfilling the requirements may be prepared and used by any skilled person in the art.

M & M adapter PET
(SEQ ID NO: 20)
5' NNNNNNNNNNNNNNNNNNAGTCGGAGGCCAAGGCGGCCGTACGTCCAAC
TNNNNNNNNNNNNNNNNNNN 3' (69 nt)
(SEQ ID NO: 21)
5' NNNNNNNNNNNNNNNNNNNAGTTGGACGTACGGCCGCCTTGGCCTCCG
ACTNNNNNNNNNNNNNNNNNNN 3' (69 nt)

M & M adapter PET with adapter sequences
(SEQ ID NO: 22)
5' GATGTGCTGCAAGGCGATTAAGGGATCCNNNNNNNNNNNNNNNNNNNN
AGTCGGAGGCCAAGGCGGCCGTACGTCCAACTNNNNNNNNNNNNNNNNNNN
GGATCCCCTGTGTGAAATTGTTATCCGCT 3' (128 nt)
(SEQ ID NO: 23)
5' AGCGGATAACAATTTCACACAGGGGATCCNNNNNNNNNNNNNNNNNNN
AGTTGGACGTACGGCCGCCTTGGCCTCCGACTNNNNNNNNNNNNNNNNNNN
NGGATCCCTTAATCGCCTTGCAGCACATC 3' (128 nt)

M & M final PET
(after cleavage of adapter sequences)
(SEQ ID NO: 24)
5' GATCCNNNNNNNNNNNNNNNNNNNNAGTCGGAGGCCAAGGCGGCCGTA
CGTCCAACTNNNNNNNNNNNNNNNNNNNNG (77 nt)
(SEQ ID NO: 25)
5' GATCCNNNNNNNNNNNNNNNNNNNNAGTTGGACGTACGGCCGCCTTG
GCCTCCGACTNNNNNNNNNNNNNNNNNNNNG 3' (77 nt)

M & G adapter DNA sequences after sonication
(SEQ ID NO: 26)
5' NNNNNNNNNNNNNNNNNNNNNNNAGTCGGAGGCCAAGGCGGCCGTAC
GCTGGAGTNNNNNNNNNNNNNNNNNNNNNNNNNNN 3'
(SEQ ID NO: 27)
5' NNNNNNNNNNNNNNNNNNNNNNNNNNNNNACTCCAGCGTACGGCCG
CCTTGGCCTCCGACTNNNNNNNNNNNNNNNNNNNNNN 3'
(variable nt)

M & G adapter DNA sequences after cloning into
pGIS8 plasmids
(note: rest of the plasmid is not shown)
(SEQ ID NO: 28)
5' GGATCCGACNNNNNNNNNNNNNNNNNNNNNNNNNNNNNNNNNNNN
NNNNNNNAGTCGGAGGCCAAGGCGGCCGTACGCTGGAGTNNNNNNNNNNN
NNNNNNNNNNNNNNNNNNNNNNNNNNNNNNNNCTCCAGGATCC 3'
(140 nt)
(SEQ ID NO: 29)
5' GGATCCTGGAGNNNNNNNNNNNNNNNNNNNNNNNNNNNNNNNNNNN
NNNNNNNACTCCAGCGTACGGCCGCCTTGGCCTCCGACTNNNNNNNNNNN
NNNNNNNNNNNNNNNNNNNNNNNNNNNNNNGTCGGATCC 3'
(140 nt)

M PET intermediate
(SEQ ID NO: 30)
5' GGATCCGACNNNNNNNNNNNNNNNNNNNNNNNNNNNNNNNNNNNNA
GTCGGAGGCCAAGGCGGCCGTACGCTGGAGTNNNNNNNNNNNNNNNNNNN
NNNNNNNNNNNNNNNNNNNNNNNNNNCTCCAGGATCC 3' (132 nt)
(SEQ ID NO: 31)
5' GGATCCTGGAGNNNNNNNNNNNNNNNNNNNNNNNNNNNNNNNNNNN
NNNNNNNNNNNNNNNNNACTCCAGCGTACGGCCGCCTTGGCCTCCGACTN
NNNNNNNNNNNNNNNNNNNNNNNNNNNGTCGGATCC 3' (132 nt)

M and G diPET
(SEQ ID NO: 32)
5' ATCCGACNNNNNNNNNNNNNNNNNNNNNNNNNNNNNNNNNNNNAGT
CGGAGGCCAAGGCGGCCGTACGCTGGAGTNNNNNNNNNNNNNNNNNNNNN
NNNNNNNCTCCAGGATCC 3' (116 nt)
(SEQ ID NO: 33)
5' GGATCCTGGAGNNNNNNNNNNNNNNNNNNNNNNNNNNNNACTCAGCGTA
CGGCCGCCTTGGCCTCCGACTNNNNNNNNNNNNNNNNNNNNNNNNNNNNN
NNNNNNNNNNNGTCGGATC 3' (116 nt)

Released diPET with BamH1 sticky ends
(SEQ ID NO: 34)
5' GATCCGACNNNNNNNNNNNNNNNNNNNNNNNNNNNNNNNNNNNNNAG
TCGGAGGCCAAGGCGGCCGTACGCTGGAGTNNNNNNNNNNNNNNNNNNN
NNNNNNNNCTCCAG 3' (111 nt)
(SEQ ID NO: 35)
5' GATCCTGGAGNNNNNNNNNNNNNNNNNNNNNNNNNNNNNNNACTCCAGC
GTACGGCCGCCTTGGCCTCCGACTNNNNNNNNNNNNNNNNNNNNNNNNN
NNNNNNNNNNNGTCG 3' (111 nt)

M & M adapter PET before MmeI digestion
(SEQ ID NO: 36)
5' NNNNNNNNNNNNNNNNNNNNNNNNNNNNNNNNAGTCGGAGGCAAGGCGGC
CGTACGTCCAACTNNNNNNNNNNNNNNNNNNNNNNNNNNNNNNNNN 3'
(91 nt)
(SEQ ID NO: 37)
5' NNNNNNNNNNNNNNNNNNNNNNNNNNNNNNNTCAGCCTCCGGTTCCGCCG
GCATGCAGGTTGANNNNNNNNNNNNNNNNNNNNNNNNNNNNNNNN 3'
(91 nt)

-continued

Figure 8:
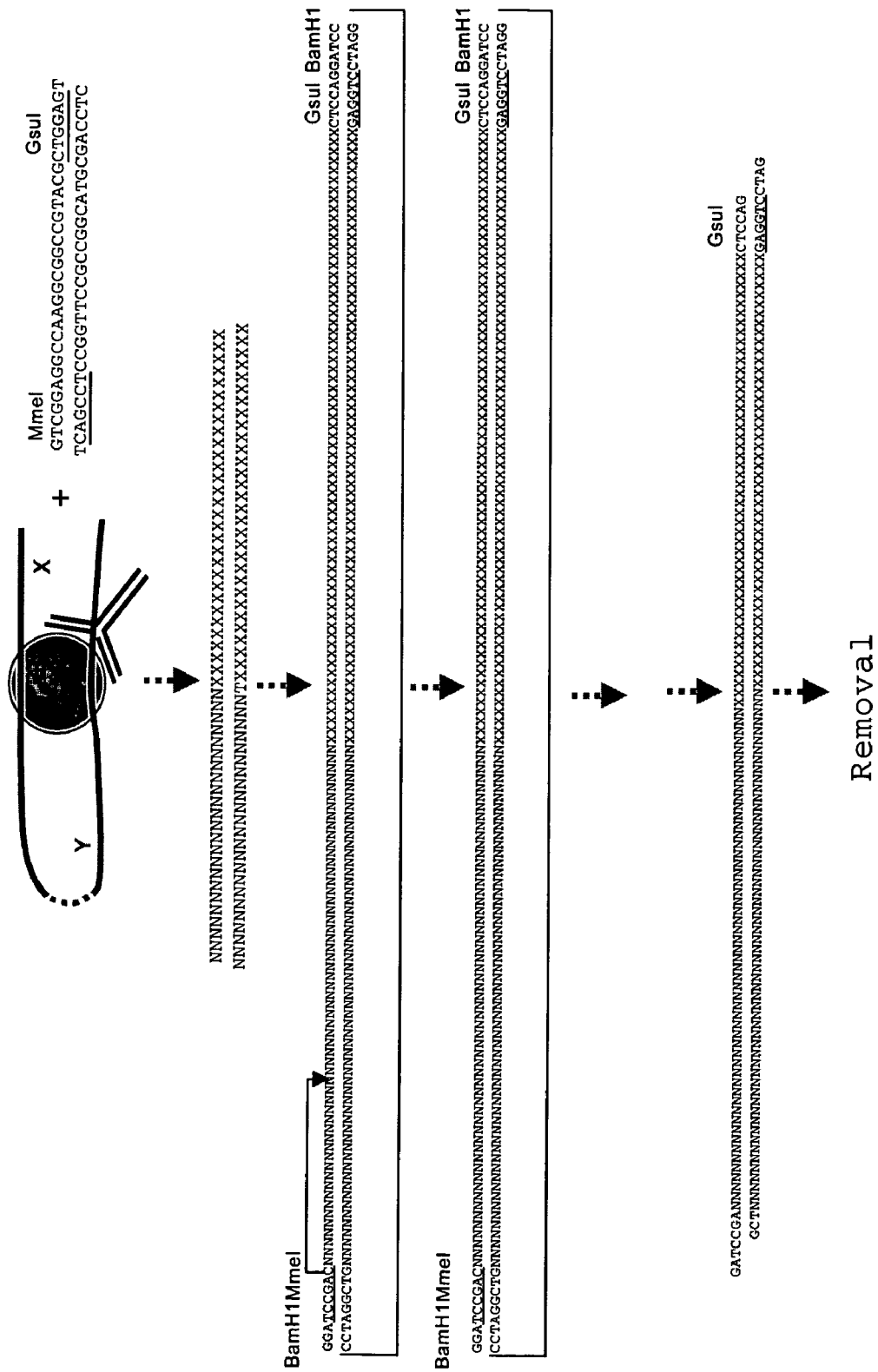
FIG. 8 illustrates how oligonucleotides that do not have a linker inserted will not be cut by the restriction enzymes and hence are too long and will be removed by electrophoresis. The sequences which appear in the figure from top to bottom are as follows: SEQ ID NO:3, SEQ ID NO:4, SEQ ID NO:38, SEQ ID NO:39, SEQ ID NO:40, SEQ ID NO:41, SEQ ID NO:42, SEQ ID NO:43, SEQ ID NO:44 and SEQ ID NO:45.

Oligonucleotide of FIG. 8 before insertion of
M & G linker
(SEQ ID NO: 38)
5' NNNNNNNNNNNNNNNNNNNNNNNNNNNNNNNNNNNNNNNNNNNNNNNN
NNNNNNN 3' (53 nt)
(SEQ ID NO: 39)
5' NNNNNNNNNNNNNNNNNNNNNNNNNNNNTNNNNNNNNNNNNNNNNNN
NNNNNNN 3' (53 nt)

Oligonucleotide of FIG. 8 inserted into plasmid
(rest of plasmid not shown)
(SEQ ID NO: 40)
5' GGATCCGACNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNCTCCAGGATCC 3'
(140 nt)
(SEQ ID NO: 41)
5' GGATCCTGGAGNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNGTCGGATCC 3'
(140 nt)

Oligonucleotide of FIG. 8 inserted into plasmid
(rest of plasmid not given)
(SEQ ID NO: 42)
5' GGATCCGACNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNCTCCAGGATCC 3'
(140 nt)
(SEQ ID NO: 43)
5' GGATCCTGGAGNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNNNNNNNNNNNNNNNNNNNGTCGGATCC 3'
(140 nt)

Oligonucleotide of FIG. 8 without M & G linker
inserted removed by electrophoresis
(SEQ ID NO: 44)
5' GATCCGANNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNCTCCAG 3' (112 nt)
(SEQ ID NO: 45)
5' GATCCTGGAGNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNNNTCG 3' (112 nt)

Figure 9:
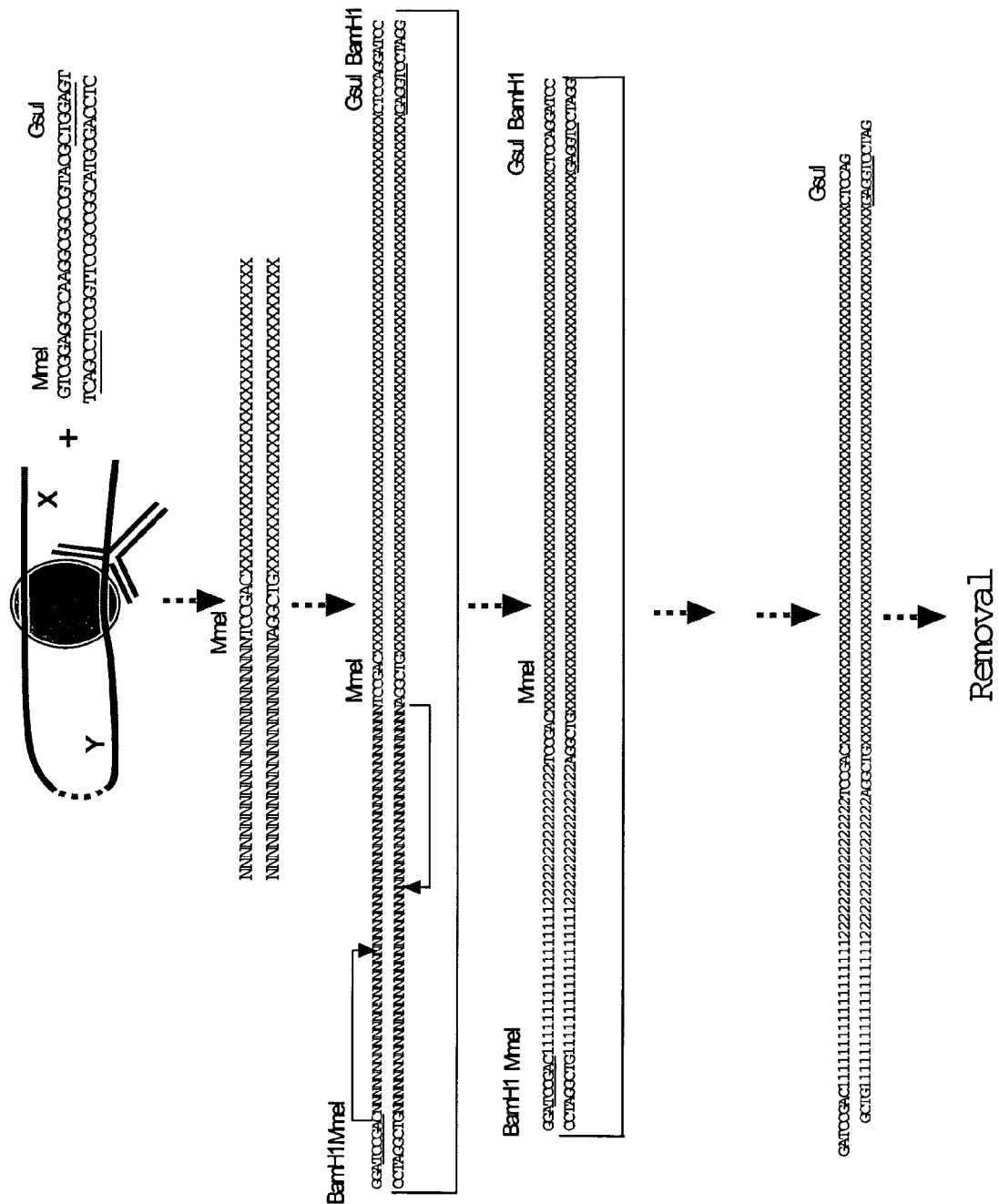
FIG. 9 illustrates how if only a part of a linker is inserted into an oligonucleotide, it will result in that oligonucleotide that is incorrectly cut and hence will be removed by electrophoresis as it will be too long. The sequences which appear in the figure from top to bottom are as follows: SEQ ID NO:3, SEQ ID NO:4, SEQ ID NO:46, SEQ ID NO:47, SEQ ID NO:48, SEQ ID NO:49, SEQ ID NO:50, SEQ ID NO:51, SEQ ID NO:52 and SEQ ID NO:53.

Oligonucleotide of FIG. 9 before insertion of
M & G linker
(SEQ ID NO: 46)
5' NNNNNNNNNNNNNNNNNNNNNNNNNNTCCGACNNNNNNNNNNNNNNNN
NNNNNNNNNNNN 3' (59 nt)
(SEQ ID NO: 47)
5' NNNNNNNNNNNNNNNNNNNNNNNNNNNNGTCGGANNNNNNNNNNNN
NNNNNNNNNNNN 3' (59 nt)

Oligonucleotide of FIG. 9 after insertion of part
of M & G linker
(SEQ ID NO: 48)
5' GGATCCGACNNNNNNNNNNNNNNNNNNNNNNNNNNNNNNNNNNNNNNN
NNNNNNNNNNNTCCGACNNNNNNNNNNNNNNNNNNNNNNNNNNNNNNNNNN
NNNNNNNNNNNNNNNNNNNNNNNNNNNNNNCTCCAGGATCC 3'
(140 nt)
(SEQ ID NO: 49)
5' GGATCCTGGAGNNNNNNNNNNNNNNNNNNNNNNNNNNNNNNNNNNNNN
NNNNNNNNNNNNNNNNNNNNNNNNNNNGTCGGANNNNNNNNNNNNNNNN
NNNNNNNNNNNNNNNNNNNNNNNNNNNNNNGTCGGATCC 3'
(140 nt)

Oligonucleotide of FIG. 9 with partial M & G
linker inserted after restriction enzyme digest
(rest of plasmid not given)
(SEQ ID NO: 50)
5' GGATCCGACNNNNNNNNNNNNNNNNNNNNNNNNNNNNNNNNNNNTCC
GACNNNNNNNNNNNNNNNNNNNNNNNNNNNNNNNNNNNNNNNNNNNNNNN
NNNNNNNNNNNNNNNNNNNNNNNNCTCCAGGATCC 3' (126 nt)
(SEQ ID NO: 51)
5' GGATCCTGGAGNNNNNNNNNNNNNNNNNNNNNNNNNNNNNNNNNNNNN
NNNNNNNNNNNNNNNNNNNNNNNNNNNNNNNNGTCGGANNNNNNNNNNNN
NNNNNNNNNNNNNNNNNNNNNNNGTCGGATCC 3' (126 nt)

Oligonucleotide of FIG. 9 after excision from
plasmid
(SEQ ID NO: 52)
5' GATCCGACNNNNNNNNNNNNNNNNNNNNNNNNNNNNNNNNNNNNTCCG
ACNNNNNNNNNNNNNNNNNNNNNNNNNNNNNNNNNNNNNNNNNNNNNNNN
NNNNNNNNNNNNNNNNNNNNCTCCAG 3' (120 nt)
(SEQ ID NO: 53)
5' GATCCTGGAGNNNNNNNNNNNNNNNNNNNNNNNNNNNNNNNNNNNNNN
NNNNNNNNNNNNNNNNNNNNNNNNNNNNNNGTCGGANNNNNNNNNNNNN
NNNNNNNNNNNNNNNNNNNNGTCG 3' (120 nt)

Figure 10:
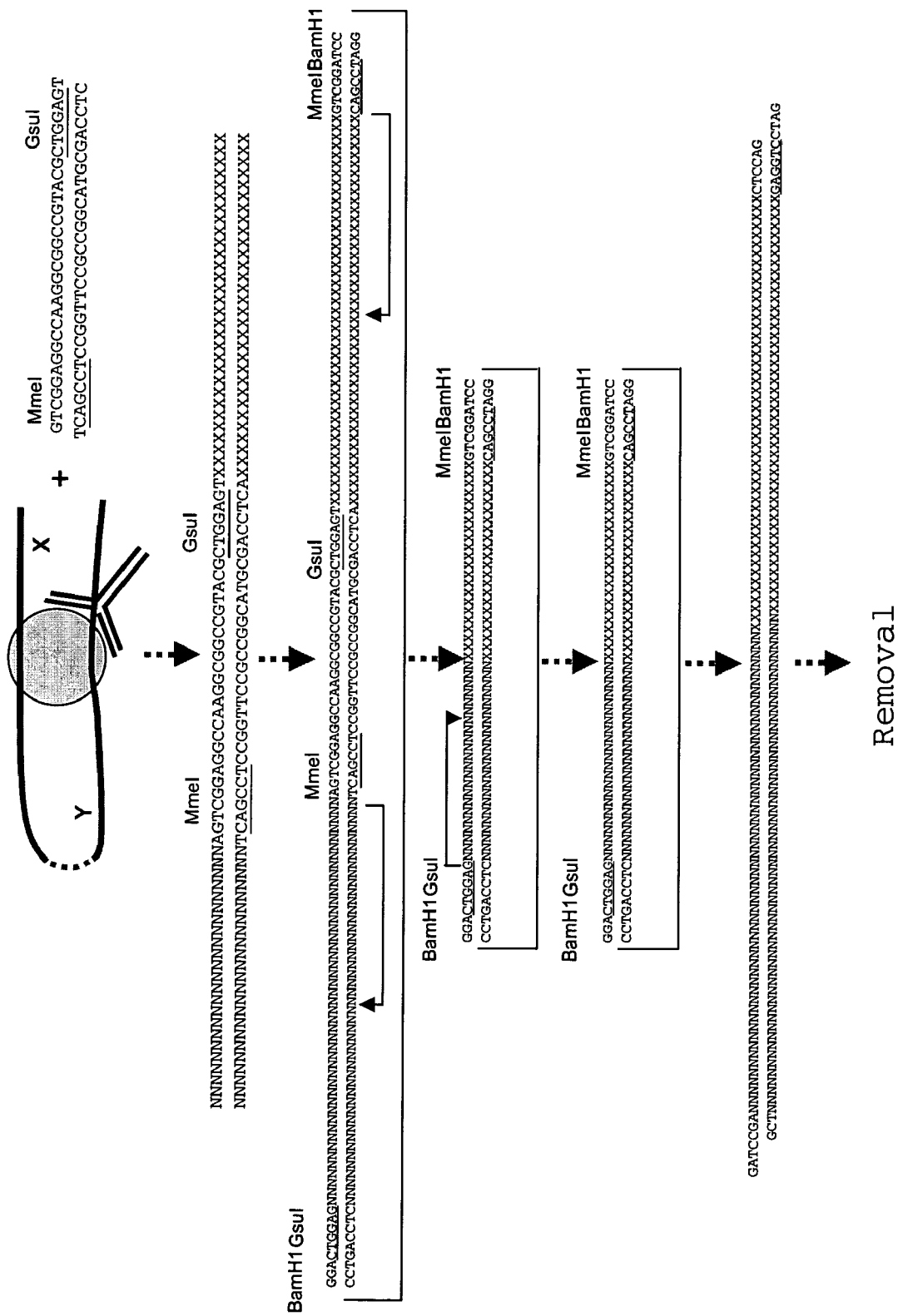
FIG. 10 illustrates how an incorrectedly inserted linker will give rise to oligonucleotides that are too long and variable in length and hence can be removed by electrophoresis. The sequences which appear in the figure from top to bottom are as follows: SEQ ID NO:3, SEQ ID NO:4, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62 and SEQ ID NO:63.

Oligonucleotide of FIG. 10 with M & G linker
inserted into the opposite orientation
(SEQ ID NO: 54)
5' NNNNNNNNNNNNNNNNNNNNNNNNNNNAGTCGGAGGCCAAGGCGGCCGTAC
GCTGGAGTNNNNNNNNNNNNNNNNNNNNNNNNNNNN 3' (85 nt)
(SEQ ID NO: 55)
5' NNNNNNNNNNNNNNNNNNNNNNNNNNNNNACTCCAGCGTACGGCCG
CCTTGGCCTCCGACTNNNNNNNNNNNNNNNNNNNNNN 3' (85 nt)

Oligonucleotide of Fig. 10 inserted into plasmid
(rest of plasmid not given)
(SEQ ID NO: 56)
5' GGACTGGAGNNNNNNNNNNNNNNNNNNNNNNNNNNNNNNNNNNNNNN
NNNNNNNAGTCGGAGGCCAAGGCGGCCGTACGCTGGAGTNNNNNNNNNNN
NNNNNNNNNNNNNNNNNNNNNNNNNNNNNNNNNNNNNNNNNNNNGTCGGATC
C 3' (148 nt)
(SEQ ID NO: 57)
5' GGATCCGACNNNNNNNNNNNNNNNNNNNNNNNNNNNNNNNNNNNNNN
NNNNNNNNNNNNNNNACTCCAGCGTACGGCCGCCTTGGCCTCCGACTNNN
NNNNNNNNNNNNNNNNNNNNNNNNNNNNNNNNNNNNNNNNNNNCTCCAGTC
C 3' (148 nt)

Intermediate oligonucleotide 1 of FIG. 10
(SEQ ID NO: 58)
5' GGACTGGAGNNNNNNNNNNNNNNNNNNNNNNNNNNNNNNNNNNNNNN
NNNNNNGTCGGATCC 3' (62 nt)
(SEQ ID NO: 59)
5' GGATCCGACNNNNNNNNNNNNNNNNNNNNNNNNNNNNNNNNNNNNNN
NNNNNNCTCCAGTCC 3' (62 nt)

Intermediate oligonucleotide 2 of FIG. 10
(SEQ ID NO: 60)
5' GGACTGGAGNNNNNNNNNNNNNNNNNNNNNNNNNNNNNNNNNNNNNN
NNNNN 3' (62 nt)
(SEQ ID NO: 61)
5' GGATCCGACNNNNNNNNNNNNNNNNNNNNNNNNNNNNNNNNNNNNNN
NNNNNNCTCCAGTCC 3' (62 nt)

Product oligonucleotide of FIG. 10
(SEQ ID NO: 62)
5' GATCCGANNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNCTCCAG 3' (114 nt)
(SEQ ID NO: 63)
5' GATCCTGGAGNNNNNNNNNNNNNNNNNNNNNNNNNNNNNNNNNNNNNN
NNNNNNNNNNNNNNNNNNNNNNNNNNNNNNNNNNNNNNNNNNNNNNNNNNN
NNNNNNNNNNNNNTCG 3' (114 nt)

Example 1

Protocol for CIA-PET Using Mouse Embryonic
Stem Cells

The CIA-PET method (FIGS. 1 and 4) comprises five sections: (1) Generate ChIP DNA-protein-DNA complex, (2) Prepare CIA-PET, (3) Amplify CIA-PET, (4) Sequence CIA-PET, and (5) Map the CIA-PET sequences. (FIG. 3)

(1) Generate ChIP DNA-Protein-DNA Complex (a) Mouse embryonic stem (ES) cells are cultured under feeder-free conditions in the presence of leukemia inhibitory factor (Chemicon).

(b) About 1 to $2\times10^8$ cells are collected and crosslinked with formaldehyde (final concentration of 1%; Sigma) for 10 minutes at room temperature.

(c) Cell lysis and chromatin preparation:
  c1. Cells are lysed in lysis buffer (50 mM HEPES, 1 mM EDTA, 0.15 M NaCl, 1% SDS, 1% Triton X-100, 0.1% sodium deoxycholate, all from Ambion).
  c2. The chromatin is solubilized by sonication using a Branson 450 ultrasonic cell disruptor (20% duty power output, 30 second, 5 to 8 times;).
  c3. The chromatin is diluted 10 times to lower the SDS to 0.1%.
  c4. The extract is then cleared by centrifugation at 14,000 rpm for 10 minutes at 4 C.
  c5. This extract is stored at −80 C. until use.
(d) Immuno-precipitation
  d1. Two microgrammes of monoclonal antibody (F7, Santa Cruz) are bound to protein G sepharose (Pharmacia).
  d2. The antibody coated beads are incubated with the chromatin extract at 4° C. for 16 hours.
  d3. The beads are then washed with the following buffers (reagents from Sigma Chemical Company):
    Wash buffer 1 (50 mM HEPES, 1 mM EDTA, 0.15 M NaCl, 0.1% SDS, 1% Triton X-100, 0.1% sodium deoxycholate) 2 times
    Wash buffer 2 (50 mM HEPES, 1 mM EDTA, 0.5 M NaCl, 0.1% SDS, 1% Triton X-100, 0.1% sodium deoxycholate) 1 time
    Wash buffer 3 (20 mM Tris.HCl pH 8.0, 1 mM EDTA, 0.25 M LiCl, 0.5% NP40, 0.5% sodium deoxycholate) 1 time
    Wash buffer 4 (20 mM Tris.HCl pH 8.0, 1 mM EDTA) 1 time
  d4. The protein-DNA complexes are then eluted from the beads with elution buffer (50 mM Tris.HCl pH 8.0, 1 mM EDTA, 1% SDS) for 20 min at 65° C.
  d5. The eluant is then dialyzed in PBS (Ambion) to remove SDS for 3 hours at 4° C.

(2) Prepare CIA-PET (a) End Repair

Perform end-repair with the Epicentre End-It kit and chemicals:

| | |
|---|---|
| Chromatin (up to 5 ug) | 2.5 ul 10× |
| End Repair Buffer | 5 ul |
| 2.5 mM dNTP Mix | 5 ul |
| 10 mM ATP | 5 ul |
| End-Repair Enzyme Mix | 1 ul |
| Nuclease free water | to 50 ul |

Vortex briefly to mix and then incubate at room temperature for 45 minutes, stop reaction by heating at 70° C. for 10 minutes. Adjust the concentration to 65 ng/ul by adding 27 ul of nuclease free water.

(b) A-Tailing

| | |
|---|---|
| DNA | 20 ul |
| 10 mM dATP (Roche) | 0.5 ul |
| 10× ExTaq buffer (Takara) | 2.5 ul |
| ExTaq polymerase (Takara) | 0.5 ul |
| Nuclease free water | to 25 ul |

Incubate in a PCR machine at 72° C. for 30 min, then 4° C. It is best to take out the tubes and perform the ligation immediate once incubation at 72° C. ends.

(c) Ligate DNA with M&M Linker (SEQ ID NOS: 1 and 2)

| | |
|---|---|
| Chromatin DNA (200 ug) | 3.1 ul |
| M&M adapter-T tailed (38 ng) | 3.1 ul |
| 5X ligase buffer with PEG (Invitrogen) | 6 ul |
| T4 ligase (5 U/ul) (Invitrogen) | 1 ul |
| Nuclease free water | 12.3 ul |

Ligate overnight at 16° C. to obtain oligonucleotides (SEQ ID NOS: 20 and 21) inserted with M&M linker.

(d) Reverse Cross-Links with Proteinase K

Divide DNA sample into 20 ul aliquots, and reverse cross-links by overnight incubation at 65° Celsius in the presence of 15 ul of 20 mg/ml proteinase K (Ambion). The next day, add 1 ul of 10 mg/ml RNAse A (Qiagen) to degrade RNA is degraded 45 min at 37° Celsius, followed by phenol extraction and ethanol precipitation of DNA. Resuspend in 20 ul of Elution Buffer and store at −20° C. The concentration obtained is usually 500 ng/ul.

Quantitate DNA and perform quality control by running 0.5 ul of the DNA obtained on a 1% gel with Takara Wide-Range Ladders and Invitrogen Low-Mass ladders and 0.5 ul of material from (a). The material from (d) should be less smeared on the gel and should not show any bright band at around the 50-100 bp mark.

(e) Mme1 Cut

| | |
|---|---|
| 10 ug DNA | 20 ul |
| 10× NEBuffer4 (New England Biolabs) | 20 ul |
| 10× SAM (New England Biolabs) | 20 ul |
| Mme1 (2 U/ul) (New England Biolabs) | 20 ul |
| Nuclease-free water | 120 ul |

Split into two tubes and incubate overnight at 37° C. SAM should be prepared fresh.

Phenol chloroform and ethanol precipitation with glycoblue.

Quantitate DNA and perform quality control by running 3 ul on a 2% gel or PAGE gel together with Takara Wide-Range Ladders and Invitrogen Low-Mass ladders and with 0.5 ul of material from step (d).

(f) Gel Purification

Load DNA obtained onto a 2% agarose gel in a Scie-Plas medium-sized unit (60 ul per well) together with appropriate ladders, eg 20 ul of Takara Wide Range ladder. Run at 80V, approximately 1.5 hours, and visualize at 365 nm UV. Oligonucleotides with incorrectly inserted linkers will be removed by the gel electrophoresis (for examples of incorrectly inserted linkers, see FIGS. 8 to 10). Excise ditag band and electroelute using disposable Fermentas ElutaTubes according to manufacturer's recommendations. Electroelution is performed for 1-1.5 hours at 90 V and the harvested ditags are ethanol precipitated thus:

For every 200 ul eluate, add

| | |
|---|---|
| 3 M NaOAc pH 5.2 (Amresco) | 20 ul |
| 1 M MgCl2 (Ambion) | 4.5 ul |
| Glycoblue (Ambion) | 2 ul |
| 100% ethanol | 800 ul |

Resuspend precipitated ditags in 12 ul Elution Buffer (Qiagen) and run 2-5 ul on a 4-20% PAGE minigel together with Low Mass Ladders (Invitrogen) for purity check and visual quantification. Correctly obtained ditags have the sequences given in SEQ ID NOS: 22 and 23).

(3) Amplify PET (a) Adapter Ligation (Concatenating Adaptors SEQ ID NOS: 5 to 8)

| | |
|---|---|
| DNA (100 ng) | 6 ul |
| Adapter (10 ug) | 6 ul |
| 10× ligase buffer (with spermidine) | 1.5 ul |
| T4 DNA ligase (5 U/ul, Invitrogen) | 1 ul |
| Nuclease Free Water | 0.5 ul |

The total volume is 15 ul. Incubate at 16° C. for 16 hours. 10× ligation buffer with Spermidine is made up of:
60 mM Tris-HCl pH7.5 (Ambion)
60 mM MgCl2 (Ambion)
50 mM NaCl (Ambion)
1 mg/ml BSA (New England Biolabs)
70 mM Beta-mercaptoethanol (Sigma)
1 mM ATP (Invitrogen)
20 mM DTT (Invitrogen)
10 mM spermidine (Sigma)

(b) PCR Amplification

Amplify with primers PMRs 11 and 12 (SEQ ID NOS: 13 and 14 respectively) and the Hotstartaq kit from Qiagen:

| | |
|---|---|
| DNA | 1 ul |
| 10× PCR buffer (Qiagen) | 10 ul |
| dNTP mix (10 mM of each) (Invitrogen) | 2 ul |
| PMR11 | 1 ul (0.2 uM) |
| PMR12 | 1 ul (0.2 uM) |
| HotStarTaq DNA Polymerase (Qiagen) | 0.5 ul |
| Nuclease Free Water | to 100 ul |

Mix well. Incubate in PCR machine:
1. 15 minutes, 95° C.
2. 0.5 min 94° C.
3. 0.5 min 55° C.
4. 1 min 72° C.
5. Repeat from step 2 25 times.
6. 10 min 72° C.

Purify using PCR purification kit (Qiagen).

(4) Sequence the CIA-PETs

The CIA-PETs may be directly sequenced according to the protocols for the 454 multiplex sequencing machine (454 life sciences). The technique is taught in Margulies et al (2005) and US Application No. 20030068629. These references are hereby incorporated in their entirety by reference.

(5) Map the CIA-PETs

Mapping may be performed using the Compressed Suffix Array. Multiple joins across two different DNA fragments (n>3) shall be taken to represent real distal control regions (FIG. 3).

Example 3

Method of CIA-diPET

The CIA-diPET method (FIGS. 2 and 6). comprises the following sections: (1) Generate ChIP DNA-protein-DNA complex, (2) Prepare CIA library (3) Prepare CIA-PET library (4) Sequence and (5) Map the CIA-PET sequences (FIG. 5).

(1) Generate ChIP DNA-Protein-DNA Complex (as Above)

(a) Mouse embryonic stem (ES) cells are cultured under feeder-free conditions in the presence of leukemia inhibitory factor (Chemicon).

(b) About 1 to $2 \times 10^8$ cells are collected and crosslinked with formaldehyde (final concentration of 1%; Sigma) for 10 minutes at room temperature.

(c) Cell lysis and chromatin preparation:
  c1. Cells are lysed in lysis buffer (50 mM HEPES, 1 mM EDTA, 0.15 M NaCl, 1% SDS, 1% Triton X-100, 0.1% sodium deoxycholate, all from Ambion).
  c2. The chromatin is solubilized by sonication using a Branson 450 ultrasonic cell disruptor (20% duty power output, 30 second, 5 to 8 times;).
  c3. The chromatin is diluted 10 times to lower the SDS to 0.1%.
  c4. The extract is then cleared by centrifugation at 14,000 rpm for 10 minutes at 4 C.
  c5. This extract is stored at −80 C until use.

(d) Immuno-Precipitation
  d1. Two micrograms of monoclonal antibody (F7, Santa Cruz) are bound to protein G sepharose (Pharmacia).
  d2. The antibody coated beads are incubated with the chromatin extract at 4° C. for 16 hours.
  d3. The beads are then washed with the following buffers (reagents from Sigma Chemical Company):
    Wash buffer 1 (50 mM HEPES, 1 mM EDTA, 0.15 M NaCl, 0.1% SDS, 1% Triton X-100, 0.1% sodium deoxycholate) 2 times
    Wash buffer 2 (50 mM HEPES, 1 mM EDTA, 0.5 M NaCl, 0.1% SDS, 1% Triton X-100, 0.1% sodium deoxycholate) 1 time
    Wash buffer 3 (20 mM Tris.HCl pH 8.0, 1 mM EDTA, 0.25 M LiCl, 0.5% NP40, 0.5% sodium deoxycholate) 1 time
    Wash buffer 4 (20 mM Tris.HCl pH 8.0, 1 mM EDTA) 1 time
  d4. The protein-DNA complexes are then eluted from the beads with elution buffer (50 mM Tris.HCl pH 8.0, 1 mM EDTA, 1% SDS) for 20 min at 65° C.
  d5. The eluant is then dialyzed in PBS (Ambion) to remove SDS for 3 hours at 4° C.

(2) Prepare CIA-diPET Library (a) End repair (as for preparation of CIA-PET), perform end-repair with the Epicentre End-It kit:

| | |
|---|---|
| Chromatin (up to 5 ug) | 2.5 ul |
| 10× End Repair Buffer (Epicentre) | 5 ul |
| 2.5 mM dNTP Mix (Epicentre) | 5 ul |
| 10 mM ATP (Epicentre) | 5 ul |
| End-Repair Enzyme Mix (Epicentre) | 1 ul |
| Nuclease Free Water | 31.5 ul |

Briefly vortex to mix, then incubate at room temperature for 45 minutes, stop by heating at 70° C. for 10 minutes. Adjust the concentration to 65 ng/ul by adding 27 ul of Nuclease Free Water.

(b) A-tailing, as above for CIA-PET

| | |
|---|---|
| DNA | 20 ul |
| 10 mM dATP (Roche) | 0.5 ul |
| 10× ExTaq buffer (Takara) | 2.5 ul |
| ExTaq polymerase (Takara) | 0.5 ul |
| Nuclease Free Water | 1.5 ul |

Incubate in a PCR machine at 72° C. for 30 minutes, then 4° C. forever. It is best to take out the tubes and perform the ligation immediately once the incubation at 72° C. ends.

(c) Ligate DNA with M&G linker (SEQ ID NOS: 3 and 4)

| | |
|---|---|
| Chromatin DNA (200 ng) | 3.1 ul |
| M&G adapter-T tailed (38 ng) | 7.6 ul |
| 5× ligase buffer with PEG (Invitrogen) | 6 ul |
| T4 ligase (5 U/ul) (Invitrogen) | 1 ul |
| Final volume | 12.3 ul |

Ligate overnight at 16° C. to obtain oligonucleotides (SEQ ID NOS: 26 and 27) inserted with M&G linker.

(d) Reverse cross-links with proteinase K, as above for CIA-PET.

Divide DNA sample into 20 ul aliquots, and reverse cross-links by overnight incubation at 65 Celsius in the presence of 15 ul of 20 mg/ml proteinase K (Ambion). The next day, add 1 ul of 10 mg/ml RNAse A (Qiagen) to degrade RNA is degraded 45 min at 37° Celsius, followed by phenol extraction and ethanol precipitation of DNA. Resuspend in 20 ul of Elution Buffer and store at −20° C. The concentration is usually 500 ng/ul.

Quantitate and perform quality control check by running 0.5 ul on a 1% gel together with Takara Wide-Range Ladders and Invitrogen Low-Mass ladders and 0.5 ul of material from (a). The material from (d) should be less smeared out on the gel as well as not show any bright band at around the 50-100 bp mark.

(e) Digest with NIa III

Store NIa III at −80° C. (half-life is 6 months at −80° C.). Place on ice just before use.

| | |
|---|---|
| DNA (approximately 1 ug) | 2 ul |
| 10× NEBuffer 4 (New England Biolabs) | 5 ul |
| NlaIII (New England Biolabs) | 1 ul |
| 100× BSA (New England Biolabs) | 0.5 ul |
| Nuclease-Free Water | 41.5 ul |

Prepare five tubes of the above reaction. Incubate for 1 hour at 37° C. Phenol chloroform ethanol precipitate with glycoblue, resuspend in 10 ul of Elution Buffer (Qiagen).

(f) Polish ends with the Epicentre End-It kit:

| | |
|---|---|
| DNA (up to 5 ug) | 34 ul |
| 10× End Repair Buffer (Epicentre) | 5 ul |
| 2.5 mM dNTP Mix (Epicentre) | 5 ul |
| 10 mM ATP (Epicentre) | 5 ul |
| End-Repair Enzyme Mix (Epicentre) | 1 ul |

Incubate at room temperature for 45 minutes; stop by heating at 70° C. for 10 minutes.

(i) Clone into a pGIS8 vector (SEQ ID NOS: 18 and 19; FIGS. 7 and 11) with Mme1 and Gsu1 flanking sites Set up on ice, using 1.7 ml microfuge tubes (use multiple tubes):

| | |
|---|---|
| 40 ng/ul precut pGIS DNA | 1 ul 6 ul |

| | |
|---|---|
| 5× ligase buffer with PEG (Invitrogen) | 2 ul |
| T4 DNA ligase (5 U/ul) (Invitrogen) | 1 ul |

Incubate overnight (12-16 hours) at 16° C. to obtain oligonucleotides represented by SEQ ID NOS: 28 and 29).

Also set up a vector self-ligation control.

Transform 1 µl of the ligation reaction per 50 µl of electrocompetent TOP10 cells (Invitrogen) by electroporation. Recover each aliquot in 1 ml LB media at 37° C. for 1 hr, then plate out in a series of several dilutions (on LB agar+ampicillin) for quality control and titering.

Then scale up this process by plating the remaining culture on large agar plates (Q-trays), and performing maxipreps using the Qiagen HiSpeed Plasmid Maxi kit.

(3) CIA-diPET Library (a) Mme1 Cut

| | |
|---|---|
| 10 ug DNA | 100 ul |
| 10× NEBuffer 4 (New England Biolabs) | 20 ul |
| 10× SAM (New England Biolabs) | 20 ul |
| Mme1 (2 U/ul) (New England Biolabs) | 12 ul |
| Nuclease-free water | 48 ul |

Incubate overnight at 37° C. to obtain oligonucleotides represented by SEQ ID NOS: 30 and 31. SAM should be prepared fresh.

Phenol chloroform and ethanol precipitation with glycoblue, resuspend in 12 ul of Elution Buffer.

Quantitate DNA and perform quality control check by running 1 ul on a 2% gel or PAGE gel together with Takara Wide-Range Ladders and Invitrogen Low-Mass ladders and with 1 ul of material from step (e).

(b) Circularization

Set up a 96 well plate with each well containing the following (MJ Research):

| | |
|---|---|
| 100 ng DNA | 50 ul |
| Ligation Solution 1 (Takara Ligation Kit ver 2) | 50 ul |
| Seal plate tightly to prevent evaporation. | |
| Incubate at 16° C., overnight. | |

Perform PCR purification (Qiagen) with three columns, resuspending in 40 ul of Elution Buffer each, giving rise to a total of approximately 120 ul.

(c) Gsu1 Cut

Set up 9 tubes of:

| | |
|---|---|
| Circularized DNA | 12 ul |
| 10× buffer TANGO (Fermentas) | 8.6 ul |
| 10× SAM (New England Biolabs) | 8.6 ul |
| Gsu1 (5 U/ul) (Fermentas) | 1 ul |
| Nuclease Free Water | 55.8 ul |

Digest at 30° C. for at least 2 h, but do not cut overnight. Oligonucleotides represented by SEQ ID NOS: 32 and 33 are obtained, (d) Circularization
Set up 9 tubes containing the following:

| | |
|---|---|
| Approx 100 ng DNA | 50 ul |
| Ligation Solution 1 (Takara Ligation Kit ver 2) | 50 ul |

Incubate at 16° C., overnight.
Phenol chloroform ethanol precipitate, resuspend in 12 ul of Elution Buffer.
(e) Amplification with Rolling Circle Amplification (Templiphi kit, Amersham)
Thaw solutions on ice. Prepare 3-4 tubes of the following:

| | |
|---|---|
| 2.5 ng of DNA | 1 ul |
| Templiphi kit denature buffer (Amersham) | 10 ul |

Heat at 95° C. for 3 minutes, then briefly cool on ice.
To the reaction buffer, add:

| | |
|---|---|
| Templiphi kit premix (Amersham) | 10 ul |

Mix well by tapping or gentle vortexing.
Incubate at 30° C., no shaking, 16-18 hours.
Examine the material, for example, by micropipetting 1 ul. It should be viscous.
Quantitate double-stranded DNA by picogreen fluorimetry (Quant-iT DNA assay kit, Molecular Probes)
(f) BamH1 Cut

| | |
|---|---|
| 100 ug DNA | 1 ul |
| 10× unique BamHl buffer (New England Biolabs) | 10 ul |
| 100× Bovine Serum Albumin (New England Biolabs) | 1 ul |
| BamHl (20 U/ul; 2-fold excess) (New England Biolabs) | 10 ul |
| Nuclease Free Water | 78 ul |

Prepare more tubes as needed to digest the DNA; incubate at 37° C. overnight to obtain oligonucleotides represented by SEQ ID NOS: 34 and 35.
(g) Gel Purification
Load onto a 2% agarose gel in a Scie-Plas medium-sized unit (60 ul per well) together with appropriate ladders, eg 20 ul of Takara Wide Range ladder. Run at 80V, approximately 1.5 hours, and visualize at 365 nm UV. Oligonucleotides with incorrectly inserted linkers will be removed by the gel electrophoresis (for examples of incorrectly inserted linkers, see FIGS. 8 to 10).
Excise ditag band and electroelute using disposable Fermentas ElutaTubes according to manufacturer's recommendations. Electroelution is performed for 1-1.5 hours at 90 V and the harvested ditags are ethanol precipitated thus:
For every 200 ul eluate, add

| | |
|---|---|
| 3 M NaOAc pH 5.2 | 20 ul |
| 1 M MgCl2 | 4.5 ul |
| Glycoblue | 2 ul |
| 100% ethanol | 800 ul |

Resuspend precipitated diPETs in 12 ul Elution Buffer and run 2-5 ul on a 4-20% PAGE minigel together with Low Mass Ladders (Invitrogen) for purity check and visual quantification.
(4) Sequence the CIA-diPET
(a) Concatenation of Gel-Purified BamHI-Cohesive diPETs:

| | |
|---|---|
| CIA-diPETs 200-1000 ng | 6 ul |
| 10× ligase buffer (with spermidine) | 1 ul |
| T4 DNA ligase (5 U/ul) (Invitrogen) | 1 ul |
| Nuclease Free Water | 2 ul |

Incubate at 16° C. for 2 hrs to overnight. Then heat-inactivate at 65° C. for 10 min.
(b) Partial BamHI Redigestion of CIA-diPET Concatemers
Purify the concatemer DNA using the Qiagen PCR purification QuickSpin kit. Then quantitate the DNA by using 1 ul for Nanodrop (Nanodrop technologies), and do a short BamHI re-digest:

| | |
|---|---|
| Concatemers | 20 ul |
| 10× BamHI buffer (New England Biolabs) | 3 ul |
| BamHI (diluted to 1 U/ul) (New England Biolabs) | 0.2 ul |
| 100× BSA (New England Biolabs) | 0.5 ul |
| Nuclease Free Water | 6.3 ul |

Incubate at 37° C. for 30 min, not any longer.
Quickly add 6 ul of loading dye, heat at 65° C. for 15 min and chill on ice before loading on PAGE gel.
(c) PAGE Purification of Concatenated CIA-diPETs
Load the entire sample preferably into 1 well of a 4-20% gradient PAGE minigel, flanked by Takara Wide-Range and Invitrogen Low Mass ladders to allow sizing. Electrophorese at 200V for about 1 hr. Stain for 15-30 min in SYBR Green I, and visualize on the Dark Reader transilluminator (Clare Chemical) for gel excision.
(d). Excision of Concatemers
Excise the concatenated DNA in 3 separate fractions, low (400-1000 bp); medium (1000-2000 bp) and high (>2000 bp). Place the gel slice of each excised size-fraction into a 0.6 ml microfuge tube that has been pierced at the bottom with a 21 G needle. This pierced tube is placed inside a 1.7 ml microfuge tube, and centrifuged at 16110 g, 4° C. for 5 min. The gel pieces are thus conveniently shredded and collected in the bottom of each 1.7 ml tube. Add 200 μl of LoTE: NH4OAc (167:33) (LoTE according to the recipe below, NH4OAc from Ambion) to each tube and elute by heating at 65° C. for 2 hrs.
LoTE Buffer:
3 mM Tris-HCl pH 7.5 (Ambion)
0.2 mM EDTA (Ambion)
Separate the supernatant (containing the eluted concatenated DNA) away from the gel pieces with the aid of microspin filter units as before, by spinning at 16110 g, 10 min, 4° C. Perform phenol/chloroform extraction on each eluted size-fraction, then ethanol precipitate:

| | |
|---|---|
| Eluted DNA fraction | 200 ul |
| 3 M Sodium Acetate pH 5.2 | 20 ul |
| GlycoBlue | 2.2 ul |
| 100% Ethanol | 800 ul |

Keep at −80° C., 30 min, then spin 16110 g, 4° C., 30 min; wash 1× with 75% Ethanol. Resuspend the pellet in 6 ul of LoTE buffer.

(e) Ligation to pZErO-1 Vector

Prior to use, the pZErO-1 cloning vector is prepared by digesting 2 ug of pZErO-1 plasmid DNA (Invitrogen) with 10 units of BamHI (New England Biolabs) for 2 hours at 37° C. The digested plasmid DNA is phenol chloroform extracted and ethanol precipitated, then resuspended in 60 ul of LoTE at a concentration of 33 ng/µl. The plasmid may be validated by setting up a vector self-ligation as a control (there should be few colonies), as well as by running on an agarose gel.

Set up the ligation as follows:

| | |
|---|---|
| Concatemer DNA fraction | 6 ul |
| BamHI/pZErO-1 | 1 ul |
| 5× ligase buffer (with PEG) (Invitrogen) | 2 ul |
| T4 DNA ligase (5 U/uL) (Invitrogen) | 1 ul |

Incubate at 16° C. overnight. Do not heat inactivate.

Also set up self-ligation of the vector in parallel as a control. When preparing the vector for self-ligation, replace the concatemer DNA fraction with nuclease free water.

Purify each ligation reaction to remove salts before electroporation: adjust volume to 200 ul with nuclease free water, perform phenol/chloroform extraction (pH 7.9) and ethanol precipitate (with GlycoBlue) at −80° C. for 30 min. Spin, wash the pellet at least twice with 70% ethanol, and resuspend in 12 ul LoTE.

Add 1 ul of the purified ligation reaction into 25 ul electrocompetent cells (e.g. E. cloni from Lucigen; Top10 from Invitrogen), in pre-chilled 1.7 ml microfuge tubes. Do NOT pipette up and down to mix; instead, gently stir with the pipette tip. Stand on ice for 5 min, then transfer to pre-chilled Biorad electroporation cuvettes (0.1 cm gap).

Stand on ice for another 5 min. Electroporate using Biorad Micropulser unit, single pulse, program EC1. The time constant is usually between 4.5 to 5 ms.

Add 1 ml room temperature plain LB media within 10 sec of pulsing; transfer to 15 ml Falcon tube, and recover at 37° C., 1 hr, 200 rpm shaking.

Plate between 20-50 ul (out of 1 ml) on a small agar plate containing Low Salt LB agar plus Zeocin (Immedia Zeocin Agar, Invitrogen) and incubate overnight at 37° C.

(f) Library Quality Control

Count the numbers of colonies and determine library efficiency after eliminating the self-ligation background. Pick 24-48 colonies for PCR screening using primers PMR011 and PMR012. Include a control PCR on the pZErO-1 vector itself.

Based on the PCR results, pick 1 to 4×96-well plates of colonies for overnight culture (in Low Salt LB+Zeocin, Immedia, Invitrogen), plasmid purification and sequencing to determine the average number of ditags per insert.

At this stage, the library can be stored in the form of purified ligation mix at −20° C., until one wishes to perform large scale transformations, plasmid extractions and sequencing.

(g) Sequencing Library Plating and Colony Picking

The transformed TOP10 (Invitrogen) bacteria cells were plated out on 22×22 cm agar plates (Q-trays, Genetix) with colony density of less than 2,000 per plate to facilitate robotic picking. Individual colonies were picked and cultured in 384-well plates with LB plus Zeocin (see above) at 37° C. overnight. Multiple copies of 384-well plates are replicated and stored in −80° C. in the presence of 15% glycerol (Sigma).

(h) Template Preparation

Plasmid DNA from the pZERO-1-derived clones is prepared using the Sprintprep solid-phase kit (Agencourt).

(i) DNA Sequencing

Plasmids are sequenced using the sequencing primers PMR011 and PMR012 (SEQ ID NOS: 13 and 14 respectively) to sequence in both directions.

(5) Map the CIA-diPETs

Mapping may be performed using the Compressed Suffix Array. Multiple joins across two different DNA fragments (n>3) shall be taken to represent real distal control regions (FIG. 5). More than 3 PETs have to show rearrangement of the same stretch of DNA—that is, tag 1 and tag 2 separated by a distance of more than 10 kB or located on different chromosomes, before any chimera consisting of tags that map to different locations of the genome, is taken to be representative of genomic rearrangements.

Example 4

Preparation of M and G Vector pGIS8 for Use (a) Obtain pGIS8 vector.
(b) Amplify by Rolling Circle Amplification as before (Templiphi kit, Amersham)

Thaw solutions on ice. Prepare 3-4 tubes of the following:

| | |
|---|---|
| 1 ng of DNA (from Maxiprep) | 1 ul |
| Templiphi kit denature buffer | 10 ul |

Heat at 95° C. for 3 minutes, then briefly cool on ice.
To the reaction buffer, add:

| | |
|---|---|
| Templiphi kit premix | 10 ul |

Mix well by tapping or gentle vortexing.
Incubate at 30° C., no shaking, 16-18 hours.
Examine the material. It should be viscous. Quantitate DNA by picogreen fluorimetry (Quant-It kit, Molecular Probes).

(c) Perform restriction enzyme digest

| | |
|---|---|
| DNA | 25 ul |
| XhoI (20 U/ul) (New England Biolabs) | 1 ul |
| EcoR1 (20 U/ul) (New England Biolabs) | 1 ul |
| 10× Buffer EcoR1 (New England Biolabs) | 5 ul |
| 100× BSA (New England Biolabs) | 1 ul |
| Nuclease Free Water | 17 ul |

Incubate at 37° C. for 16 hours.
Purify with PCR purification kit (Qiagen).
Test 5 ul on a 1% agarose gel.

(d) End-it Blunt

Prepare two tubes of:

| | |
|---|---|
| DNA | 22.5 ul |
| 10× End Repair Buffer (Epicentre) | 5 ul |
| 2.5 mM dNTP Mix (Epicentre) | 5 ul |

| | |
|---|---|
| 10 mM ATP (Epicentre) | 5 ul |
| End-Repair Enzyme Mix | 1 ul |
| Nuclease Free Water | 11.5 ul |

Incubate at room temperature for 45 minutes, stop by heating at 70° C. for 10 minutes.

It will be appreciated that various modifications and improvements may be made by a person skilled in the art without departing from the spirit and scope of the present invention.

For example, the CIA method of the present invention may be used in other kinds of cells such as yeast cells instead of mammalian cells. Also, instead of using ChIP, the method may be performed by cross-linking with a suitable fixative without need for immunoprecipitation. In this variation, the protocol is:
1. Harvest cells.
2. Cross-link with formaldehyde for 10 min at 36° C.
3. Cell lysis with bead-beater followed by centrifugation to obtain a supernatant.
4. Shear DNA by sonication, hydroshearing, repeated drawing through a hypodermic syringe needle or restriction enzyme digestion.
5. Remove unwanted proteins with SDS and Triton-X treatment.

Thereafter, the DNA may be further processed (end blunting, ligation) as described above.

Further, in another variation, rolling circle amplification may be used instead of PCR. In such a variation, the protocol following removal of unwanted proteins is:
1. End-blunting of DNA.
2. A-tailing of DNA.
3. Ligation.
4. Rolling circle amplification; may be performed with a suitable commercial kit such as the Templiphi kit from Amersham Biosciences.
5. Quantification of DNA; may be performed with the Invitrogen/Molecular Probes' PicoGreen fluorimetry kit.
6. Digestion with MmeI restriction enzyme to obtain the isolated oligonucleotides.

Further, in another variation, the A-tailing step may be omitted and a suitable blunt-ended adaptor may be used.

REFERENCES

Antequera and Bird (1993), Proc Natl Acad Sci USA. 90(24): 11995-9
Ausubel (1995) Current Protocols in Molecular Biology, Vol. 2, 1995, Ed. Ausubel, et al., Greene Publish. Assoc. & Wiley Interscience, Unit 3.1.15
Bonetta (2006) Nature Methods 3(2): 141-147.
Brenner et al (2000)., Nat Biotechnol, 2000. 18(6): p. 630-4
Buck and Lieb (2004) Genomics 83(3):349-60
Dekker J, Rippe K, Dekker M and Kleckner N (2002) Science 295 (5558):1306-11.
Dunn et al (2002) Genome Research 12(11): 1756-1765
Euskirchen et al., Mol Cell Biol, 2004. 24(9): p. 3804-14
Li and Chandrasegaran (1993) Proc. Nat. Acad. Sciences USA 90:2764-8
Lieb et al., Nat Genet, 2001. 28(4): p. 327-34
Margulies et al, 2005 Nature 437, 376-380 (15 Sep. 2005)
New England Biolabs Catalog 2005. New England Biolabs (Ipswich, Mass.)
Szybalski, W., 1985, Gene, 40:169
Taverner et al., Genome Biol, 2004. 5(3):210.
US 20050255501
US 20050059022
US 20030068629
U.S. Pat. No. 4,766,072
Weinmann et al., Genes Dev, 2002.16(2):235-44)

The invention claimed is:

1. An isolated oligonucleotide comprising at least one first tag and at least one second tag, and at least one linker inserted between the first and second tags, wherein the first and second tags comprise an identifiable sequence of 8-20 base pairs, wherein the first tag comprises at least one most terminal nucleotide sequence from a first polynucleotide and the second tag comprises at least one most terminal nucleotide sequence from a second polynucleotide, wherein the first and second polynucleotides each are capable of binding with at least one protein of a nucleic acid-protein complex, wherein the nucleic acid-protein complex is part of a chromatin structure or is obtained through chromatin immunoprecipitation or both, and wherein the first and second polynucleotides comprise distal interacting regions from the same or different chromosomes.

2. The isolated oligonucleotide according to claim 1, wherein the oligonucleotide further comprises at least one restriction enzyme recognition site.

3. The isolated oligonucleotide according to claim 2, wherein the linker comprises the at least one restriction enzyme recognition site.

4. The isolated oligonucleotide according to claim 3, wherein the at least one restriction enzyme recognition site is for a type IIs restriction enzyme.

5. The isolated oligonucleotide according to claim 3, wherein the at least one restriction enzyme recognition site is for a homing restriction enzyme.

6. The isolated oligonucleotide according to claim 1, wherein the at least one first tag comprises a 5' most terminal nucleotide sequence and a 3' most terminal nucleotide sequence of the first polynucleotide and the at least one second tag comprises a 5' most terminal nucleotide sequence and a 3' most terminal nucleotide sequence of the second polynucleotide.

7. The isolated oligonucleotide according to claim 3, wherein the linker comprises a first restriction recognition site recognized by a restriction enzyme capable of cleaving a first polynucleotide to obtain the first tag, and a second restriction recognition site recognized by a restriction enzyme capable of cleaving a second polynucleotide to obtain the second tag.

8. The isolated oligonucleotide according to claim 3, wherein the linker comprises a first restriction recognition site recognized by a first restriction enzyme capable of cleaving a first polynucleotide to obtain a 3' most terminal nucleotide sequence of the first polynucleotide, and a second restriction recognition site recognized by a second restriction enzyme capable of cleaving a second polynucleotide to obtain a 5' most terminal nucleotide sequence of the second polynucleotide.

9. The isolated oligonucleotide according to claim 3, wherein the linker comprises a first restriction recognition site recognized by a first restriction enzyme capable of cleaving a first polynucleotide to obtain a 5' most terminal nucleotide sequence of the first polynucleotide, and a second restriction recognition site recognized by a second restriction enzyme capable of cleaving a second polynucleotide to obtain a 3' most terminal sequence of the second polynucleotide.

10. The isolated oligonucleotide according to claim 3, wherein the linker comprises a first restriction recognition site recognized by a first restriction enzyme capable of cleaving a first polynucleotide to obtain a 3' most terminal nucleotide sequence of the first polynucleotide, and a second restriction recognition site recognized by a second restriction enzyme capable of cleaving a second polynucleotide to obtain a 5' most terminal nucleotide sequence of the second polynucleotide, the first polynucleotide further comprises a third recognition site recognized by a third restriction enzyme capable of cleaving the first polynucleotide to obtain a 5' most terminal nucleotide sequence of the first polynucleotide, and the second polynucleotide comprises a fourth recognition site recognized by a fourth restriction enzyme capable of cleaving the second polynucleotide to obtain a 3' terminus most terminal nucleotide sequence of the second polynucleotide; the first and second polynucleotides being polynucleotides of a nucleic acid-protein complex; the at least one first tag obtained from ligating the 5' and 3' most terminal nucleotide sequences of the first polynucleotide and the at least one second tag obtained from ligating the 5' and 3' most terminal nucleotide sequences of the second polynucleotide.

11. A vector comprising the oligonucleotide of claim 1.

12. A concatemer of oligonucleotides comprising at least two isolated oligonucleotides, each isolated oligonucleotide comprising at least one first tag and at least one second tag, and at least one linker inserted between the first and second tags, wherein the first and second tags comprise an identifiable sequence of 8-20 base pairs, wherein the first tag comprises at least one most terminal nucleotide sequence from a first polynucleotide and the second tag comprises at least one most terminal nucleotide sequence from a second polynucleotide, and wherein the first and the second polynucleotides each are capable of binding with at least one protein of a nucleic acid-protein complex which is part of a chromatin structure or obtained through chromatin immunoprecipitation or both, and wherein the first and second polynucleotides comprise distal interacting regions from the same or different chromosomes.

13. The concatemer of oligonucleotides according to claim 12, wherein each isolated oligonucleotide comprises at least one restriction enzyme recognition site.

14. The concatemer of oligonucleotides according to claim 13, wherein for each oligonucleotide, the at least one recognition site is included in the linker.

15. The concatemer of oligonucleotides according to claim 13, wherein for each oligonucleotide, the at least one restriction enzyme recognition site is for a type IIs restriction enzyme.

16. The concatemer of oligonucleotides according to claim 12, wherein for each oligonucleotide the first tag comprises a 5' most terminal nucleotide sequence and a 3' most terminal nucleotide sequence from the first polynucleotide and the second tag further comprises a 5' most terminal nucleotide sequence and a 3' most terminal nucleotide sequence from the second polynucleotide.

17. An oligonucleotide library comprising at least one oligonucleotide according to claim 1.

18. A method of detecting and/or identifying at least two polynucleotides of a nucleic acid-protein complex, the method comprising:
 (a) providing the isolated oligonucleotide of claim 1;
 (b) sequencing the oligonucleotide; and
 (c) mapping the at least two polynucleotides based on the nucleotide sequences of the first and second tags, thereby detecting and/or identifying the at least two polynucleotides.

19. The method according to claim 18, wherein the nucleic acid-protein complex is obtained by chromatin immunoprecipitation.

20. The method according to claim 18, wherein the oligonucleotide is concatenated with at least one further oligonucleotide of step (a) before being sequenced.

21. The method according to claim 18, wherein the polynucleotides are located on the same chromosome or the polynucleotides are located on different chromosomes.

22. The isolated oligonucleotide of claim 1, wherein the first and second tags comprise an identifiable sequence of 8-16 base pairs.

23. The isolated oligonucleotide of claim 1, wherein the first and second tags comprise an identifiable sequence of 16-20 base pairs.

24. The concatemer of oligonucleotides of claim 12, wherein the first and second tags comprise an identifiable sequence of 8-16 base pairs.

25. The concatemer of oligonucleotides of claim 12, wherein the first and second tags comprise an identifiable sequence of 16-20 base pairs.

* * * * *

SEQUENCE LISTING

<160> NUMBER OF SEQ ID NOS: 63

<210> SEQ ID NO 1
<211> LENGTH: 31
<212> TYPE: DNA
<213> ORGANISM: Artificial
<220> FEATURE:
<223> OTHER INFORMATION: M&M linker sense strand; 5' end is
      phosphorylated

<400> SEQUENCE: 1
gtcggaggcc aaggcggccg tacgtccaac t                                    31

<210> SEQ ID NO 2
<211> LENGTH: 31
<212> TYPE: DNA
<213> ORGANISM: Artificial
<220> FEATURE:
<223> OTHER INFORMATION: M&M linker antisense strand; 5' end is
      phosphorylated

<400> SEQUENCE: 2
gttggacgta cggccgcctt ggcctccgac t                                    31

<210> SEQ ID NO 3
<211> LENGTH: 31
<212> TYPE: DNA

```
<213> ORGANISM: Artificial
<220> FEATURE:
<223> OTHER INFORMATION: M&G linker sense strand; 5' end is
      phosphorylated

<400> SEQUENCE: 3
gtcggaggcc aaggcggccg tacgctggag t                              31

<210> SEQ ID NO 4
<211> LENGTH: 31
<212> TYPE: DNA
<213> ORGANISM: Artificial
<220> FEATURE:
<223> OTHER INFORMATION: M&G linker antisense strand; 5' end is
      phosphorylated

<400> SEQUENCE: 4
ctccagcgta cggccgcctt ggcctccgac t                              31

<210> SEQ ID NO 5
<211> LENGTH: 28
<212> TYPE: DNA
<213> ORGANISM: Artificial
<220> FEATURE:
<223> OTHER INFORMATION: P1 concatenating adaptor (PMR 011) sense
      strand; 5' end is phosphorylated

<400> SEQUENCE: 5 ggatcccctta atcgccttgc agcacatc                                 28

<210> SEQ ID NO 6
<211> LENGTH: 30
<212> TYPE: DNA
<213> ORGANISM: Artificial
<220> FEATURE:
<223> OTHER INFORMATION: P1 concatenating adaptor (PMR 011) antisense
      strand; 5' end is not phosphorylated
<220> FEATURE:
<221> NAME/KEY: misc_feature
<222> LOCATION: (29)..(30)
<223> OTHER INFORMATION: n is a, c, g, or t

<400> SEQUENCE: 6
gatgtgctgc aaggcgatta agggatccnn                                30

<210> SEQ ID NO 7
<211> LENGTH: 29
<212> TYPE: DNA
<213> ORGANISM: Artificial
<220> FEATURE:
<223> OTHER INFORMATION: P2 concatenating adaptor (PMR 012) sense
      strand; 5' end is phosphorylated.

<400> SEQUENCE: 7
ggatcccctg tgtgaaattg ttatccgct                                 29

<210> SEQ ID NO 8
<211> LENGTH: 31
<212> TYPE: DNA
<213> ORGANISM: Artificial
<220> FEATURE:
<223> OTHER INFORMATION: P2 concatenating adaptor (PMR 012) antisense
      strand; 5' end not phosphorylated.
<220> FEATURE:
<221> NAME/KEY: misc_feature
<222> LOCATION: (30)..(31)
<223> OTHER INFORMATION: n is a, c, g, or t

<400> SEQUENCE: 8
```

```
agcggataac aatttcacac aggggatccn n                              31
```

<210> SEQ ID NO 9
<211> LENGTH: 28
<212> TYPE: DNA
<213> ORGANISM: Artificial
<220> FEATURE:
<223> OTHER INFORMATION: D1 diPETing adaptor (PMR011) sense strand; 5'
      end phosphorylated

<400> SEQUENCE: 9

```
ggatcccttat atcgccttgc agcacatc                                 28
```

<210> SEQ ID NO 10
<211> LENGTH: 30
<212> TYPE: DNA
<213> ORGANISM: Artificial
<220> FEATURE:
<223> OTHER INFORMATION: D1 diPETing adaptor (PMR011) antisense strand;
      5' end not phosphorylated.
<220> FEATURE:
<221> NAME/KEY: misc_feature
<222> LOCATION: (29)..(30)
<223> OTHER INFORMATION: n is a, c, g, or t

<400> SEQUENCE: 10

```
gatgtgctgc aaggcgatta agggatccnn                                30
```

<210> SEQ ID NO 11
<211> LENGTH: 39
<212> TYPE: DNA
<213> ORGANISM: Artificial
<220> FEATURE:
<223> OTHER INFORMATION: D2 diPETing adaptor (PMR012) sense strand; 5'
      end phosphorylated.

<400> SEQUENCE: 11

```
ggatccaatg ctcctccctg tgtgaaattg ttatccgct                      39
```

<210> SEQ ID NO 12
<211> LENGTH: 41
<212> TYPE: DNA
<213> ORGANISM: Artificial
<220> FEATURE:
<223> OTHER INFORMATION: D2 diPETing adaptor (PMR012) antisense strand;
      5' end not phosphorylated.
<220> FEATURE:
<221> NAME/KEY: misc_feature
<222> LOCATION: (40)..(41)
<223> OTHER INFORMATION: n is a, c, g, or t

<400> SEQUENCE: 12

```
agcggataac aatttcacac agggaggagc attggatccn n                   41
```

<210> SEQ ID NO 13
<211> LENGTH: 22
<212> TYPE: DNA
<213> ORGANISM: Artificial
<220> FEATURE:
<223> OTHER INFORMATION: PMR011; 5' end phosphorylated.

<400> SEQUENCE: 13

```
gatgtgctgc aaggcgatta ag                                        22
```

<210> SEQ ID NO 14
<211> LENGTH: 23
<212> TYPE: DNA
<213> ORGANISM: Artificial
<220> FEATURE:

<223> OTHER INFORMATION: PMR012; 5' end is phosphorylated

<400> SEQUENCE: 14
agcggataac aatttcacac agg    23

<210> SEQ ID NO 15
<211> LENGTH: 32
<212> TYPE: DNA
<213> ORGANISM: Artificial
<220> FEATURE:
<223> OTHER INFORMATION: RecA selection oligonucleotide; biotinylated.

<400> SEQUENCE: 15
agtcggaggc caaggcggcc gtacgctgga gt    32

<210> SEQ ID NO 16
<211> LENGTH: 43
<212> TYPE: DNA
<213> ORGANISM: Artificial
<220> FEATURE:
<223> OTHER INFORMATION: Sense strand of multiple cloning site stuffer for pGIS8 vector.

<400> SEQUENCE: 16
aattggatcc gactcgagga tgaattctcc aggatccctc ctc    43

<210> SEQ ID NO 17
<211> LENGTH: 43
<212> TYPE: DNA
<213> ORGANISM: Artificial
<220> FEATURE:
<223> OTHER INFORMATION: Antisense strand of multiple cloning site stuffer for pGIS8 vector.

<400> SEQUENCE: 17
tcgagaggag ggatcctgga gaattcatcc tcgagtcgga tcc    43

<210> SEQ ID NO 18
<211> LENGTH: 3541
<212> TYPE: DNA
<213> ORGANISM: Artificial
<220> FEATURE:
<223> OTHER INFORMATION: Sense strand of pGIS8 vector.

<400> SEQUENCE: 18
gggcgaattc gatatcgcgg ccgcgcctgg ataaagtcag cagcttccac gccagcttca    60
cacaaaaagt gactgacggt agcggcgcgg cggtgcagga aggtcagggc gatctgtggg    120
tgaaacgtcc aaacttattc aactggcata tgacacaacc tgatgaaagc attctggttt    180
ctgacggtaa aacactgtgg ttctataacc gttcgttga gcaagctacg gcaacctggc    240
tgaaagatgc caccggtaat acgccgttta tgctgattgc ccgcaaccag tccagcgact    300
ggcagcagta caatatcaaa cagaatggcg atgactttgt cctgacgccg aaagccagca    360
atggcaatct gaagcagttc accattaacg tgggacgtga tggcacaatc catcagttta    420
gcgcggtgga gcaggacgat cagcgcagca gttatcaact gaaatcccag caaaatgggg    480
ctgtggatgc agcgaaattt accttcaccc cgccgcaagg cgtcacggta gatgatcaac    540
gtaagtagag gcacctgagt gagcaatctg tcgctcgatt tttcggataa tacttttcaa    600
cctctggccg cgcgtatgcg gccagaaaat ttagcacagt atatcggcca gcaacatttg    660
ctggctgcgg ggaagccgtt gccgcgcgct atcgaagccg gcatttacta ttctatgatc    720
ctctgggggc cgccgggtac cggcaaaaca actctcgctg aagtgattgc ccgctatgcg    780

```
aacgctgatg tggaacgtat ttctgccgta agtcgaattg gatccgactc gaggatgaat    840
tctccaggat ccctcctctg agtattctat agtgtcacct aaatagcttg gcgtaatcat    900
ggtcatagct gtttcctgtg tgaaattgtt atccgctcac aattccacac aacatacgag    960
ccggaagcat aaagtgtaaa gcctggggtg cctaatgagt gagctaactc acattaattg    1020
cgttgcgctc actgcccgct ttccagtcgg gaaacctgtc gtgccagctg cattaatgaa    1080
tcggccaacg cgcggggaga ggcggtttgc gtattgggcg ctcttccgct tcctcgctca    1140
ctgactcgct gcgctcggtc gttcggctgc ggcgagcggt atcagctcac tcaaaggcgg    1200
taatacggtt atccacagaa tcaggggata acgcaggaaa gaacatgtga gcaaaaggcc    1260
agcaaaaggc caggaaccgt aaaaaggccg cgttgctggc gtttttcgat aggctccgcc    1320
cccctgacga gcatcacaaa aatcgacgct caagtcagag gtggcgaaac ccgacaggac    1380
tataaagata ccaggcgttt ccccctggaa gctccctcgt gcgctctcct gtaccgaccc    1440
tgccgcttac cggatacctg tccgcctttc tcccttcggg aagcgtggcg ctttctcata    1500
gctcacgctg taggtatctc agttcggtgt aggtcgttcg ctccaagctg gctgtgtgc    1560 acgaaccccc cgttcagccc gaccgctgcg ccttatccgg taactatcgt cttgagacca    1620
acccggtaag acacgactta tcgccactgg cagcagccac tggtaacagg attagcagag    1680
cgaggtatgt aggcggtgct acagagttct tgaagtggtg gcctaactac ggctacacta    1740
gaaggacagt atttggtatc tgcgctctgc tgaagccagt taccttcgga aaaagagttg    1800
gtagctcttg atccggcaaa caaaccaccg ctggtagcgg tggttttttt gtttgcaagc    1860
agcagattac gcgcagaaaa aaaggatctc aagaagatcc tttgatcttt tctacggggt    1920
ctgacgctca gtggaacgaa aactcacgtt aagggatttt ggtcatgaga ttatcaaaaa    1980
ggatcttcac ctagatcctt ttaaattaaa aatgaagttt aaatcaatc taaagtatat    2040 atgagtaaac ttggtctgac agttaccaat gcttaatcag tgaggcacct atctcagcga    2100
tctgtctatt tcgttcatcc atagttgcct gactccccgt cgtgtagata actacgatac    2160
gggagggctt accatctggc cccagtgctg caatgatacc gcgagaccca cgctcaccgg    2220
ctccggattt atcagcaata aaccagccag ccggaagggc cgagcgcaga agtggtcctg    2280
caactttatc cgcctccatc cagtctatta attgttgccg ggaagctaga gtaagtagtt    2340
cgccagttaa tagtttgcgc aacgttgttg gcattgctac aggcatcgtg gtgtcacgct    2400
cgtcgtttgg tatggcttca ttcagctccg gttcccaacg atcaaggcga gttacatgat    2460
cccccatgtt gtgcaaaaaa gcggttagct ccttcggtcc tccgatcgtt gtcagaagta    2520
agttggccgc agtgttatca ctcatggtta tggcagcact gcataattct cttactgtca    2580
tgccatccgt aagatgcttt tctgtgactg gtgagtactc aaccaagtca ttctgagaat    2640
agtgtatgcg gcgaccgagt tgctcttgcc cggcgtcaat acgggataat accgcgccac    2700
atagcagaac tttaaaagtg ctcatcattg gaaaacgttc ttcggggcga aaactctcaa    2760
ggatcttacc gctgttgaga tccagttcga tgtaacccac tcgtgcaccc aactgatctt    2820
cagcatcttt tactttcacc agcgtttctg ggtgagcaaa aacaggaagg caaaatgccg    2880
caaaaaaggg aataagggcg acacggaaat gttgaatact catactcttc cttttttcaat   2940 attattgaag catttatcag ggttattgtc tcatgagcgg atacatattt gaatgtattt    3000
agaaaaataa acaaataggg gttccgcgca catttccccg aaaagtgcca cctgacgtct    3060
aagaaaccat tattatcatg acattaacct ataaaaatag gcgtatcacg aggccctttc    3120
gtctcgcgcg tttcggtgat gacggtgaaa acctctgaca catgcagctc ccggagacgg    3180
```

-continued

| tcacagcttg tctgtaagcg gatgccggga gcagacaagc ccgtcagggc gcgtcagcgg | 3240 |
| gtgttggcgg gtgtcgggc tggcttaact atgcggcatc agagcagatt gtactgagag | 3300 |
| tgcaccatat gcggtgtgaa ataccgcaca gatgcgtaag gagaaaatac cgcatcaggc | 3360 |
| gccattcgcc attcaggctg cgcaactgtt gggaagggcg atcggtgcgg gcctcttcgc | 3420 |
| tattacgcca gctggcgaaa gggggatgtg ctgcaaggcg attaagttgg gtaacgccag | 3480 |
| ggttttccca gtcacgacgt tgtaaaacga cggccagtga attgtaatac gactcactat | 3540 |
| a | 3541 |

<210> SEQ ID NO 19
<211> LENGTH: 3541
<212> TYPE: DNA
<213> ORGANISM: Artificial
<220> FEATURE:
<223> OTHER INFORMATION: Antisense strand of pGIS8 vector.

<400> SEQUENCE: 19

| tatagtgagt cgtattacaa ttcactggcc gtcgttttac aacgtcgtga ctgggaaaac | 60 |
| cctggcgtta cccaacttaa tcgccttgca gcacatcccc ctttcgccag ctggcgtaat | 120 |
| agcgaagagg cccgcaccga tcgcccttcc caacagttgc gcagcctgaa tggcgaatgg | 180 |
| cgcctgatgc ggtattttct ccttacgcat ctgtgcggta tttcacaccg catatggtgc | 240 |
| actctcagta caatctgctc tgatgccgca tagttaagcc agccccgaca cccgccaaca | 300 |
| cccgctgacg cgccctgacg ggcttgtctg ctcccggcat ccgcttacag acaagctgtg | 360 |
| accgtctccg ggagctgcat gtgtcagagg ttttcaccgt catcaccgaa acgcgcgaga | 420 |
| cgaaagggcc tcgtgatacg cctattttta taggttaatg tcatgataat aatggtttct | 480 |
| tagacgtcag gtggcacttt tcggggaaat gtgcgcggaa cccctatttg tttatttttc | 540 |
| taaatacatt caaatatgta tccgctcatg agacaataac cctgataaat gcttcaataa | 600 |
| tattgaaaaa ggaagagtat gagtattcaa catttccgtg tcgcccttat tcccttttt | 660 |
| gcggcatttt gccttcctgt ttttgctcac ccagaaacgc tggtgaaagt aaaagatgct | 720 |
| gaagatcagt tgggtgcacg agtgggttac atcgaactgg atctcaacag cggtaagatc | 780 |
| cttgagagtt ttcgccccga agaacgtttt ccaatgatga gcacttttaa agttctgcta | 840 |
| tgtggcgcgg tattatcccg tattgacgcc gggcaagagc aactcggtcg ccgcatacac | 900 |
| tattctcaga atgacttggt tgagtactca ccagtcacag aaaagcatct tacggatggc | 960 |
| atgacagtaa gagaattatg cagtgctgcc ataaccatga gtgataacac tgcggccaac | 1020 |
| ttacttctga caacgatcgg aggaccgaag gagctaaccg cttttttgca acatgggg | 1080 |
| gatcatgtaa ctcgccttga tcgttgggaa ccggagctga tgaagccat accaaacgac | 1140 |
| gagcgtgaca ccacgatgcc tgtagcaatg ccaacaacgt tgcgcaaact attaactggc | 1200 |
| gaactactta ctctagcttc ccggcaacaa ttaatagact ggatggaggc ggataaagtt | 1260 |
| gcaggaccac ttctgcgctc ggcccttccg gctggctggt ttattgctga taaatccgga | 1320 |
| gccggtgagc gtgggtctcg cggtatcatt gcagcactgg ggccagatgg taagccctcc | 1380 |
| cgtatcgtag ttatctacac gacggggagt caggcaacta tggatgaacg aaatagacag | 1440 |
| atcgctgaga taggtgcctc actgattaag cattggtaac tgtcagacca agtttactca | 1500 |
| tatatacttt agattgattt aaaacttcat ttttaattta aaaggatcta ggtgaagatc | 1560 |
| ctttttgata atctcatgac caaaatccct taacgtgagt tttcgttcca ctgagcgtca | 1620 |
| gaccccgtag aaaagatcaa aggatcttct tgagatcctt ttttctgcg cgtaatctgc | 1680 |

```
tgcttgcaaa caaaaaaacc accgctacca gcggtggttt gtttgccgga tcaagagcta    1740
ccaactcttt ttccgaaggt aactggcttc agcagagcgc agataccaaa tactgtcctt    1800
ctagtgtagc cgtagttagg ccaccacttc aagaactctg tagcaccgcc tacatacctc    1860
gctctgctaa tcctgttacc agtggctgct gccagtggcg ataagtcgtg tcttaccggg    1920
ttggtctcaa gacgatagtt accggataag gcgcagcggt cgggctgaac ggggggttcg    1980
tgcacacagc ccagcttgga gcgaacgacc tacaccgaac tgagatacct acagcgtgag    2040
ctatgagaaa gcgccacgct tcccgaaggg agaaaggcgg acaggtatcc ggtaagcggc    2100
agggtcggta caggagagcg cacgagggag cttccagggg gaaacgcctg gtatctttat    2160
agtcctgtcg ggtttcgcca cctctgactt gagcgtcgat ttttgtgatg ctcgtcaggg    2220
gggcggagcc tatcgaaaaa cgccagcaac gcggcctttt tacggttcct ggccttttgc    2280
tggccttttg ctcacatgtt ctttcctgcg ttatccctg attctgtgga taaccgtatt     2340
accgcctttg agtgagctga taccgctcgc cgcagccgaa cgaccgagcg cagcgagtca    2400
gtgagcgagg aagcggaaga gcgcccaata cgcaaaccgc ctctccccgc gcgttggccg    2460
attcattaat gcagctggca cgacaggttt cccgactgga agcgggcag tgagcgcaac     2520
gcaattaatg tgagttagct cactcattag gcaccccagg ctttacactt tatgcttccg    2580
gctcgtatgt tgtgtggaat tgtgagcgga taacaatttc acacaggaaa cagctatgac    2640
catgattacg ccaagctatt taggtgacac tatagaatac tcagaggagg atcctggag    2700
aattcatcct cgagtcggat ccaattcgac ttacggcaga atacgttcc acatcagcgt     2760
tcgcatagcg ggcaatcact tcagcgagag ttgttttgcc ggtacccggc ggcccccaga    2820
ggatcataga atgtaaatgc ccggcttcga tagcgcgcgg caacggcttc cccgcagcca    2880
gcaaatgttg ctggccgata tactgtgcta aattttctgg ccgcatacgc gcggccagag    2940
gttgaaaagt attatccgaa aaatcgagcg acagattgct cactcaggtg cctctactta    3000
cgttgatcat ctaccgtgac gccttgcggc ggggtgaagg taaatttcgc tgcatccaca    3060
gccccatttt gctgggattt cagttgataa ctgctgcgct gatcgtcctg ctccaccgcg    3120
ctaaactgat ggattgtgcc atcacgtccc acgttaatgg tgaactgctt cagattgcca    3180
ttgctggctt tcggcgtcag gacaaagtca tcgccattct gtttgatatt gtactgctgc    3240
cagtcgctgg actggttgcg ggcaatcagc ataaacggcg tattaccggt ggcatctttc    3300
agccaggttg ccgtagcttg ctcaacgaac gggttataga accacagtgt tttaccgtca    3360
gaaaccagaa tgctttcatc aggttgtgtc atatgccagt tgaataagtt tggacgtttc    3420
acccacagat cgccctgacc ttcctgcacc gccgcgccgc taccgtcagt cacttttttgt   3480
gtgaagctgg cgtggaagct gctgacttta tccaggcgcg gccgcgatat cgaattcgcc    3540
c                                                                   3541
```

<210> SEQ ID NO 20
<211> LENGTH: 69
<212> TYPE: DNA
<213> ORGANISM: Artificial
<220> FEATURE:
<223> OTHER INFORMATION: M&M adaptor PET sense strand.
<220> FEATURE:
<221> NAME/KEY: misc_feature
<222> LOCATION: (1)..(17)
<223> OTHER INFORMATION: n is a, c, g, or t
<220> FEATURE:
<221> NAME/KEY: misc_feature
<222> LOCATION: (50)..(69)
<223> OTHER INFORMATION: n is a, c, g, or t

```
<400> SEQUENCE: 20
nnnnnnnnnn nnnnnnnagt cggaggccaa ggcggccgta cgtccaactn nnnnnnnnnn      60 nnnnnnnnn                                                              69

<210> SEQ ID NO 21
<211> LENGTH: 69
<212> TYPE: DNA
<213> ORGANISM: Artificial
<220> FEATURE:
<223> OTHER INFORMATION: M&M adaptor PET antisense strand
<220> FEATURE:
<221> NAME/KEY: misc_feature
<222> LOCATION: (1)..(18)
<223> OTHER INFORMATION: n is a, c, g, or t
<220> FEATURE:
<221> NAME/KEY: misc_feature
<222> LOCATION: (51)..(69)
<223> OTHER INFORMATION: n is a, c, g, or t

<400> SEQUENCE: 21
nnnnnnnnnn nnnnnnnag ttggacgtac ggccgccttg gcctccgact nnnnnnnnnn       60 nnnnnnnnn                                                              69

<210> SEQ ID NO 22
<211> LENGTH: 128
<212> TYPE: DNA
<213> ORGANISM: Artificial
<220> FEATURE:
<223> OTHER INFORMATION: M&M adaptor PET sense strand with adaptor
      sequences
<220> FEATURE:
<221> NAME/KEY: misc_feature
<222> LOCATION: (29)..(47)
<223> OTHER INFORMATION: n is a, c, g, or t
<220> FEATURE:
<221> NAME/KEY: misc_feature
<222> LOCATION: (80)..(99)
<223> OTHER INFORMATION: n is a, c, g, or t

<400> SEQUENCE: 22
gatgtgctgc aaggcgatta agggatccnn nnnnnnnnnn nnnnnnnagt cggaggccaa      60
ggcggccgta cgtccaactn nnnnnnnnnn nnnnnnnnng atcccctgt gtgaaattgt      120 tatccgct                                                             128

<210> SEQ ID NO 23
<211> LENGTH: 128
<212> TYPE: DNA
<213> ORGANISM: Artificial
<220> FEATURE:
<223> OTHER INFORMATION: M&M adaptor PET antisense strand with adaptor
      sequences
<220> FEATURE:
<221> NAME/KEY: misc_feature
<222> LOCATION: (30)..(49)
<223> OTHER INFORMATION: n is a, c, g, or t
<220> FEATURE:
<221> NAME/KEY: misc_feature
<222> LOCATION: (82)..(100)
<223> OTHER INFORMATION: n is a, c, g, or t

<400> SEQUENCE: 23
agcggataac aatttcacac agggatccn nnnnnnnnn nnnnnnnnna gttggacgta       60
cggccgcctt ggcctccgac tnnnnnnnnn nnnnnnnnnn ggatcccctta atcgccttgc    120 agcacatc                                                             128

<210> SEQ ID NO 24
```

```
<211> LENGTH: 77
<212> TYPE: DNA
<213> ORGANISM: Artificial
<220> FEATURE:
<223> OTHER INFORMATION: M&M final PET sense strand after cleavage of
      adaptor sequences
<220> FEATURE:
<221> NAME/KEY: misc_feature
<222> LOCATION: (6)..(24)
<223> OTHER INFORMATION: n is a, c, g, or t
<220> FEATURE:
<221> NAME/KEY: misc_feature
<222> LOCATION: (57)..(76)
<223> OTHER INFORMATION: n is a, c, g, or t

<400> SEQUENCE: 24
gatccnnnnn nnnnnnnnnn nnnnagtcgg aggccaaggc ggccgtacgt ccaactnnnn    60
nnnnnnnnnn nnnnnng                                                  77

<210> SEQ ID NO 25
<211> LENGTH: 77
<212> TYPE: DNA
<213> ORGANISM: Artificial
<220> FEATURE:
<223> OTHER INFORMATION: M&M final PET antisense strand after cleavage
      of of adaptor sequences.
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (58)..(76)
<223> OTHER INFORMATION: n is a, c, g, or t

<400> SEQUENCE: 25
gatccnnnnn nnnnnnnnnn nnnnagttg gacgtacggc cgccttggcc tccgactnnn     60
nnnnnnnnnn nnnnng                                                   77

<210> SEQ ID NO 26
<211> LENGTH: 85
<212> TYPE: DNA
<213> ORGANISM: Artificial
<220> FEATURE:
<223> OTHER INFORMATION: M&G adaptor sense strand after sonication
<220> FEATURE:
<221> NAME/KEY: misc_feature
<222> LOCATION: (1)..(23)
<223> OTHER INFORMATION: n is a, c, g, or t
<220> FEATURE:
<221> NAME/KEY: misc_feature
<222> LOCATION: (56)..(85)
<223> OTHER INFORMATION: n is a, c, g, or t

<400> SEQUENCE: 26
nnnnnnnnnn nnnnnnnnnn nnnagtcgga ggccaaggcg gccgtacgct ggagtnnnn     60 nnnnnnnnnn nnnnnnnnnn nnnnn                                         85

<210> SEQ ID NO 27
<211> LENGTH: 85
<212> TYPE: DNA
<213> ORGANISM: Artificial
<220> FEATURE:
<223> OTHER INFORMATION: M&G adaptor antisense strand after sonication
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (63)..(85)
```

<223> OTHER INFORMATION: n is a, c, g, or t

<400> SEQUENCE: 27
nnnnnnnnnn nnnnnnnnnn nnnnnnnnnn actccagcgt acggccgcct tggcctccga    60
ctnnnnnnnn nnnnnnnnnn nnnnn                                           85

<210> SEQ ID NO 28
<211> LENGTH: 140
<212> TYPE: DNA
<213> ORGANISM: Artificial
<220> FEATURE:
<223> OTHER INFORMATION: M&G adaptor sense strand after cloning into
      pGIS8 vector, rest of vector not shown.
<220> FEATURE:
<221> NAME/KEY: misc_feature
<222> LOCATION: (10)..(54)
<223> OTHER INFORMATION: n is a, c, g, or t
<220> FEATURE:
<221> NAME/KEY: misc_feature
<222> LOCATION: (87)..(129)
<223> OTHER INFORMATION: n is a, c, g, or t

<400> SEQUENCE: 28
ggatccgacn nnnnnnnnn nnnnnnnnnn nnnnnnnnnn nnnnnnnnnn nnnnagtcgg    60
aggccaaggc ggccgtacgc tggagtnnnn nnnnnnnnnn nnnnnnnnnn nnnnnnnnnn   120
nnnnnnnnnc tccaggatcc                                                140

<210> SEQ ID NO 29
<211> LENGTH: 140
<212> TYPE: DNA
<213> ORGANISM: Artificial
<220> FEATURE:
<223> OTHER INFORMATION: M&G adaptor antisense strand after cloning
      into pGIS8 vector, rest of vector not shown.
<220> FEATURE:
<221> NAME/KEY: misc_feature
<222> LOCATION: (12)..(54)
<223> OTHER INFORMATION: n is a, c, g, or t
<220> FEATURE:
<221> NAME/KEY: misc_feature
<222> LOCATION: (87)..(131)
<223> OTHER INFORMATION: n is a, c, g, or t

<400> SEQUENCE: 29
ggatcctgga gnnnnnnnnn nnnnnnnnnn nnnnnnnnnn nnnnnnnnnn nnnnactcca    60
gcgtacggcc gccttggcct ccgactnnnn nnnnnnnnnn nnnnnnnnnn nnnnnnnnnn   120
nnnnnnnnnn ngtcggatcc                                                140

<210> SEQ ID NO 30
<211> LENGTH: 132
<212> TYPE: DNA
<213> ORGANISM: Artificial
<220> FEATURE:
<223> OTHER INFORMATION: M PET intermediate sense strand
<220> FEATURE:
<221> NAME/KEY: misc_feature
<222> LOCATION: (10)..(46)
<223> OTHER INFORMATION: n is a, c, g, or t
<220> FEATURE:
<221> NAME/KEY: misc_feature
<222> LOCATION: (79)..(121)
<223> OTHER INFORMATION: n is a, c, g, or t

<400> SEQUENCE: 30
ggatccgacn nnnnnnnnn nnnnnnnnnn nnnnnnnnnn nnnnnagtc ggaggccaag     60 gcggccgtac gctggagtnn nnnnnnnnnn nnnnnnnnnn nnnnnnnnnn nnnnnnnnn    120 nctccaggat cc 132

<210> SEQ ID NO 31
<211> LENGTH: 132
<212> TYPE: DNA
<213> ORGANISM: Artificial
<220> FEATURE:
<223> OTHER INFORMATION: M PET intermediate antisense strand
<220> FEATURE:
<221> NAME/KEY: misc_feature
<222> LOCATION: (12)..(64)
<223> OTHER INFORMATION: n is a, c, g, or t
<220> FEATURE:
<221> NAME/KEY: misc_feature
<222> LOCATION: (97)..(123)
<223> OTHER INFORMATION: n is a, c, g, or t

<400> SEQUENCE: 31
ggatcctgga gnnnnnnnnn nnnnnnnnnn nnnnnnnnnn nnnnnnnnnn  60
nnnnactcca gcgtacggcc gccttggcct ccgactnnnn nnnnnnnnnn  120
nnngtcggat cc  132

<210> SEQ ID NO 32
<211> LENGTH: 116
<212> TYPE: DNA
<213> ORGANISM: Artificial
<220> FEATURE:
<223> OTHER INFORMATION: M&G diPET sense strand
<220> FEATURE:
<221> NAME/KEY: misc_feature
<222> LOCATION: (9)..(45)
<223> OTHER INFORMATION: n is a, c, g, or t
<220> FEATURE:
<221> NAME/KEY: misc_feature
<222> LOCATION: (78)..(105)
<223> OTHER INFORMATION: n is a, c, g, or t

<400> SEQUENCE: 32
gatccgacnn nnnnnnnnn nnnnnnnnnn nnnnnnnnnn nnnnagtcg gaggccaagg  60 cggccgtacg ctggagtnnn nnnnnnnnn nnnnnnnnnn nnnnctcca ggatcc  116

<210> SEQ ID NO 33
<211> LENGTH: 116
<212> TYPE: DNA
<213> ORGANISM: Artificial
<220> FEATURE:
<223> OTHER INFORMATION: M&G diPET antisense strand
<220> FEATURE:
<221> NAME/KEY: misc_feature
<222> LOCATION: (12)..(37)
<223> OTHER INFORMATION: n is a, c, g, or t
<220> FEATURE:
<221> NAME/KEY: misc_feature
<222> LOCATION: (70)..(108)
<223> OTHER INFORMATION: n is a, c, g, or t

<400> SEQUENCE: 33
ggatcctgga gnnnnnnnnn nnnnnnnnnn nnnnnnnact ccagcgtacg gccgccttgg  60
cctccgactn nnnnnnnnnn nnnnnnnnnn nnnnnnnnnn nnnnnnnngt cggatc  116

<210> SEQ ID NO 34
<211> LENGTH: 111
<212> TYPE: DNA
<213> ORGANISM: Artificial
<220> FEATURE:
<223> OTHER INFORMATION: Released diPET sense strand with BamH1 sticky
      ends
<220> FEATURE:
<221> NAME/KEY: misc_feature

```
<222> LOCATION: (9)..(45)
<223> OTHER INFORMATION: n is a, c, g, or t
<220> FEATURE:
<221> NAME/KEY: misc_feature
<222> LOCATION: (78)..(105)
<223> OTHER INFORMATION: n is a, c, g, or t

<400> SEQUENCE: 34
gatccgacnn nnnnnnnnnn nnnnnnnnnn nnnnnnnnnn nnnnnagtcg gaggccaagg        60
cggccgtacg ctggagtnnn nnnnnnnnnn nnnnnnnnnn nnnnnctcca g                111

<210> SEQ ID NO 35
<211> LENGTH: 111
<212> TYPE: DNA
<213> ORGANISM: Artificial
<220> FEATURE:
<223> OTHER INFORMATION: Released diPET antisense strand with BamH1
      sticky ends
<220> FEATURE:
<221> NAME/KEY: misc_feature
<222> LOCATION: (11)..(39)
<223> OTHER INFORMATION: n is a, c, g, or t
<220> FEATURE:
<221> NAME/KEY: misc_feature
<222> LOCATION: (72)..(107)
<223> OTHER INFORMATION: n is a, c, g, or t

<400> SEQUENCE: 35
gatcctggag nnnnnnnnnn nnnnnnnnnn nnnnnnnnna ctccagcgta cggccgcctt        60
ggcctccgac tnnnnnnnnn nnnnnnnnnn nnnnnnnnnn nnnnnnngtc g                111

<210> SEQ ID NO 36
<211> LENGTH: 91
<212> TYPE: DNA
<213> ORGANISM: Artificial
<220> FEATURE:
<223> OTHER INFORMATION: M&M PET sense strand before MmeI digestion
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (61)..(91)
<223> OTHER INFORMATION: n is a, c, g, or t

<400> SEQUENCE: 36
nnnnnnnnnn nnnnnnnnnn nnnnnnnnag tcggaggcca aggcggccgt acgtccaact        60
nnnnnnnnnn nnnnnnnnnn nnnnnnnnnn n                                      91

<210> SEQ ID NO 37
<211> LENGTH: 91
<212> TYPE: DNA
<213> ORGANISM: Artificial
<220> FEATURE:
<223> OTHER INFORMATION: M&M PET antisense sequence before MmeI
      digestion
<220> FEATURE:
<221> NAME/KEY: misc_feature
<222> LOCATION: (1)..(31)
<223> OTHER INFORMATION: n is a, c, g, or t
<220> FEATURE:
<221> NAME/KEY: misc_feature
<222> LOCATION: (64)..(91)
<223> OTHER INFORMATION: n is a, c, g, or t

<400> SEQUENCE: 37
nnnnnnnnnn nnnnnnnnnn nnnnnnnnnn nagttggacg tacggccgcc ttggcctccg        60
actnnnnnnn nnnnnnnnnn nnnnnnnnnn n                                      91
```

```
<210> SEQ ID NO 38
<211> LENGTH: 53
<212> TYPE: DNA
<213> ORGANISM: Artificial
<220> FEATURE:
<223> OTHER INFORMATION: Oligonucleotide of FIG. 8 sense strand before
      insertion of M&G linker.
<220> FEATURE:
<221> NAME/KEY: misc_feature
<222> LOCATION: (1)..(53)
<223> OTHER INFORMATION: n is a, c, g, or t

<400> SEQUENCE: 38
nnnnnnnnnn nnnnnnnnnn nnnnnnnnnn nnnnnnnnnn nnnnnnnnnn nnn         53

<210> SEQ ID NO 39
<211> LENGTH: 53
<212> TYPE: DNA
<213> ORGANISM: Artificial
<220> FEATURE:
<223> OTHER INFORMATION: Oligonucleotide of FIG. 8 antisense strand
      before insertion of M&G linker
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (32)..(53)
<223> OTHER INFORMATION: n is a, c, g, or t

<400> SEQUENCE: 39
nnnnnnnnnn nnnnnnnnnn nnnnnnnnnn tnnnnnnnnn nnnnnnnnnn nnn         53

<210> SEQ ID NO 40
<211> LENGTH: 140
<212> TYPE: DNA
<213> ORGANISM: Artificial
<220> FEATURE:
<223> OTHER INFORMATION: Oligonucleotide of FIG.8 sense strand inserted
      into plasmid (rest of plasmid not shown)
<220> FEATURE:
<221> NAME/KEY: misc_feature
<222> LOCATION: (10)..(129)
<223> OTHER INFORMATION: n is a, c, g, or t

<400> SEQUENCE: 40
ggatccgacn nnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnc tccaggatcc                                               140

<210> SEQ ID NO 41
<211> LENGTH: 140
<212> TYPE: DNA
<213> ORGANISM: Artificial
<220> FEATURE:
<223> OTHER INFORMATION: Oligonucleotide of FIG.8 antisense strand
      inserted into plasmid (rest of plasmid not shown)
<220> FEATURE:
<221> NAME/KEY: misc_feature
<222> LOCATION: (12)..(131)
<223> OTHER INFORMATION: n is a, c, g, or t

<400> SEQUENCE: 41
ggatcctgga gnnnnnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn ngtcggatcc                                               140
```

```
<210> SEQ ID NO 42
<211> LENGTH: 140
<212> TYPE: DNA
<213> ORGANISM: Artificial
<220> FEATURE:
<223> OTHER INFORMATION: Oligonucleotide of FIG.8 sense strand inserted
      into plasmid (rest of plasmid not shown) after MmeI cut
<220> FEATURE:
<221> NAME/KEY: misc_feature
<222> LOCATION: (10)..(129)
<223> OTHER INFORMATION: n is a, c, g, or t

<400> SEQUENCE: 42
ggatccgacn nnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnc tccaggatcc                                                 140

<210> SEQ ID NO 43
<211> LENGTH: 140
<212> TYPE: DNA
<213> ORGANISM: Artificial
<220> FEATURE:
<223> OTHER INFORMATION: Oligonucleotide of FIG.8 antisense strand
      inserted into plasmid (rest of plasmid not shown) after MmeI cut
<220> FEATURE:
<221> NAME/KEY: misc_feature
<222> LOCATION: (12)..(131)
<223> OTHER INFORMATION: n is a, c, g, or t

<400> SEQUENCE: 43
ggatcctgga gnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn ngtcggatcc                                                 140

<210> SEQ ID NO 44
<211> LENGTH: 112
<212> TYPE: DNA
<213> ORGANISM: Artificial
<220> FEATURE:
<223> OTHER INFORMATION: Oligonucleotide of FIG. 8 sense strand without
      M&G linker inserted removed by electrophesis
<220> FEATURE:
<221> NAME/KEY: misc_feature
<222> LOCATION: (8)..(106)
<223> OTHER INFORMATION: n is a, c, g, or t

<400> SEQUENCE: 44
gatccgannn nnnnnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnctcc ag              112

<210> SEQ ID NO 45
<211> LENGTH: 112
<212> TYPE: DNA
<213> ORGANISM: Artificial
<220> FEATURE:
<223> OTHER INFORMATION: Oligonucleotide of FIG. 8 antisense strand
      without M&G linker inserted removed by electrophesis
<220> FEATURE:
<221> NAME/KEY: misc_feature
<222> LOCATION: (11)..(109)
<223> OTHER INFORMATION: n is a, c, g, or t

<400> SEQUENCE: 45
gatcctggag nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnt cg             112
```

```
<210> SEQ ID NO 46
<211> LENGTH: 59
<212> TYPE: DNA
<213> ORGANISM: Artificial
<220> FEATURE:
<223> OTHER INFORMATION: Oligonucleotide of FIG. 9 sense strand before
      insertion of M&G linker
<220> FEATURE:
<221> NAME/KEY: misc_feature
<222> LOCATION: (1)..(23)
<223> OTHER INFORMATION: n is a, c, g, or t
<220> FEATURE:
<221> NAME/KEY: misc_feature
<222> LOCATION: (30)..(59)
<223> OTHER INFORMATION: n is a, c, g, or t

<400> SEQUENCE: 46
nnnnnnnnnn nnnnnnnnnn nnntccgacn nnnnnnnnnn nnnnnnnnnn nnnnnnnnn          59

<210> SEQ ID NO 47
<211> LENGTH: 59
<212> TYPE: DNA
<213> ORGANISM: Artificial
<220> FEATURE:
<223> OTHER INFORMATION: Oligonucleotide of FIG. 9 sense strand before
      insertion of M&G linker
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (37)..(59)
<223> OTHER INFORMATION: n is a, c, g, or t

<400> SEQUENCE: 47
nnnnnnnnnn nnnnnnnnnn nnnnnnnnnn gtcggannnn nnnnnnnnnn nnnnnnnnn          59

<210> SEQ ID NO 48
<211> LENGTH: 140
<212> TYPE: DNA
<213> ORGANISM: Artificial
<220> FEATURE:
<223> OTHER INFORMATION: Oligonucleotide of FIG. 9 sense strand with
      part of M&G linker inserted (rest of plasmid not shown)
<220> FEATURE:
<221> NAME/KEY: misc_feature
<222> LOCATION: (10)..(58)
<223> OTHER INFORMATION: n is a, c, g, or t
<220> FEATURE:
<221> NAME/KEY: misc_feature
<222> LOCATION: (65)..(129)
<223> OTHER INFORMATION: n is a, c, g, or t

<400> SEQUENCE: 48
ggatccgacn nnnnnnnnnn nnnnnnnnnn nnnnnnnnnn nnnnnnnnnn nnnnnnnntc          60
cgacnnnnnn nnnnnnnnnn nnnnnnnnnn nnnnnnnnnn nnnnnnnnnn nnnnnnnnnn         120
nnnnnnnnnc tccaggatcc                                                     140

<210> SEQ ID NO 49
<211> LENGTH: 140
<212> TYPE: DNA
<213> ORGANISM: Artificial
<220> FEATURE:
<223> OTHER INFORMATION: Oligonucleotide of FIG. 9 antisense strand
      with part of M&G linker inserted (rest of plasmid not shown)
<220> FEATURE:
<221> NAME/KEY: misc_feature
<222> LOCATION: (12)..(76)
<223> OTHER INFORMATION: n is a, c, g, or t
```

```
<220> FEATURE:
<221> NAME/KEY: misc_feature
<222> LOCATION: (83)..(131)
<223> OTHER INFORMATION: n is a, c, g, or t

<400> SEQUENCE: 49
ggatcctgga gnnnnnnnnn nnnnnnnnnn nnnnnnnnnn nnnnnnnnnn nnnnnnnnnn      60
nnnnnnnnnn nnnnnngtcg gannnnnnnn nnnnnnnnnn nnnnnnnnnn nnnnnnnnnn     120
nnnnnnnnnn ngtcggatcc                                                 140

<210> SEQ ID NO 50
<211> LENGTH: 126
<212> TYPE: DNA
<213> ORGANISM: Artificial
<220> FEATURE:
<223> OTHER INFORMATION: Oligonucleotide of FIG. 9 sense strand with
      partial M&G linker inserted after restriction enzyme digestion
      (rest of plasmid not shown)
<220> FEATURE:
<221> NAME/KEY: misc_feature
<222> LOCATION: (10)..(44)
<223> OTHER INFORMATION: n is a, c, g, or t
<220> FEATURE:
<221> NAME/KEY: misc_feature
<222> LOCATION: (51)..(115)
<223> OTHER INFORMATION: n is a, c, g, or t

<400> SEQUENCE: 50
ggatccgacn nnnnnnnnnn nnnnnnnnnn nnnnnnnnnn nnnntccgac nnnnnnnnn       60 nnnnnnnnnn nnnnnnnnnn nnnnnnnnnn nnnnnnnnnn nnnnnnnnnn nnnnnctcca    120
ggatcc                                                                126

<210> SEQ ID NO 51
<211> LENGTH: 126
<212> TYPE: DNA
<213> ORGANISM: Artificial
<220> FEATURE:
<223> OTHER INFORMATION: Oligonucleotide of FIG. 9 antisense strand
      with partial M&G linker inserted after restriction enzyme
      digestion (rest of plasmid not shown)
<220> FEATURE:
<221> NAME/KEY: misc_feature
<222> LOCATION: (12)..(76)
<223> OTHER INFORMATION: n is a, c, g, or t
<220> FEATURE:
<221> NAME/KEY: misc_feature
<222> LOCATION: (83)..(117)
<223> OTHER INFORMATION: n is a, c, g, or t

<400> SEQUENCE: 51
ggatcctgga gnnnnnnnnn nnnnnnnnnn nnnnnnnnnn nnnnnnnnnn nnnnnnnnnn      60
nnnnnnnnnn nnnnnngtcg gannnnnnnn nnnnnnnnnn nnnnnnnnnn nnnnnnngtc     120
ggatcc                                                                126

<210> SEQ ID NO 52
<211> LENGTH: 120
<212> TYPE: DNA
<213> ORGANISM: Artificial
<220> FEATURE:
<223> OTHER INFORMATION: Oligonucleotide of FIG. 9 sense strand excised
      from plasmid and removed by electrophoresis as it is too long
<220> FEATURE:
<221> NAME/KEY: misc_feature
<222> LOCATION: (9)..(43)
<223> OTHER INFORMATION: n is a, c, g, or t
<220> FEATURE:
<221> NAME/KEY: misc_feature
<222> LOCATION: (50)..(114)
```

<223> OTHER INFORMATION: n is a, c, g, or t

<400> SEQUENCE: 52
gatccgacnn nnnnnnnnnn nnnnnnnnnn nnnnnnnnnn nnntccgacn nnnnnnnnnn    60
nnnnnnnnnn nnnnnnnnnn nnnnnnnnnn nnnnnnnnnn nnnnnnnnnn nnnnctccag   120

<210> SEQ ID NO 53
<211> LENGTH: 120
<212> TYPE: DNA
<213> ORGANISM: Artificial
<220> FEATURE:
<223> OTHER INFORMATION: Oligonucleotide of FIG. 9 antisense strand
      excised from plasmid and removed by electrophoresis as it is too
      long
<220> FEATURE:
<221> NAME/KEY: misc_feature
<222> LOCATION: (11)..(75)
<223> OTHER INFORMATION: n is a, c, g, or t
<220> FEATURE:
<221> NAME/KEY: misc_feature
<222> LOCATION: (82)..(116)
<223> OTHER INFORMATION: n is a, c, g, or t

<400> SEQUENCE: 53
gatcctggag nnnnnnnnnn nnnnnnnnnn nnnnnnnnnn nnnnnnnnnn nnnnnnnnnn    60
nnnnnnnnnn nnnnngtcgg annnnnnnnn nnnnnnnnnn nnnnnnnnnn nnnnnngtcg   120

<210> SEQ ID NO 54
<211> LENGTH: 85
<212> TYPE: DNA
<213> ORGANISM: Artificial
<220> FEATURE:
<223> OTHER INFORMATION: Oligonucleotide of FIG. 10 sense strand with
      M&G linker inserted in the opposite orientation
<220> FEATURE:
<221> NAME/KEY: misc_feature
<222> LOCATION: (1)..(23)
<223> OTHER INFORMATION: n is a, c, g, or t
<220> FEATURE:
<221> NAME/KEY: misc_feature
<222> LOCATION: (56)..(85)
<223> OTHER INFORMATION: n is a, c, g, or t

<400> SEQUENCE: 54
nnnnnnnnnn nnnnnnnnnn nnnagtcgga ggccaaggcg gccgtacgct ggagtnnnnn    60
nnnnnnnnnn nnnnnnnnnn nnnnn                                         85

<210> SEQ ID NO 55
<211> LENGTH: 85
<212> TYPE: DNA
<213> ORGANISM: Artificial
<220> FEATURE:
<223> OTHER INFORMATION: Oligonucleotide of FIG. 10 antisense strand
      with M&G linker inserted in the opposite orientation
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (63)..(85)
<223> OTHER INFORMATION: n is a, c, g, or t

<400> SEQUENCE: 55
nnnnnnnnnn nnnnnnnnnn nnnnnnnnnn actccagcgt acggccgcct tggcctccga    60
ctnnnnnnnn nnnnnnnnnn nnnnn                                         85

<210> SEQ ID NO 56

```
<211> LENGTH: 148
<212> TYPE: DNA
<213> ORGANISM: Artificial
<220> FEATURE:
<223> OTHER INFORMATION: Oligonucleotide of FIG. 10 sense strand
      inserted into plasmid (rest of plasmid not shown)
<220> FEATURE:
<221> NAME/KEY: misc_feature
<222> LOCATION: (10)..(54)
<223> OTHER INFORMATION: n is a, c, g, or t
<220> FEATURE:
<221> NAME/KEY: misc_feature
<222> LOCATION: (87)..(139)
<223> OTHER INFORMATION: n is a, c, g, or t

<400> SEQUENCE: 56
ggactggagn nnnnnnnnnn nnnnnnnnnn nnnnnnnnnn nnnnagtcgg      60
aggccaaggc ggccgtacgc tggagtnnnn nnnnnnnnnn nnnnnnnnnn     120
nnnnnnnnnn nnnnnnnnng tcggatcc                             148

<210> SEQ ID NO 57
<211> LENGTH: 148
<212> TYPE: DNA
<213> ORGANISM: Artificial
<220> FEATURE:
<223> OTHER INFORMATION: Oligonucleotide of FIG. 10 antisense strand
      inserted into plasmid (rest of plasmid not shown)
<220> FEATURE:
<221> NAME/KEY: misc_feature
<222> LOCATION: (10)..(62)
<223> OTHER INFORMATION: n is a, c, g, or t
<220> FEATURE:
<221> NAME/KEY: misc_feature
<222> LOCATION: (95)..(139)
<223> OTHER INFORMATION: n is a, c, g, or t

<400> SEQUENCE: 57
ggatccgacn nnnnnnnnnn nnnnnnnnnn nnnnnnnnnn nnnnnnnnnn      60
nnactccagc gtacggccgc cttggcctcc gactnnnnnn nnnnnnnnnn     120
nnnnnnnnnn nnnnnnnnnc tccagtcc                             148

<210> SEQ ID NO 58
<211> LENGTH: 62
<212> TYPE: DNA
<213> ORGANISM: Artificial
<220> FEATURE:
<223> OTHER INFORMATION: Intermediate oligonucleotide 1 sense strand
      of FIG. 10
<220> FEATURE:
<221> NAME/KEY: misc_feature
<222> LOCATION: (10)..(53)
<223> OTHER INFORMATION: n is a, c, g, or t

<400> SEQUENCE: 58
ggactggagn nnnnnnnnnn nnnnnnnnnn nnnnnnnnnn nnnnnnnnnn nnngtcggat      60
cc                                                                     62

<210> SEQ ID NO 59
<211> LENGTH: 62
<212> TYPE: DNA
<213> ORGANISM: Artificial
<220> FEATURE:
<223> OTHER INFORMATION: Intermediate oligonucleotide 1 antisense
      strand of FIG. 10
<220> FEATURE:
<221> NAME/KEY: misc_feature
<222> LOCATION: (10)..(53)
<223> OTHER INFORMATION: n is a, c, g, or t
```

-continued

```
<400> SEQUENCE: 59
ggatccgacn nnnnnnnnnn nnnnnnnnnn nnnnnnnnnn nnnnnnnnnn nnnctccagt    60
cc                                                                   62

<210> SEQ ID NO 60
<211> LENGTH: 62
<212> TYPE: DNA
<213> ORGANISM: Artificial
<220> FEATURE:
<223> OTHER INFORMATION: Intermediate oligonucleotide 2 sense strand
      of FIG. 10
<220> FEATURE:
<221> NAME/KEY: misc_feature
<222> LOCATION: (10)..(53)
<223> OTHER INFORMATION: n is a, c, g, or t

<400> SEQUENCE: 60
ggactggagn nnnnnnnnnn nnnnnnnnnn nnnnnnnnnn nnnnnnnnnn nnngtcggat    60
cc                                                                   62

<210> SEQ ID NO 61
<211> LENGTH: 62
<212> TYPE: DNA
<213> ORGANISM: Artificial
<220> FEATURE:
<223> OTHER INFORMATION: Intermediate oligonucleotide 2 antisense
      strand of FIG. 10
<220> FEATURE:
<221> NAME/KEY: misc_feature
<222> LOCATION: (10)..(53)
<223> OTHER INFORMATION: n is a, c, g, or t

<400> SEQUENCE: 61
ggatccgacn nnnnnnnnnn nnnnnnnnnn nnnnnnnnnn nnnnnnnnnn nnnctccagt    60
cc                                                                   62

<210> SEQ ID NO 62
<211> LENGTH: 114
<212> TYPE: DNA
<213> ORGANISM: Artificial
<220> FEATURE:
<223> OTHER INFORMATION: Oligonucleotide sense strand generated by
      incorrect insertion of M&G linker removed by electrophoresis
<220> FEATURE:
<221> NAME/KEY: misc_feature
<222> LOCATION: (8)..(108)
<223> OTHER INFORMATION: n is a, c, g, or t

<400> SEQUENCE: 62
gatccgannn nnnnnnnnn nnnnnnnnnn nnnnnnnnnn nnnnnnnnnn nnnnnnnnnn     60
nnnnnnnnnn nnnnnnnnnn nnnnnnnnnn nnnnnnnnnn nnnnnnnnct ccag         114

<210> SEQ ID NO 63
<211> LENGTH: 114
<212> TYPE: DNA
<213> ORGANISM: Artificial
<220> FEATURE:
<223> OTHER INFORMATION: Oligonucleotide antisense strand generated
      by incorrect insertion of M&G linker removed by electrophoresis
```

-continued

```
<220> FEATURE:
<221> NAME/KEY: misc_feature
<222> LOCATION: (11)..(111)
<223> OTHER INFORMATION: n is a, c, g, or t

<400> SEQUENCE: 63
gatcctggag nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn ntcg          114
```